(12) United States Patent
Wang-Pruski et al.

(10) Patent No.: US 7,868,153 B2
(45) Date of Patent: Jan. 11, 2011

(54) CINNAMIC ACID 4-HYDROXYLASE

(75) Inventors: Gefu Wang-Pruski, Truro (CA); Sandra Cantle, Truro (CA); Karthikeyan Narayanan, Truro (CA)

(73) Assignee: Her Majesty the Queen in right of The Province of Nova Scotia, as represented by The Nova Scotia Agricultural College (NSAC), Truro, Nova Scotia (CA)

( * ) Notice: Subject to any disclaimer, the term of this patent is extended or adjusted under 35 U.S.C. 154(b) by 1030 days.

(21) Appl. No.: 11/452,342

(22) Filed: Jun. 14, 2006

(65) Prior Publication Data
US 2007/0163006 A1 Jul. 12, 2007

Related U.S. Application Data

(60) Provisional application No. 60/690,154, filed on Jun. 14, 2005.

(51) Int. Cl.
*A01H 5/00* (2006.01)
*A01H 5/04* (2006.01)
*C12Q 1/68* (2006.01)
*C12P 19/34* (2006.01)
*C12N 15/29* (2006.01)

(52) U.S. Cl. .................... 536/23.6; 536/23.1; 536/23.2; 536/24.3; 536/24.33; 435/6; 435/91.1; 435/91.2; 800/317.2

(58) Field of Classification Search ........................ None
See application file for complete search history.

(56) References Cited

PUBLICATIONS

Wang-Pruski, G. et al., Amer. J. of Potato Res.; (Jan./Feb. 2004), vol. 81, pp. 7-16.*
Altschul, S.F., et al. "Basic Local Alignment Search Tool", J. Mol. Biol. (1990) 215, 403-410.
Arumuganathan, K. and Earle, E.D. "Nuclear DNA Content of Some Important Plant Species", Plant Molecular Biology Reporter, (1991) vol. 9(3), 208-218.
Bachem, C.W.B., et al. "Visualization of differential gene expression using a novel method of RNA fingerprinting based on AFLP: Analysis of gene expression during potato tuber development", The Plant Journal (1996) 9(5), 745-753.
Bassett, C.L. et al. "Characterization of the peach homologue of the ethylene receptor, *PpETR1*, reveals some unusual features regarding transcript processing", Planta (2002) 215:679-688.
Batard, Y. et al. "Regulation of the Cinnamate 4-Hydroxylase (CYP73A1) in Jerusalem Artichoke Tubers in Response to Wounding and Chemical Treatments", Plant Physiol. (1997) 113:951-959.
Belasco, J.G. and Higgins, C.F. "Mechanisms of mRNA decay in bacterial: a perspective", Gene, 72 (1988) 15-23.
Bell-Lelong, D.A. et al. "Cinnamate-4-Hydroxylase Expression in *Arabidopsis*—Regulation in Response to Development and the Environment", Plant Physiol. (1997) 113:729-738.
Betz, C. et al "Differential expression of two cinnamate 4-hydroxylase genes in 'Valenci' orange (*Citrus sinensis* Osbeck)", Plant Molecular Biology (2001) 46:741-748.
Blee, K. et al. "Antisense and sense expression of cDNA coding for CYP73A15, a class II cinnamate 4-hydroxylase, leads to a delayed and reduced production of lignin in tobacco", Phytochemistry 57 (2001) 1159-1166.
Bradshaw, J.E. et al. "Applied potato genetics and breeding: the way ahead for potato breeding", Breeding & genetics, p. 76-80, 1997-1998.
Chapple, C. "Molecular-Geentic Analysis of Plant Cytochrome P450-Dependent Monooxygenases", Annu. Rev. Plant Physiol. Plant Mol. Biol. (1998) 49:311-43.
Chubey, B.B. and Mazza, G. "A Non-Destructive Method for Rapid Evaluation of Boiling Quality of Potato Tubers", American Potato Journal, 60 (1983) 693-698.
Deutsch, M. and Long, M., "intron-exon structures of eukaryotic model organisms", Nucleic Acids Research (1999) 27:15, 3219-3228.
Dinesh-Kumar, S.P. and Baker, B.J., "Alternatively spliced *N* resistance gene transcripts: Their possible role in tobacco mosaic virus resistance", PNAS (2000) 97:4, 1908-1913.
Ellis, T.H.N. and Poyser, S.J., "An integrated and comparative view of pea genetic and cytogenetic maps", New Phytologist (2002) 153:17-25.
Fahrendorf, T. and Dixon, R.A., "Stress Responses in Alfalfa (*Medicago sativa* L.) XVIII: Molecular Cloning and Expression of the Elicitor-Inducible Cinnamic Acid 4-Hydroxylase Cytochrome P450", Archives of Biochemistry and Biophysics (1993) 305:2, 509-515.
Floyd, S.K. and Bowman, J.L., "Ancient microRNA target sequences in Plants", Nature (2004) 428, 485-486.
Friedman, M., "Chemistry, Biochemistry, and Dietary Role of Potato Polyphenols. A Review." J. Agric. Food Chem. (1997) 45, 1523-1540.

(Continued)

*Primary Examiner*—Russell Kallis
(74) *Attorney, Agent, or Firm*—Micheline Gravelle; Bereskin & Parr, LLP/S.E.N.C.R.L., s.r.l.

(57) ABSTRACT

After-cooking darkening is a gray-black discoloration of the potato tuber, formed after cooking by the oxidation of an iron-chlorogenic acid complex. Cinnamic acid 4-hydroxylase (C4H) is a key enzyme involved in the biosynthesis of chlorogenic acid. The full-length c4h gene was cloned and sequenced from both genomic DNA and cDNA of Russet Burbank tuber tissue by PCR and 5' and 3' RACE. The gene expression levels of c4h were examined by Northern hybridization, relative quantitative RT-PCR and real time quantitative RT-PCR in potato cultivars and wide selection of diploid clones varying in susceptibility to after-cooking darkening. Results suggest that there is a relationship between the levels of c4h gene expression and the degree of after-cooking darkening in potato tubers. The inhibition of C4H gene expression and over expression of C4H expression were also examined. The successful inhibition of the gene expression will lead to the reduced biosynthesis of chlorogenic acid, reducing the susceptibility of after-cooking darkening. The successful overexpression of the C4H gene will lead to the increase in the chlorogenic acid in plant tissues, gaining the resistance to diseases. In addition, due to the natural antioxidant activity of chlorogenic acid, overexpression of C4H gene will lead to its over production in plant tissues, such as potato tubers.

3 Claims, 26 Drawing Sheets

OTHER PUBLICATIONS

Gabriac, B. et al. "Purificatin and Immunocharacterization of a Plant Cytochrome P450: The Cinnamic Acid 4-Hydroxylase", Archives of Biochemistry and Biophysics (1991) 288:1, 302-309.

Griffiths, D.W. and Bain, H., "Photo-induced changes in the concentrations of individual chlorogenic acid isomers in potato (*Solanum tuberosum*) tubers and their complexation with ferric ions", Potato Research 40 (1997) 307-315.

Groenewald, J.-H. et al., "The introduction of an inverted repeat to the 5' untranslated leader sequence of a transgene strongly inhibits gene expression", Plant Cell Reports (2000) 19:1098-1101.

Hotze, M. et al., "Cinnamate 4-hydroxylase from *Catharanthus roseus*, and a strategy for the functional expression of plant cytochrome P450 proteins as translational fusions with P450 reductase in *Escherichia coli*", FEBS Letters 374 (1995) 345-350.

Hughes, J.C. and Evans, J.L., "Studies on After-Cooking Blackening in Potatoes", Eur. Potato J., vol. 10 (1967) No. 1, 16-36.

Hughes, J.C., "Chemistry of After-Cooking Discoloration in Potatoes", J. nat. agric. Bol., (1962) 9:235-236.

Hughes, J.C. and Swain, T., "After-Cooking Blackening in Potatoes. II.-Core Experiments", J. Sci. Food Agric, (1962) 13:229-236.

Hughes, J.C., and Swain, T., "After-Cooking Blackening in Potatoes. III.-Examination of the Interaction of Factors by in vitro Experiments". J. Sci. Food Agric, (1962) 13:358-363.

Inoue, H. et al., "High efficiency transformation of *Escherichia coli* with plasmids", Gene 96 (1990) 23-28.

Kawai, S. et al., "Isolation and Analysis of Cinnamic Acid 4-Hydroxylase Homologous Genes from a Hybrid Aspen, *Populus kitakamiensis*", Biosci. Biotech. Biochem, (1996) 60 (10), 1586-1597.

Ke, X.-S. et al., "MicroRNAs: key participants in gene regulatory networks", Current Opinion in Chemical Biology (2003), 7:516-523.

Kendziorski, C.M., "The efficiency of pooling mRNA in microarray experiments", Biostatistics (2003), 4, 3, 465-477.

Kochetov, A.V. et al., "Contextual Features of Higher Plant mRNA 5'-Untranslated Regions", Mol. Biol., vol. 36, No. 4 (2002), 510-516.

König, H. et al., "Coupling of signal transduction to alternative pre-mRNA splicing by a composite splice regulator", The EMBO Journal (1998) vol. 17, No. 10, p. 2904-2913.

Koopmann, E. et al., "Regulation and Functional Expression of Cinnamate 4-Hydroxylas from Parsley", Plant Physiol. (1999), vol. 119, p. 49-55.

Kuhn, J. et al. "Transcript Lifetime is Balanced between Stabilizing Stem-Loop Structures and Degradation-Promoting Polyadenylation in Plant Mitochondria", Mol. and Cell. Biol. (2001), vol. 21, No. 3, 731-742.

Kühnl, T. et al., "Chlorogenic Acid Biosynthesis: Characterization of a Light-Induced Microsomal 5-*O*-(4-Coumaroyl)-D-quinate/shikimate 3'-Hydroxylase from Carrot (*Daucus carota* L.) Cell Suspension Cultures", Archives of Biochem. and Biophys. (1987), vol. 258, No. 1, 226-232.

Landschütze, V. et al., "Mitochondrial citrate synthase from potato: predominant expression in mature leaves and young flower buds", Planta (1995) 196:756-764.

Lewis, C.E. et al., "Determination of Anthocyanins, Flavonoids and Phenolic Acids in Potatoes. I: Coloured Cutivars of *Solanum tuberosum* L", J. Sci. Food Agric, (1998) 77, 45-57.

Lugasi, A. et al., "Chlorogenic Acid Content and Antioxidant Properties of Potato Tubers as Related to Nitrogen Fertilisation", Acta Alimentaria (1999), vol. 28(2), 183-195.

Ma, R. et al., "Black Swallowtail (*Papilio polyxenes*) Alleles Encode Cytochrome P450s that Selectively Metabolize Linear Furanocoumarins", Archives of Biochem. and Biophys. (1994), vol. 310, No. 2, 332-340.

McLysaght, A. et al. "Estimation of synteny conservation and genome compaction between pufferfish (*Fugu*) and human", Yeast (2000) 17:22-36.

Miller, C.L. et al. "Evaluating RNA status for RT-PCR in extracts of postmortem human brain tissue", BioTechniques (2004), vol. 36, No. 4, 628-633.

Mizutani, M et al., "Isolation of a cDNA and a Genomic Clone Encoding Cinnamate 4-Hydroxylase from *Arabidopsis* and its Expression Manner in Planta". Plant Physiol. (1997), 113:755-763.

Moriyama, E.N. et al., "Genome Size and Intron Size in *Drosophila*", Mol. Biol. Evol. 15(6):770-773 (1998).

Nedelkina, S. et al., "Novel characteristics and regulation of a divergent cinnamate 4-hydroxylase (CYP73A15) from French bean: engineering expression in yeast", Plant Molecular Biology (1999) 39:1079-1090.

Niggeweg, R. et al. "Engineering plants with increased levels of the antioxidant chlorogenic acid", Nature Biotechnology (2004), vol. 22, No. 6, 746-754.

Ortiz, R. and Peloquin, S.J., "Use of 24-Chromosome Potatoes (Diploids and Dihaploids) for Genetical Analysis", Potato Genetics, Edited by J.E. Bradshow and G.R. Mackay, 6, 133-135, 296-297.

Palmer, M. and Prediger, "Assessing RNA Quality", Abion TechNotes 11(1) (2007).

Peng, X. et al., "Statistical implications of pooling RNA samples for microarray experiments", BMC Bioinformatics (2003) 4:26.

Percival, G.C. and Baird, L. Influence of Storage upon Light-Induced Chlorogenic Acid Accumulation in Potato Tubers (*Solanum tuberosum* L.), J. Agric. Food Chem. (2000), 48, 2476-2482.

Pesole, G. et al. "Structural and compositional features of untraslated regions of eukaryotic mRNAs", Gene 205 (1997) 95-102.

Petersen, M., "Cinnamic acid 4-hydroxylase from cell cultures of the hornwort *Anthoceros agrestis*", Planta (2003) 217:96-101.

Wang-Pruski, G. and Tarn, T.R., "Digital-Imaging Analysis—A New Method For Evaluation of Potato After-Cooking Darkening", Proc. XXVI IHC-Potatoes-Health Food for Humanity, Ed. R.Y. Yada, Acta Hort. 619, ISHS 2003, 399-404.

Wang-Pruski, G. and Nowak, J., "Potato After-Cooking Darkening", Amer J of Potato Res (2004) 81:7-16.

Rhoades, M.W., et al. "Prediction of Plant MicroRNA Targets", Cell (2002), vol. 110, 513-520.

Ro, D.K. et al., "Functional Characterization and Subcellular Localization of Poplar (*Populus trichocarpa* x *Populus deltoides*) Cinnamate 4-Hydroxylase", Plant Physiology (2001), vol. 126, p. 317-329.

Schalk, M. et al., "Role of Unusual Amino Acid Residues in the Proximal and Distal Heme Regions of a Plant P450, CYP73A1", Biochemistry (1999), 38, 6093-6103.

Siciliano, J. et al., "Relation of Potato Size to After-Cooking Blackening Tendency", American Journal of Potato (1969), vol. 46, 91-97.

Singh, G. et al. "A Quick Method to Isolate RNA from Wheat and Other Carbohydrate-Rich Seeds", Plant Molecular Biology Reporter (2003) 21:93a-93f.

Smith, O. "After-Cooking Darkening", Potato Processing—4. Effect of Cultural and Environmental Conditions (1987), 107-147.

Sullivan, M.L. and Green, P.J., "Mutational analysis of the DST element in tobacco cells and transgenic plants: Identification of residues critical for mRNA instability", RNA (1996) 2:308-315.

Tanaka, Y. et al., "Properties, development and cellular-localization of cinnamic acid 4-hydroxylase in cut-injured sweet potato", Plant & Cell Physiol. (1974) 15:843-854.

Tanzer, M.M. and Meagher, R.B., "Faithful Degradation of Soybean rbcS mRNA In Vitro", Molecular and Cellular Biology (1994), vol. 14, No. 4, 2640-2650.

Taylor, G. "Populus: *Arabidopsis* for Forestry. Do We Need a Model Tree?", Annals of Botany (2002), 90:681-689.

The *Arabidopsis* Genome Initiative, "Analysis of the genome sequence of the flowering plant *Arabidopsis thaliana*", Nature (2000), vol. 408, 796-815.

Trindade, L.M. et al., "Isolation of a Gene Encoding a Copper Chaperone for the Copper/Zinc Superoxide Dismutase and Characterization of Its Promoter in Potato", Plant Physiology (2003), vol. 133, p. 618-629.

Wendel, J.F. et al. "Intron Size and Genome Size in Plants", Mol. Biol. Evol. (2002) 19(12):2346-2352.

Whitbred J.M. and Schuler, M.A., "Molecular Characterization of *CYP73A9* and *CYP82A1* P450 Genes Involved in Plant Defense in Pea", Plant Physiology (2000), vol. 124, p. 47-58.

Xie, Z. et al., "Negative Feedback Regulation of *Dicer-Like1* in *Arabidopsis* by microRNA-Guided mRNA Degradation", Current Biology (2003), vol. 13, 784-789.

Yao, K. et al., "Creation of a Metabolic Sink for Tryptophan Alters the Phenylpropanoid Pathway and the Susceptibility of Potato to *Phytophthora infestans*", The Plant Cell (1995), vol. 7, 1787-1799.

Yu, H. and Kumar, P.P., "Post-transcriptional gene silencing in plants by RNA", Plant Cell Rep. (2003) 22:167-174.

Zufall, R.A. and Rausher, M.D., The Genetic Basis of a Flower Color Polymorphism in the Common Morning Glory (*Ipomoea purpurea*), J. of Heredity (2003) 94(6):442-448.

* cited by examiner

SEQUENCE LISTING

<160> NUMBER OF SEQ ID NOS: 34

<210> SEQ ID NO 1
<211> LENGTH: 2986
<212> TYPE: DNA
<213> ORGANISM: Solanum tuberosum

<400> SEQUENCE: 1

```
aaacattctt ttctcaaact tccctctgaa agaactcacc aaaaatggat cttctcttac      60
tggagaagac cttaataggt cttttctttg ctattttaat cgctattatt gtctctaaac     120
ttcgttccaa gcgatttaaa ctaccccag gtccaattcc agtcccagtt tttggaaatt      180
ggcttcaagt tggtgatgat ttgaaccata gaaaccttac tgagtatgct aaaaagtttg     240
gtgatgtgtt cttgcttaga atggggcaaa ggaacttagt tgttgtgtca tccctgaat      300 tagctaaaga agttttacac acacaagggg ttgaatttgg ttcaagaaca agaaatgttg     360
tttttgatat ttttacaggg aagggtcaag atatggtttt tacagtgtat ggtgagcact     420
ggaggaaaat gaggaggatt atgactgtac cctttttac taataaggtg gtgcagcagt      480 atagagggg gtgggagtct gaggctgcta gtgtagttga ggatgtgaag aaaaaccctg      540
aatctgctac aaatgggatt gttttgagga aaagattgca gcttatgatg tataataaca     600
tgtttaggat tatgtttgat aggagatttg agagtgaaga tgatcccctt tttgttaagc     660
ttagggcttt gaatggtgag aggagtagat tggctcagag ctttgagtac aactatggtg     720
attttatccc tattttgagg cctttcttga gagggtactt gaagatttgt aaggaggtta     780
aggagaagag gttgaagcta ttcaaagact actttgttga tgaaagaaag taagttcact     840
tttttcttgt taatcccttt atgctcaatt tgatcatttg tatcagtttt atttattagt     900
ttagtttagt tgtaaggggt gtttgactaa atcttggaac agtatggatc aattttgaat     960
agaaaaggaa gtactagttg acatttcaga atagtaaggg tccattggtt aaattttaaa    1020
aaaggtagtt cttgttttct gttttcaaag tgataatgaa aattagcgtg gtgtttggca    1080
tatttggagt tgtttttgcga ttctcctgtg gcaattagag gtttgtcgta acggtggcct    1140
gtgagagcct agcttgcagt ggtaagagta gtgagtgatt tggagtaaaa aagttaataa    1200 cttttttgatt gatgttttt aaattttag ttgaattcca gaattggcca ataagaatca    1260
```

-continued

```
tgtatgattt agtgatagtt aaagtgcttt gaggtactgt taggtagctt ttgatggtgg    1320
accttgtgtt ttagtttgta atatttttat tgctttacac aggaagcttg caaataccaa    1380
gagcatggac agcaatgctc taaaatgtgc aattgatcac attcttgaag ctcaacagaa    1440
gggagagatc aacgaggata acgttcttta catcgttgag aacatcaatg ttgctggtat    1500
gtttcgaaat aacatatctt tgattctcta gagtaaaatt tgttctagtt tggtttaaat    1560
gattgcatcc tagttagaat aaaagtaatt tataagtgaa tgaaaatcca attccaattt    1620
tgtctatttt tctcaaaagt agtagttgag agttaccaaa taaggggccc aagatttaac    1680
tgttttttat gttgccaagg actagttggt gcctgggccc tgggggggtac cacacaccaa    1740 tttcttgtgg taaataagat gttatgttta catccaagga agacatgtag tttccaagtt    1800 tgaagggaa ataagtacta tagtaaaatg aaccacatgt ttcaagtgat ggcgatgttt    1860
ctaggctagg ttacaaagac ttgttaggta ccacaattct tatactacta taagacttaa    1920
gtcccaaaca aagttggata caatcgggtt ctatgggttt tactgaattc attgcttttg    1980
aagtgtgcat acatatgaaa agaatttgt aatgtataca tatgtaatga gatcatacat    2040
attttgaact caataacggg tagatcttgg aattgcctct tgtccggaag ttgtttcatt    2100
tattgcatcg ccttgtagta agtaatacat gagttttgat atggtcttaa acttaaaaag    2160
tcacacatcc taccattgaa gcatgttttg ttgtttatat ctgttcgtaa acttcttggt    2220
tagttgatta ttcagctgat atgcttaatt actgtcgtga ccagcaatcg aaacaacatt    2280
gtggtcaatt gagtggggta tcgcggaact agtcaaccac cctcatatcc aaaagaaact    2340
ccgtgatgag attgatacag ttcttggacc aggaatgcaa gtgactgagc cagacatgcc    2400
caagcttccg taccttcagg ctgtgatcaa ggagactctt agactcagga tggcaattcc    2460
tcttttagtc ccacacatga accttcatga tgcaaagctt gctggatacg atattccagc    2520
tgaaagcaaa atcttagtta acgcttggtg gctagctaac aaccccgctc actgaagaa    2580 acctgaagag ttcagacctg agaggttctt cgaagaggag aagcacgttg aggccaatgg    2640
caacgacttc agatttcttc ctttcggtgt tggtaggagg agttgccccg gaattatcct    2700
tgcattgcca attctcggca tcactttggg acgtttggtg cagaactttg agatgttgcc    2760
tcctccagga cagtcaaagc tcgacacctc ggagaaaggt ggacagttca gtctccacat    2820
tttgaagcat tccaccattg tgatgaaacc aagatctttc taaactttgt aatgctatca    2880
attaatcatg attgttgttt gtttgtgtaa acctttaag tttgacagaa acattcttc    2940 tttcttatgt tttataaaag tcttattgga ctagattatt cattat                  2986
```

<210> SEQ ID NO 2
<211> LENGTH: 505
<212> TYPE: PRT
<213> ORGANISM: Solanum tuberosum

<400> SEQUENCE: 2

```
Met Asp Leu Leu Leu Glu Lys Thr Leu Ile Gly Leu Phe Phe Ala
1               5                   10                  15

Ile Leu Ile Ala Ile Ile Val Ser Lys Leu Arg Ser Lys Arg Phe Lys
                20                  25                  30

Leu Pro Pro Gly Pro Ile Pro Val Pro Val Phe Gly Asn Trp Leu Gln
            35                  40                  45

Val Gly Asp Asp Leu Asn His Arg Asn Leu Thr Glu Tyr Ala Lys Lys
        50                  55                  60
```

```
Phe Gly Asp Val Phe Leu Leu Arg Met Gly Gln Arg Asn Leu Val Val
 65                  70                  75                  80

Val Ser Ser Pro Glu Leu Ala Lys Glu Val Leu His Thr Gln Gly Val
                 85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Tyr Arg Gly Gly Trp Glu Ser Glu Ala Ala Ser Val Val Glu Asp
145                 150                 155                 160

Val Lys Lys Asn Pro Glu Ser Ala Thr Asn Gly Ile Val Leu Arg Lys
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Leu Phe Val Lys Leu Arg Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Lys
225                 230                 235                 240

Ile Cys Lys Glu Val Lys Glu Lys Arg Leu Lys Leu Phe Lys Asp Tyr
                245                 250                 255

Phe Val Asp Glu Arg Lys Lys Leu Ala Asn Thr Lys Ser Met Asp Ser
            260                 265                 270

Asn Ala Leu Lys Cys Ala Ile Asp His Ile Leu Glu Ala Gln Gln Lys
        275                 280                 285

Gly Glu Ile Asn Glu Asp Asn Val Leu Tyr Ile Val Glu Asn Ile Asn
    290                 295                 300

Val Ala Ala Ile Glu Thr Thr Leu Trp Ser Ile Glu Trp Gly Ile Ala
305                 310                 315                 320

Glu Leu Val Asn His Pro His Ile Gln Lys Lys Leu Arg Asp Glu Ile
                325                 330                 335

Asp Thr Val Leu Gly Pro Gly Met Gln Val Thr Glu Pro Asp Met Pro
            340                 345                 350

Lys Leu Pro Tyr Leu Gln Ala Val Ile Lys Glu Thr Leu Arg Leu Arg
        355                 360                 365

Met Ala Ile Pro Leu Leu Val Pro His Met Asn Leu His Asp Ala Lys
    370                 375                 380

Leu Ala Gly Tyr Asp Ile Pro Ala Glu Ser Lys Ile Leu Val Asn Ala
385                 390                 395                 400

Trp Trp Leu Ala Asn Asn Pro Ala His Trp Lys Lys Pro Glu Glu Phe
                405                 410                 415

Arg Pro Glu Arg Phe Phe Glu Glu Lys His Val Glu Ala Asn Gly Asn
            420                 425                 430

Asn Asp Phe Arg Phe Leu Pro Phe Gly Val Gly Arg Arg Ser Cys Pro
        435                 440                 445

Gly Ile Ile Leu Ala Leu Pro Ile Leu Gly Ile Thr Leu Gly Arg Leu
    450                 455                 460

Val Gln Asn Phe Glu Met Leu Pro Pro Pro Gly Gln Ser Lys Leu Asp
465                 470                 475                 480

Thr Ser Glu Lys Gly Gly Gln Phe Ser Leu His Ile Leu Lys His Ser
```

```
                    485                 490                 495
Thr Ile Val Met Lys Pro Arg Ser Phe
        500                 505

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
atggatcttc tcttactgga g                                              21

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggtttacaca aacaaacaac                                                20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
taatacgact cactataggg                                                20

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
gatttaggtg acactatag                                                 19

<210> SEQ ID NO 7
<211> LENGTH: 17
<212> TYPE: DNA
<213> ORGANISM: Artificial Sequence
<220> FEATURE:
<223> OTHER INFORMATION: primer

<400> SEQUENCE: 7
ccccaggtcc aattcca                                                   17

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ttcaggggat gacacaacag                                                20

<210> SEQ ID NO 9
```

```
<211> LENGTH: 20
<212> TYPE: DNA
<213> ORGANISM: Artificial Sequence
<220> FEATURE:
<223> OTHER INFORMATION: primer

<400> SEQUENCE: 9
ctgttgtgtc atcccctgaa                                                    20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
cctcattttc ctccagtgct                                                    20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ggcctttctt gagggttac                                                     20

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
cctcgttgat ctctcccttc t                                                  21

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gaagggagag atcaacgagg                                                    20

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
tcacagcctg aaggtatgg                                                     19

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
```
ccactggaag aaacctgaag                                           20

<210> SEQ ID NO 16
<211> LENGTH: 17
<212> TYPE: DNA
<213> ORGANISM: Artificial Sequence
<220> FEATURE:
<223> OTHER INFORMATION: primer

<400> SEQUENCE: 16
ttctgcacca aacgtcc                                              17

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
agcattggag gaagatgagg                                           20

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
gccaatctac tcctctcagc a                                         21

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ggctttgaat ggtgagagga                                           20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tggatatgag ggtggttgac                                           20

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
ttcctccagt gctcaccata c                                         21

<210> SEQ ID NO 22
<211> LENGTH: 22
<212> TYPE: DNA

```
<213> ORGANISM: Artificial Sequence
<220> FEATURE:
<223> OTHER INFORMATION: primer

<400> SEQUENCE: 22
ggtatagaac tgggaaggga ca                                              22

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23 cagggatga cacaacaact                                                  20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
agaggagaag cacgttgagg                                                 20

<210> SEQ ID NO 25
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (39)..(39)
<223> OTHER INFORMATION: V = A, C or G

<400> SEQUENCE: 25
gaccacgcgt atcgatgtcg acttttttttt tttttttv                            39

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
gaccacgcgt atcgatgtcg ac                                              22

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
gaagggagag atcaacgagg                                                 20

<210> SEQ ID NO 28
<211> LENGTH: 17
<212> TYPE: DNA
<213> ORGANISM: Artificial Sequence
<220> FEATURE:
<223> OTHER INFORMATION: primer
```

<400> SEQUENCE: 28
ttctgcacca aacgtcc                                                    17

<210> SEQ ID NO 29
<211> LENGTH: 505
<212> TYPE: PRT
<213> ORGANISM: Capsicum annuum

<400> SEQUENCE: 29

Met Asp Leu Leu Leu Glu Lys Thr Leu Val Gly Leu Phe Phe Ala
1               5                   10                  15

Ile Val Val Ala Ile Ile Val Ser Lys Leu Arg Ser Lys Arg Phe Lys
            20                  25                  30

Leu Pro Pro Gly Pro Ile Pro Val Phe Gly Asn Trp Leu Gln
        35                  40                  45

Val Gly Asp Asp Leu Asn His Arg Asn Leu Thr Asp Tyr Ala Lys Lys
50                  55                  60

Phe Gly Asp Ile Phe Leu Leu Arg Met Gly Gln Arg Asn Leu Val Val
65                      70                  75                  80

Val Ser Ser Pro Glu Ser Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
130                 135                 140

Gln Tyr Arg Gly Gly Trp Glu Ser Glu Val Ala Ser Val Val Glu Asp
145                     150                 155                 160

Val Lys Lys Asn Pro Glu Ser Ala Thr Asn Gly Ile Val Leu Arg Lys
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Pro Phe Val Lys Leu Arg Ala
        195                 200                 205

Leu Asn Ala Glu Arg Ser Arg Leu Ala Gln Ser Phe Glu Tyr Asn Tyr
210                 215                 220

Gly Asp Phe Ile Pro Ile Leu Arg Pro Phe Leu Arg Gly Tyr Leu Lys
225                     230                 235                 240

Ile Cys Lys Glu Val Lys Glu Lys Arg Leu Gln Leu Phe Lys Asp Tyr
                245                 250                 255

Phe Val Asp Glu Arg Lys Lys Leu Ser Asn Thr Lys Ser Met Asp Ser
            260                 265                 270

Asn Ala Leu Lys Cys Ala Ile Asp His Ile Leu Glu Ala Gln Gln Lys
        275                 280                 285

Gly Glu Ile Asn Glu Asp Asn Val Leu Tyr Ile Val Glu Asn Ile Asn
290                 295                 300

Val Ala Ala Ile Glu Thr Thr Leu Trp Ser Ile Glu Trp Gly Ile Ala
305                     310                 315                 320

Glu Leu Val Asn His Pro His Ile Gln Gln Lys Leu Arg Glu Glu Ile
                325                 330                 335

Asp Ala Val Leu Gly Pro Gly Val Gln Val Thr Glu Pro Asp Thr His
            340                 345                 350

```
Lys Leu Pro Asp Leu Gln Ala Val Ile Lys Glu Thr Leu Arg Leu Arg
            355                 360                 365

Met Ala Thr Pro Leu Leu Val Pro His Met Asn Ile His Asp Ala Lys
        370                 375                 380

Leu Ala Gly Tyr Asp Ile Pro Ala Glu Ser Lys Ile Leu Val Asn Pro
385                 390                 395                 400

Trp Trp Leu Ala Asn Asn Pro Ala His Trp Lys Pro Glu Glu Phe
                405                 410                 415

Arg Pro Glu Arg Phe Leu Lys Glu Lys His Val Asp Ala Asn Gly
            420                 425                 430

Asn Asp Phe Arg Phe Leu Pro Phe Gly Val Gly Arg Ser Cys Pro
            435                 440                 445

Gly Ile Ile Leu Ala Leu Pro Ile Leu Gly Ile Thr Leu Gly Arg Leu
        450                 455                 460

Val Gln Asn Phe Glu Leu Leu Pro Pro Gly Gln Ser Lys Leu Asp
465                 470                 475                 480

Thr Thr Glu Lys Gly Gly Gln Phe Ser Leu His Ile Leu Lys His Ser
                485                 490                 495

Thr Ile Val Met Lys Pro Arg Ser Phe
            500                 505

<210> SEQ ID NO 30
<211> LENGTH: 505
<212> TYPE: PRT
<213> ORGANISM: Lithospermum erythrorhizon

<400> SEQUENCE: 30

Met Asp Leu Leu Leu Glu Lys Ala Leu Ile Gly Leu Phe Phe Ser
1               5                   10                  15

Phe Ile Ile Ala Ile Val Ile Ser Lys Leu Arg Gly Lys Lys Phe Lys
                20                  25                  30

Leu Pro Pro Gly Pro Ile Pro Val Pro Ile Phe Gly Asn Trp Leu Gln
            35                  40                  45

Val Gly Asp Asp Leu Asn His Arg Asn Leu Thr Glu Tyr Ala Lys Lys
50                  55                  60

Phe Gly Glu Ile Phe Leu Leu Arg Met Gly Gln Arg Asn Leu Val Val
65                  70                  75                  80

Val Ser Ser Pro Asp Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
130                 135                 140

Gln Tyr Arg Lys Gly Trp Glu Ser Glu Val Ser Val Ile Glu Asp
145                 150                 155                 160

Val Lys Lys Ile Pro Glu Ser Glu Thr Val Gly Ile Val Leu Arg Lys
                165                 170                 175

Arg Leu Gln Leu Met Met Tyr Asn Asn Met Phe Arg Ile Met Phe Asp
            180                 185                 190

Arg Arg Phe Glu Ser Glu Asn Asp Pro Leu Phe Met Lys Leu Arg Ala
        195                 200                 205

Leu Asn Gly Glu Arg Ser Arg Leu Ala Gln Ser Phe Asp Tyr Asn Tyr
210                 215                 220
```

```
Gly Asp Phe Ile Pro Ile Leu Arg Pro Phe Leu Arg Gly Tyr Leu Lys
225                 230                 235                 240

Ile Cys Lys Glu Val Lys Glu Thr Arg Leu Lys Leu Phe Lys Asp Tyr
            245                 250                 255

Phe Val Glu Glu Arg Lys Lys Ile Ala Ser Thr Lys Ser Thr Thr Thr
        260                 265                 270

Asn Gly Leu Lys Cys Ala Ile Asp His Ile Leu Glu Ala Gln Gln Lys
    275                 280                 285

Gly Glu Ile Asn Glu Asp Asn Val Leu Tyr Ile Val Glu Asn Ile Asn
290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Lys Leu Arg Asp Glu Ile
                325                 330                 335

Asp Thr Ile Leu Gly Pro Gly Val Gln Val Thr Glu Pro Asp Thr His
                340                 345                 350

Lys Leu Pro Tyr Leu Gln Ala Val Ile Lys Glu Thr Leu Arg Leu Arg
            355                 360                 365

Met Ala Ile Pro Leu Leu Val Pro His Met Asn Leu His Asp Ala Lys
            370                 375                 380

Leu Asn Gly Tyr Asp Ile Pro Ala Glu Ser Lys Ile Leu Val Asn Ala
385                 390                 395                 400

Trp Trp Leu Ala Asn Asn Pro Ala Gln Trp Lys Asn Pro Glu Glu Phe
                405                 410                 415

Arg Pro Glu Arg Phe Leu Glu Glu Ala Lys Val Glu Ala Asn Gly
                420                 425                 430

Asn Asp Phe Arg Tyr Leu Pro Phe Gly Val Gly Arg Arg Ser Cys Pro
            435                 440                 445

Gly Ile Ile Leu Ala Leu Pro Ile Leu Gly Ile Thr Leu Gly Arg Leu
    450                 455                 460

Val Gln Asn Phe Glu Leu Leu Pro Pro Gly Gln Ser Lys Leu Asp
465                 470                 475                 480

Thr Ser Glu Lys Gly Gly Gln Phe Ser Leu His Ile Leu Lys His Ser
            485                 490                 495

Thr Ile Val Met Lys Pro Arg Ser Phe
            500                 505

<210> SEQ ID NO 31
<211> LENGTH: 505
<212> TYPE: PRT
<213> ORGANISM: Catharanthus roseus

<400> SEQUENCE: 31

Met Asp Leu Leu Leu Leu Glu Lys Thr Leu Leu Gly Leu Phe Ala Ala
1               5                   10                  15

Ile Ile Val Ala Ser Ile Val Ser Lys Leu Arg Gly Lys Lys Phe Lys
                20                  25                  30

Leu Pro Pro Gly Pro Ile Pro Val Pro Val Phe Gly Asn Trp Leu Gln
            35                  40                  45

Val Gly Asp Asp Leu Asn His Arg Asn Leu Ser Asp Tyr Ala Lys Lys
        50                  55                  60

Phe Gly Glu Ile Phe Leu Leu Arg Met Gly Gln Arg Asn Leu Val Val
65                  70                  75                  80

Val Ser Ser Pro Glu Leu Ala Lys Glu Val Leu His Thr Gln Gly Val
```

-continued

```
             85                  90                  95
Glu Phe Gly Ser Arg Thr Arg Asn Val Val Phe Asp Ile Phe Thr Gly
            100                 105                 110
Lys Gly Gln Asp Met Val Phe Thr Val Tyr Gly Glu His Trp Arg Lys
            115                 120                 125
Met Arg Arg Ile Met Thr Val Pro Phe Phe Thr Asn Lys Val Val Gln
            130                 135                 140
Gln Tyr Arg Tyr Gly Trp Glu Glu Ala Ala Arg Val Val Glu Asp
145                 150                 155                 160
Val Lys Lys Asn Pro Glu Ser Ala Thr Asn Gly Ile Val Leu Arg Arg
            165                 170                 175
Arg Leu Gln Leu Met Met Tyr Asn Asn Met Tyr Arg Ile Met Phe Asp
            180                 185                 190
Arg Arg Phe Glu Ser Glu Asp Asp Pro Leu Phe Val Lys Leu Lys Ala
            195                 200                 205
Leu Asn Gly Glu Arg Ser Arg Leu Ala Gln Gly Phe Glu Tyr Asn Tyr
            210                 215                 220
Gly Asp Phe Ile Pro Ile Leu Arg Pro Phe Leu Arg Gly Tyr Leu Arg
225                 230                 235                 240
Ile Cys Lys Glu Val Lys Glu Arg Arg Leu Gln Leu Phe Lys Asp Tyr
            245                 250                 255
Phe Val Asp Glu Arg Lys Lys Phe Gly Ser Thr Lys Ser Met Asp Asn
            260                 265                 270
Asn Ser Leu Lys Cys Ala Ile Asp His Ile Leu Glu Ala Gln Gln Lys
            275                 280                 285
Gly Glu Ile Asn Glu Asp Asn Val Leu Tyr Ile Val Glu Asn Ile Asn
            290                 295                 300
Val Ala Ala Ile Glu Thr Thr Leu Trp Ser Ile Glu Trp Gly Ile Ala
305                 310                 315                 320
Glu Leu Val Asn His Pro Glu Ile Gln Lys Lys Leu Arg Asp Glu Leu
            325                 330                 335
Glu Thr Val Leu Gly Pro Gly Val Gln Ile Thr Glu Pro Asp Thr Tyr
            340                 345                 350
Lys Leu Pro Tyr Leu Gln Ala Val Ile Lys Glu Thr Leu Arg Leu Arg
            355                 360                 365
Met Ala Ile Pro Leu Phe Leu Pro His Met Asn Leu His Asp Ala Lys
            370                 375                 380
Leu Gly Gly Tyr Asp Ile Pro Ala Glu Ser Lys Ile Leu Val Asn Ala
385                 390                 395                 400
Trp Phe Leu Ala Asn Asn Pro Glu His Trp Lys Lys Pro Glu Glu Phe
            405                 410                 415
Arg Pro Glu Arg Phe Leu Glu Glu Ser Lys Val Glu Ala Asn Gly
            420                 425                 430
Asn Asp Phe Arg Tyr Leu Pro Phe Gly Val Gly Arg Arg Ser Cys Pro
            435                 440                 445
Gly Ile Ile Leu Ala Leu Pro Ile Leu Gly Ile Thr Ile Gly Arg Leu
            450                 455                 460
Val Gln Asn Phe Glu Leu Leu Pro Pro Gly Lys Ser Lys Ile Asp
465                 470                 475                 480
Thr Ser Glu Lys Gly Gly Gln Phe Ser Leu His Ile Leu Lys His Ser
            485                 490                 495
Thr Ile Val Leu Lys Pro Arg Thr Phe
            500                 505
```

<210> SEQ ID NO 32
<211> LENGTH: 505
<212> TYPE: PRT
<213> ORGANISM: Gossypium arboreum

<400> SEQUENCE: 32

```
Met Asp Leu Leu Phe Leu Glu Lys Val Leu Ile Ser Leu Phe Phe Thr
1               5                   10                  15

Ile Ile Phe Ala Ile Leu Val Ser Lys Leu Arg Gly Lys Arg Phe Lys
            20                  25                  30

Leu Pro Pro Gly Pro Leu Pro Ile Pro Val Phe Gly Asn Trp Leu Gln
        35                  40                  45

Val Gly Asp Asp Leu Asn His Arg Asn Leu Thr Asp Leu Ala Lys Lys
    50                  55                  60

Phe Gly Asp Ile Phe Leu Leu Arg Met Gly Gln Arg Asn Leu Val Val
65                  70                  75                  80

Ile Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Tyr Arg His Gly Trp Glu Asp Glu Ala Ala Ser Val Val Glu Asp
145                 150                 155                 160

Val Lys Lys Asn Pro Glu Ala Ala Thr Asn Gly Ile Val Leu Arg Arg
                165                 170                 175

Lys Leu Gln Leu Met Met Tyr Asn Asn Met Tyr Arg Ile Met Phe Asp
            180                 185                 190

Arg Arg Phe Glu Ser Glu Asp Asp Pro Leu Phe Val Lys Leu Lys Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Lys
225                 230                 235                 240

Leu Cys Lys Glu Val Lys Glu Ile Arg Leu Gln Leu Phe Arg Asp Gln
                245                 250                 255

Phe Leu Glu Glu Arg Lys Lys Leu Ala Thr Thr Lys Arg Ile Asp Asn
            260                 265                 270

Asn Ala Leu Lys Cys Ala Ile Asp His Ile Leu Asp Ala Gln Arg Lys
        275                 280                 285

Gly Glu Ile Asn Glu Asp Asn Val Leu Tyr Ile Val Glu Asn Ile Asn
    290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Gln Lys Leu Arg Asn Glu Ile
                325                 330                 335

Asp Thr Val Leu Gly Pro Gly Val Gln Val Thr Glu Pro Asp Thr His
            340                 345                 350

Lys Leu Pro Tyr Leu Gln Ala Val Ile Lys Glu Thr Leu Arg Leu Arg
        355                 360                 365

Met Ala Ile Pro Leu Leu Val Pro His Met Asn Leu His Asp Ala Lys
```

```
                  370                 375                 380
Leu Gly Gly Tyr Asp Ile Pro Ala Glu Ser Lys Ile Leu Val Asn Ala
385                 390                 395                 400

Trp Trp Leu Ala Asn Asn Pro Ala His Trp Lys Asn Pro Glu Glu Phe
                405                 410                 415

Arg Pro Glu Arg Phe Glu Glu Ser Lys Val Glu Ala Asn Gly
                420                 425                 430

Asn Asp Phe Arg Tyr Leu Pro Phe Gly Val Gly Arg Ser Cys Pro
                435                 440                 445

Gly Ile Ile Leu Ala Leu Pro Ile Leu Gly Ile Thr Leu Gly Arg Leu
450                 455                 460

Val Gln Asn Phe Glu Leu Leu Pro Pro Lys Gly Gln Ser Lys Leu Asp
465                 470                 475                 480

Thr Ser Glu Lys Gly Gly Gln Phe Ser Leu His Ile Leu Lys His Ser
                485                 490                 495

Thr Ile Val Ala Lys Pro Arg Val Phe
                500                 505

<210> SEQ ID NO 33
<211> LENGTH: 505
<212> TYPE: PRT
<213> ORGANISM: Glycyrrhiza echinata

<400> SEQUENCE: 33

Met Asp Leu Leu Leu Glu Lys Thr Leu Gly Leu Phe Ile Ala
1               5                   10                  15

Ala Ile Thr Ala Ile Ala Ile Ser Lys Leu Arg Gly Arg Arg Phe Lys
                20                  25                  30

Leu Pro Pro Gly Pro Ile Pro Val Pro Ile Phe Gly Asn Trp Leu Gln
                35                  40                  45

Val Gly Asp Asp Leu Asn His Arg Asn Leu Thr Asp Leu Ala Lys Arg
50                  55                  60

Phe Gly Asp Ile Phe Leu Leu Arg Met Gly Gln Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
                100                 105                 110

Lys Gly Gln Asp Met Val Phe Thr Val Tyr Gly Glu His Trp Arg Lys
                115                 120                 125

Met Arg Arg Ile Met Thr Val Pro Phe Phe Thr Asn Lys Val Val Gln
                130                 135                 140

Gln Tyr Arg Phe Gly Trp Glu Ser Glu Ala Ala Ser Val Val Asp Asp
145                 150                 155                 160

Val Arg Arg Asn Pro Asp Ala Ala Ala Gly Gly Ile Val Leu Arg Arg
                165                 170                 175

Arg Leu Gln Leu Met Met Tyr Asn Asn Met Tyr Arg Ile Met Phe Asp
                180                 185                 190

Arg Arg Phe Glu Ser Glu Glu Asp Pro Leu Phe Val Lys Leu Lys Ala
                195                 200                 205

Leu Asn Gly Glu Arg Ser Arg Leu Ala Gln Ser Phe Glu Tyr Asn Tyr
                210                 215                 220

Gly Asp Phe Ile Pro Ile Leu Arg Pro Phe Leu Lys Gly Tyr Leu Lys
225                 230                 235                 240
```

```
Ile Cys Lys Glu Val Lys Glu Arg Arg Leu Lys Leu Phe Lys Asp Tyr
            245                 250                 255

Phe Val Asp Glu Arg Met Lys Leu Glu Ser Thr Lys Ser Thr Ser Asn
            260                 265                 270

Glu Gly Leu Lys Cys Ala Ile Asp His Ile Leu Asp Ala Gln Lys Lys
            275                 280                 285

Gly Glu Ile Asn Glu Asp Asn Val Leu Tyr Ile Val Glu Asn Ile Asn
290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Lys Val Arg Asp Glu Ile
            325                 330                 335

Asp Arg Val Leu Gly Pro Gly His Gln Val Thr Glu Pro Asp Met Gln
            340                 345                 350

Lys Leu Pro Tyr Leu Gln Ala Val Ile Lys Glu Thr Leu Arg Leu Arg
            355                 360                 365

Met Ala Ile Pro Leu Leu Val Pro His Met Asn Leu His Asp Ala Lys
            370                 375                 380

Leu Gly Gly Tyr Asp Ile Pro Ala Glu Ser Lys Ile Leu Val Asn Ala
385                 390                 395                 400

Trp Trp Leu Ala Asn Asn Pro Ala Asn Trp Lys Arg Pro Glu Glu Phe
            405                 410                 415

Arg Pro Glu Arg Phe Leu Glu Glu Ser His Val Glu Ala Asn Gly
            420                 425                 430

Asn Asp Phe Arg Tyr Leu Pro Phe Gly Val Gly Arg Arg Ser Cys Pro
            435                 440                 445

Gly Ile Ile Leu Ala Leu Pro Ile Leu Gly Ile Thr Leu Gly Arg Leu
            450                 455                 460

Val Gln Asn Phe Glu Leu Leu Pro Pro Gly Gln Ser Lys Leu Asp
465                 470                 475                 480

Thr Ala Glu Lys Gly Gly Gln Phe Ser Leu His Ile Leu Lys His Ser
            485                 490                 495

Thr Ile Val Ala Lys Pro Arg Ser Phe
            500                 505

<210> SEQ ID NO 34
<211> LENGTH: 505
<212> TYPE: PRT
<213> ORGANISM: Populus x generosa

<400> SEQUENCE: 34

Met Asp Leu Leu Leu Glu Lys Thr Leu Leu Gly Ser Phe Val Ala
1               5                   10                  15

Ile Leu Val Ala Ile Leu Val Ser Lys Leu Arg Gly Lys Arg Phe Lys
            20                  25                  30

Leu Pro Pro Gly Pro Ile Pro Val Pro Val Phe Gly Asn Trp Leu Gln
            35                  40                  45

Val Gly Asp Asp Leu Asn His Arg Asn Leu Thr Asp Leu Ala Lys Lys
            50                  55                  60

Phe Gly Asp Ile Phe Leu Leu Arg Met Gly Gln Arg Asn Leu Val Val
65                  70                  75                  80

Val Ser Ser Pro Asp Leu Ser Lys Glu Val Leu His Thr Gln Gly Val
            85                  90                  95

Glu Phe Gly Ser Arg Thr Arg Asn Val Val Phe Asp Ile Phe Thr Gly
            100                 105                 110
```

-continued

```
Lys Gly Gln Asp Met Val Phe Thr Val Tyr Gly Glu His Trp Arg Lys
            115                 120                 125
Met Arg Arg Ile Met Thr Val Pro Phe Phe Thr Asn Lys Val Val Gln
130                 135                 140
Gln Tyr Arg Tyr Gly Trp Glu Glu Glu Ala Ala Gln Val Val Glu Asp
145                 150                 155                 160
Val Lys Lys Asn Pro Glu Ala Ala Thr Asn Gly Ile Val Leu Arg Arg
                165                 170                 175
Arg Leu Gln Leu Met Met Tyr Asn Asn Met Tyr Arg Ile Met Phe Asp
            180                 185                 190
Arg Arg Phe Glu Ser Glu Asp Asp Pro Leu Phe Asn Lys Leu Lys Ala
        195                 200                 205
Leu Asn Gly Glu Arg Ser Arg Leu Ala Gln Ser Phe Asp Tyr Asn Tyr
    210                 215                 220
Gly Asp Phe Ile Pro Ile Leu Arg Pro Phe Leu Arg Gly Tyr Leu Lys
225                 230                 235                 240
Ile Cys Gln Glu Val Lys Glu Arg Arg Leu Gln Leu Phe Lys Asp Tyr
                245                 250                 255
Phe Val Asp Glu Arg Lys Lys Leu Ala Ser Thr Lys Asn Met Ser Asn
            260                 265                 270
Glu Gly Leu Lys Cys Ala Ile Asp His Ile Leu Asp Ala Gln Lys Lys
        275                 280                 285
Gly Glu Ile Asn Glu Asp Asn Val Leu Tyr Ile Val Glu Asn Ile Asn
    290                 295                 300
Val Ala Ala Ile Glu Thr Thr Leu Trp Ser Ile Glu Trp Gly Ile Ala
305                 310                 315                 320
Glu Leu Val Asn His Pro Glu Ile Gln Lys Lys Leu Arg His Glu Leu
                325                 330                 335
Asp Thr Leu Leu Gly Pro Gly His Gln Ile Thr Glu Pro Asp Thr Tyr
            340                 345                 350
Lys Leu Pro Tyr Leu Asn Ala Val Ile Lys Glu Thr Leu Arg Leu Arg
        355                 360                 365
Met Ala Ile Pro Leu Leu Val Pro His Met Asn Leu His Asp Ala Lys
    370                 375                 380
Leu Gly Gly Phe Asp Ile Pro Ala Glu Ser Lys Ile Leu Val Asn Ala
385                 390                 395                 400
Trp Trp Leu Ala Asn Asn Pro Ala His Trp Lys Asn Pro Glu Glu Phe
                405                 410                 415
Arg Pro Glu Arg Phe Leu Glu Glu Ala Lys Val Glu Ala Asn Gly
            420                 425                 430
Asn Asp Phe Arg Tyr Leu Pro Phe Gly Val Gly Arg Ser Cys Pro
        435                 440                 445
Gly Ile Ile Leu Ala Leu Pro Ile Leu Gly Ile Thr Leu Gly Arg Leu
    450                 455                 460
Val Gln Asn Phe Glu Leu Leu Pro Pro Pro Gly Gln Ser Lys Ile Asp
465                 470                 475                 480
Thr Ala Glu Lys Gly Gly Gln Phe Ser Leu His Ile Leu Lys His Ser
                485                 490                 495
Thr Ile Val Ala Lys Pro Arg Ser Phe
            500                 505
```

CINNAMIC ACID 4-HYDROXYLASE

This application claims the benefit under 35 USC §119(c) of U.S. provisional application Ser. No. 60/690,154, filed on Jun. 14, 2005 which is incorporated herein by reference in its entirety.

FIELD OF THE INVENTION

The invention related to a novel cinnamic acid 4-hydroxylase gene and protein from potato and uses thereof.

BACKGROUND OF THE INVENTION

After-cooking darkening (ACD) is a non-enzymatic gray-black discoloration of potato tuber flesh occurring after cooking. The discoloration is due to the formation of a colorless iron-chlorogenic acid complex during the cooking process, which upon exposure to air, oxidizes to form the dark ferri-dichlorogenic acid (Dale and Mackay, 1994). To prevent the discoloration caused by ACD, processors in the French fry industry treat the French fried potato strips with sodium acid pyrophosphate (SAPP, $Na_2H_2P_2O_7$). Sodium acid pyrophosphate reduces darkening by complexing with the iron in the tuber. In this capacity the iron is held in a nonionizable form and cannot take part in the reaction with chlorogenic acid (Smith, 1987). A rise in the number of French fry processing industries has led to an increase in SAPP usage. The phosphorus residue released from SAPP during processing, has made it mandatory to eliminate SAPP from industrial wastewater. This currently involves the removal of phosphorous from wastewater through chemical precipitation, adding further to processing costs for the French fry industry (Wang-Pruski and Nowak, 2004). Considering the millions of dollars per year that SAPP costs the industry, it would be beneficial both from economical and environmental standpoints to reduce or eliminate the use of SAPP in the processing industry.

Traditional breeding has led to the development of many low-ACD cultivars, including the cultivars Red Pontiac and Yukon Gold. However, cultivars for French fry production must also possess traits essential for processing, specifically oblong tuber shape, shallow eyes, high specific gravity, low reducing sugars, high yield, and resistance to diseases (Bradshaw et al., 1998). Currently, Russet Burbank and Shepody are the primary cultivars used in the French fry processing industry in Canada. Both cultivars require the use of SAPP to prevent the darkening. To date no cultivars are available that possess all the traits essential for French fry processing, as well as complete resistance to ACD (Wang-Pruski, personal communication).

Chlorogenic acid (CgA) is not only involved in ACD but it also has various biological roles, including the involvement in defense mechanisms against insects or phytopathogens, disease and fungal resistance, growth regulation, and wound response (Kühnl et al., 1987; Yao et al., 1995; Friedman, 1997; Griffiths and Bain, 1997). In potatoes specifically, CgA is able to provide covalent cross-links between polysaccharides and cell well proteins; making the cell wall stronger and more resistant to invading pathogens (Yao et al., 1995). Once the threat (pathogen or disease) subsides, normal oxidative processes lower the accumulated CgA in suberized tissues (Friedman, 1997). Chlorogenic acid accounts for up to 90% of the total phenolic compounds present in the potato tuber (Griffiths and Bain, 1997; Lewis et al., 1998; Lugasi et al., 1999; Percival and Baird, 2000). Approximately 50% of the CgA is located in the potato peel and adjoining tissues. Chlorogenic acid is synthesized via the phenylpropanoid pathway, which has not been explored in great detail, especially in species from the Solanaceae family.

Cinnamic acid 4-hydroxylase (C4H, EC 1.14.13.11) is an essential enzyme for the biosynthesis of CgA and therefore is thought to play a key role in the ACD mechanism. Cinnamic acid 4-hydroxylase catalyzes the hydroxylation of t-cinnamic acid to form p-coumaric acid, during the synthesis of CA. The C4H enzyme belongs to the CYP73 family of plant cytochrome P450 proteins. C4H enzymatic activity is induced by wounding, light, and pathogen infection in various plant species (Tanaka et al., 1974; Fahrendorf and Dixon, 1993; Bell-Lelong et al., 1997; Petersen, 2003). Class I and II forms of the gene encoding C4H have been sequenced in many plant species, including *Arabidopsis*, Jerusalem artichoke, red pepper, pea, alfalfa, and species of *Populus* and *Citrus*. Class I c4h is the predominate form found in almost all plant species, whereas the divergent class II form has only been isolated from orange and French bean. The divergent class II c4h has approximately 60% sequence similarity to the class I form and differs in the N-terminus and three internal domains (Betz et al., 2001; Blee et al., 2001).

The gene expression level of c4h depends on the specific plant species, tissue type, as well as stress and environmental factors (Whitbred and Schuler, 2000). Bell-Lelong et al. (1997) and Mizutani et al. (1997) found that in *Arabidopsis*, c4h was expressed in all tissues analyzed including leaves, seedlings, stems, flowers, and roots. The higher levels were found in the stems and roots, possibly because of C4H's role in the production of the monolignols required for lignification. The c4h gene has not been sequenced nor has its expression profile been identified in potato. To date, no genes in potato have been identified that relate to the control of ACD.

SUMMARY OF THE INVENTION

The present invention relates to a nucleic acid sequence that encodes cinnamic acid 4-hydroxylase (C4H) from potato. The full length genomic DNA and cDNA of the gene for the enzyme are identified. Further, its gene function at gene expression levels of this enzyme in potato has been confirmed to affect the chlorogenic acid biosynthesis in potato tubers. Its expression level is also correlated with the degree of the darkness in potatoes, the negative trait of after-cooking darkening (ACD) affecting the quality of table stock and processing varieties.

Accordingly, the present invention provides an isolated nucleic acid molecule comprising a sequence encoding the C4H enzyme. The invention includes both the genomic DNA and cDNA sequence of the C4H gene. The invention also includes the corresponding polypeptide, C4H.

In one embodiment, the purified and isolated nucleic acid molecule comprises (a) a nucleic acid sequence encoding a protein as shown in Table 4 (SEQ ID No. 2);

(b) a nucleic acid sequence complementary to (a);

(c) a nucleic acid sequence that has substantial homology to (a) or (b);

(d) a nucleic acid sequence that is an analog to a nucleic acid sequence of (a), (b), or (c);

(e) a fragment of (a) to (d) that is at least 15 bases, preferably 20 to 30 bases, and which will hybridize to a nucleic acid sequence of (a), (b), (c) or (d) under stringent hybridization conditions; or (f) a nucleic acid molecule differing from any of the nucleic acids of (a) to (c) in codon sequences due to the degeneracy of the genetic code.

In a specific embodiment of the invention, an isolated nucleic acid molecule is provided having a sequence as shown in Table 3 (SEQ ID No. 1) or a fragment or variant thereof.

The present invention also includes the isolated C4H protein of the invention. In a preferred embodiment, the C4H protein has the amino acid sequence shown in Table 4 (SEQ ID. NO. 2) or a fragment or variant thereof.

The present invention also includes methods of modulating C4H gene or protein expression or activity comprising administering a modulator of the C4H gene or protein to a cell or plant in need thereof.

In one embodiment, the present invention provides a method of enhancing C4H gene expression comprising administering an effective amount an agent that can enhance the expression or activity of the C4H gene or protein. Methods of enhancing the C4H gene expression can be used in enhancing disease resistance to pathogens as well as enhancing the nutritional value of foods.

In another embodiment, the present invention provides a method of decreasing C4H gene expression or activity comprising administering an effective amount of a C4H inhibitor to a cell or animal in need thereof. Methods of inhibiting C4H gene expression or C4H protein activity can be useful in reducing after-cooking darkening of food.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
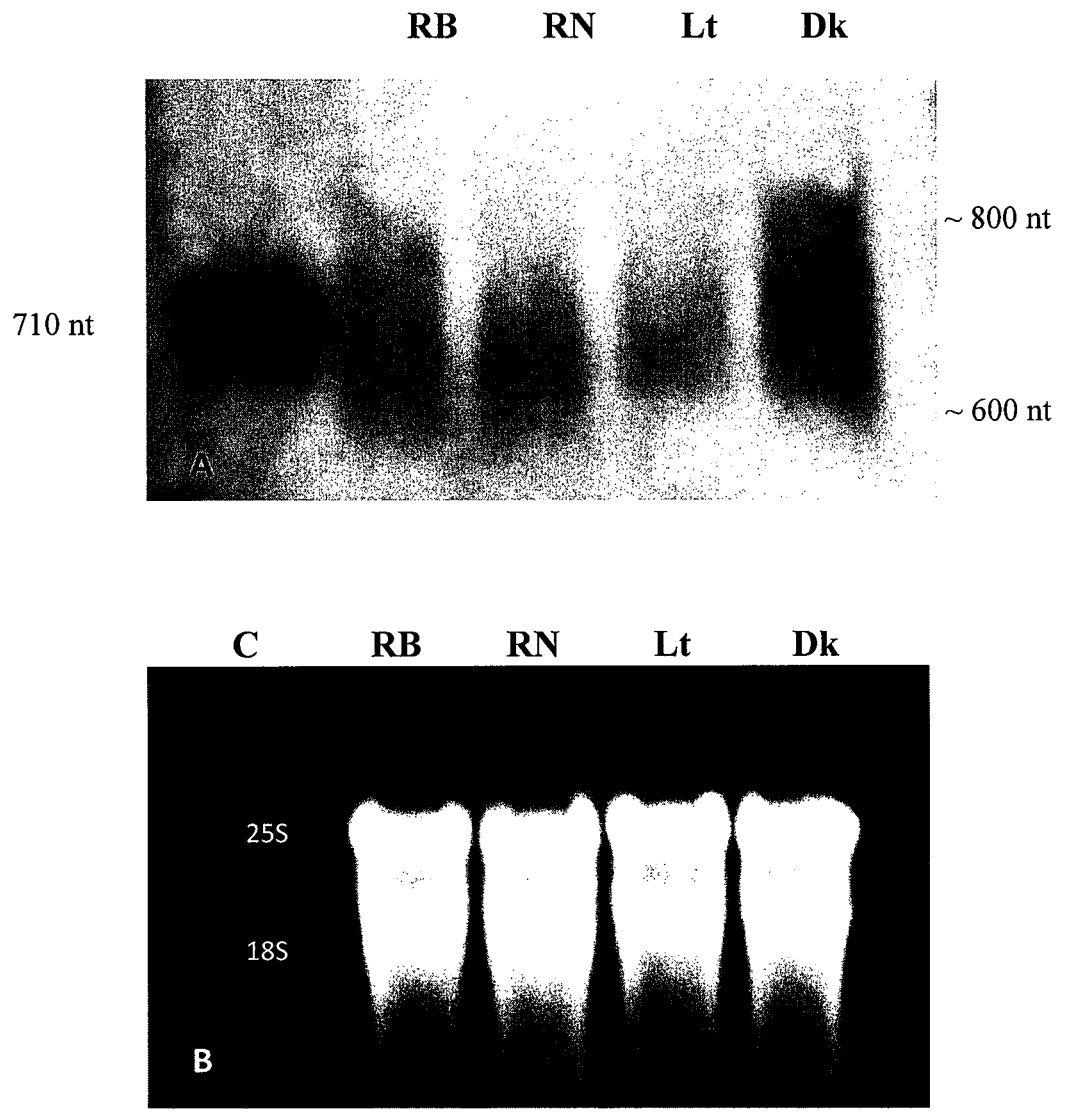
FIG. 1: Northern hybridization analysis of c4h expression in Russet Burbank (RB), Russet Norkotah (RN), light-ACD diploid (Lt), and dark-ACD diploid (Dk). A. Hybridization signals from one of the three replicates using the 472 bp c4h probe. B. The corresponding total RNA separated by formaldehyde agarose (0.7%) gel electrophoresis.

The present invention relates to a DNA sequence that encodes cinnamic acid 4-hydroxylase (C4H) from potato. The full length genomic DNA and cDNA of the gene for the enzyme are identified. Further, its gene function at gene expression levels of this enzyme in potato has been confirmed to affect the chlorogenic acid biosynthesis in potato tubers. Its expression level is also correlated with the degree of the darkness in potatoes, the negative trait named as after-cooking darkening (ACD) affecting the quality of table stock and processing varieties.

I. Nucleic Acid Molecules of the Invention

As hereinbefore mentioned, the present invention relates to isolated C4H nucleic acid molecules. The term "isolated" refers to a nucleic acid substantially free of cellular material or culture medium when produced by recombinant DNA techniques, or chemical precursors, or other chemicals when chemically synthesized.

The term "nucleic acid" is intended to include DNA and RNA and can be either double stranded or single stranded. The term is also intended to include a strand that is a mixture of nucleic acid molecules and nucleic acid analogs and/or nucleotide analogs, or that is made entirely of nucleic acid analogs and/or nucleotide analogs.

Broadly stated, the present invention provides an isolated nucleic acid molecule encoding the C4H protein. Accordingly, the present invention provides an isolated nucleic acid molecule containing a sequence encoding C4H shown in Table 4 or a fragment, variant, or analog thereof.

In one embodiment, the purified and isolated nucleic acid molecule comprises (a) a nucleic acid sequence encoding a C4H protein as shown in Table 4 (SEQ ID No. 2);

(b) a nucleic acid sequence complementary to (a);

(c) a nucleic acid sequence that has substantial homology to (a) or (b);

(d) a nucleic acid sequence that is an analog to a nucleic acid sequence of (a), (b), or (c);

(e) a fragment of (a) to (d) that is at least 15 bases, preferably 20 to 30 bases, and which will hybridize to a nucleic acid sequence of (a), (b), (c) or (d) under stringent hybridization conditions; or (f) a nucleic acid molecule differing from any of the nucleic acids of (a) to (c) in codon sequences due to the degeneracy of the genetic code.

In a specific embodiment of the invention, the isolated nucleic acid molecule has a sequence as shown in Table 3 (SEQ ID No. 1) or a fragment or variant thereof.

The term "C4H" means cinnamic acid 4-hydroxylase and includes the nucleic acid sequence as shown in Table 3 (SEQ ID No. 1) or the protein having the amino acid sequence shown in Table 4 (SEQ ID No. 2) as well as mutations, variants and fragments thereof that can catalyze the hydroxylation of t-cinnamic acid to p-coumaric acid during the synthesis of chlorogenic acid.

It will be appreciated that the invention includes nucleic acid molecules encoding truncations of the C4H proteins of the invention, and analogs and homologs of the C4H proteins of the invention and truncations thereof, as described below.

Further, it will be appreciated that the invention includes nucleic acid molecules comprising nucleic acid sequences having substantial sequence homology with the nucleic acid sequences of the invention and fragments thereof. The term "sequences having substantial sequence homology" means those nucleic acid sequences which have slight or inconsequential sequence variations from these sequences, i.e. the sequences function in substantially the same manner to produce functionally equivalent proteins. The variations may be attributable to local mutations or structural modifications.

Generally, nucleic acid sequences having substantial homology include nucleic acid sequences having at least 70%, preferably 80-90% identity with the nucleic acid sequences of the invention.

Sequence identity is most preferably assessed by the algorithm of the BLAST version 2.1 program advanced search (BLAST is a series of programs that are available online at http://www.ncbi.nlm.nih.gov/BLAST. The advanced blast search (http://www.ncbi.nlm.nih.gov/blast/blast.cgi?Jform=1) is set to default parameters. (ie Matrix BLOSUM62; Gap existence cost 11; Per residue gap cost 1; Lambda ratio 0.85 default).). For example, if a nucleotide sequence (called "Sequence A") has 90% identity to a portion of the nucleotide sequence in Table 3, then Sequence A will be identical to the referenced portion of the nucleotide sequence in Table 3, except that Sequence A may include up to 10 point mutations, such as substitutions with other nucleotides, per each 100 nucleotides of the referenced portion of the nucleotide sequence in Table 3. Nucleotide sequences functionally equivalent to the C4H transcript can occur in a variety of forms as described below.

The term "a nucleic acid sequence which is an analog" means a nucleic acid sequence which has been modified as compared to the sequence of (a), (b) or (c) wherein the modification does not alter the utility of the sequence as described herein. The modified sequence or analog may have improved properties over the sequence shown in (a), (b) or (c). One example of a modification to prepare an analog is to replace one of the naturally occurring bases (i.e. adenine, guanine, cytosine or thymidine) of the sequence shown in Table I, with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in Table 3. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complementary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506).

Another aspect of the invention provides a nucleic acid molecule, and fragments thereof having at least 15 bases, which hybridizes to the nucleic acid molecules of the invention under hybridization conditions. Such nucleic acid molecules preferably hybridize to all or a portion of C4H or its complement under stringent conditions as defined herein (see Sambrook et al. (most recent edition) Molecular Cloning: A Laboratory Manual, Cold Spring Harbor Laboratory Press, Cold Spring Harbor, N.Y.; Ausubel et al. (eds.), 1995, Current Protocols in Molecular Biology, (John Wiley & Sons, NY)). The portion of the hybridizing nucleic acids is typically at least 15 (e.g. 20, 25, 30 or 50) nucleotides in length. The hybridizing portion of the hybridizing nucleic acid is at least 80% e.g. at least 95% or at least 98% identical to the sequence or a portion or all of a nucleic acid encoding a C4H polypeptide, or its complement. Hybridizing nucleic acids of the type described herein can be used, for example, as a cloning probe, a primer (e.g. a PCR primer) or a diagnostic probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g. SSC or SSPE). Then, assuming that 1% mismatching results in a 1 degree Celsius decrease in the Tm, the temperature of the final wash in the hybridization reaction is reduced accordingly (for example, if sequences having greater than 95% identity with the probe are sought, the final wash temperature is decreased by 5 degrees Celsius). In practice, the change in Tm can be between 0.5 degrees Celsius and 1.5 degrees Celsius per 1% mismatch. Low stringency conditions involve hybridizing at about: 1×SSC, 0.1% SDS at 65° C. High stringency conditions are: 0.1×SSC, 0.1% SDS at 65° C. Moderate stringency is about 1×SSC 0.1% SDS at 60 degrees Celsius. The parameters of salt concentration and temperature can be varied to achieve the optimal level of identity between the probe and the target nucleic acid.

Isolated and purified nucleic acid molecules having sequences which differ from the nucleic acid sequence shown in Table 3 due to degeneracy in the genetic code are also within the scope of the invention. The genetic code is degenerate so other nucleic acid molecules, which encode a polypeptide identical to the C4H amino acid sequence (Table 4) may also be used.

Nucleic acid molecules from C4H can be isolated by preparing a labelled nucleic acid probe based on all or part of the nucleic acid sequences as shown in Table 3, and using this labelled nucleic acid probe to screen an appropriate DNA library (e.g. a cDNA or genomic DNA library). Nucleic acids isolated by screening of a cDNA or genomic DNA library can be sequenced by standard techniques. Another method involves comparing the C4H sequence to other sequences, for example using bioinformatics techniques such as database searches or alignment strategies, and detecting the presence of a C4H nucleic acid sequence.

Nucleic acid molecules of the invention can also be isolated by selectively amplifying a nucleic acid using the polymerase chain reaction (PCR) methods and cDNA or genomic DNA. It is possible to design synthetic oligonucleotide primers from the nucleic acid molecules as shown in Table 3 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes the C4H protein. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably a nucleic acid sequence shown in Table 3 may be inverted relative to its normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

II. Novel Proteins of the Invention

The invention further includes an isolated C4H protein encoded by the nucleic acid molecules of the invention. Within the context of the present invention, a protein of the invention may include various structural forms of the primary protein which retain biological activity.

Broadly stated, the present invention provides an isolated C4H protein from potatoes.

In a preferred embodiment of the invention, the C4H protein has the amino acid sequence as shown in Table 4 (SEQ ID No. 2) or a fragment or variant thereof.

In addition to full length amino acid sequences, the proteins of the present invention also include truncations of the protein, and analogs, and homologs of the protein and truncations thereof as described herein. Truncated proteins may comprise peptides of at least fifteen amino acid residues.

Analogs or variants of the protein having the amino acid sequence shown in Table 4 and/or truncations thereof as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequence shown in Table 4. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequence shown in Table 4. The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

A homologous protein includes a protein with an amino acid sequence having at least 70%, preferably 80-90%, most preferably 95% identity with the amino acid sequence as shown in Table 4. As with the nucleic acid molecules of the invention, identity is calculated according to methods known in the art. Sequence identity is most preferably assessed by the algorithm of BLAST version 2.1 advanced search. BLAST is a series of programs that are available online at http://www.ncbi.nlm.nih.gov/BLAST. The advanced blast search (http://www.ncbi.nlm.nih.gov/blast/blast.cgi?Jform=1) is set to default parameters (i.e. Matrix BLOSUM62, Gap existence cost 11; Per residue gap cost 1; Lambda ration 0.85 default).

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising the nucleotides as shown in Table 3. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418, hygromycin and kanamycin which confer resistance to certain drugs, β-galactosidase, chloramphenicol acetyltransferase, firefly luciferase or green fluorescence protein (GFP). Transcription of the selectable marker gene is monitored by changes in the concentration of the selectable marker protein such as β-galactosidase, chloramphenicol acetyltransferase, firefly luciferase or green fluorescence protein (GFP). If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Methodologies to introduce plant recombinant expression vectors into a plant cell, also referred to herein as "transformation", are well known to the art and typically vary depending on the plant cell that is selected. General techniques to introduce recombinant expression vectors in cells include, electroporation; chemically mediated techniques, for example $CaCl_2$ mediated nucleic acid uptake; particle bombardment (biolistics); the use of naturally infective nucleic acid sequences, for example virally derived nucleic acid sequences, or *Agrobacterium* or *Rhizobium* derived sequences, polyethylene glycol (PEG) mediated nucleic acid uptake, microinjection and the use of silicone carbide whiskers.

In preferred embodiments, a transformation methodology is selected which will allow the integration of the C4H nucleic acid sequence in the plant cell's genome, and preferably the plant cell's nuclear genome. In accordance herewith this is considered particularly desirable as the use of such a methodology will result in the transfer of the C4H nucleic acid sequence to progeny plants upon sexual reproduction. Transformation methods that may be used in this regard include biolistics and *Agrobacterium* mediated methods.

Transformation methodologies for dicotyledenous plant species are well known. Generally, *Agrobacterium* mediated transformation is used because of its high efficiency, as well as the general susceptibility by many, if not all, dicotyledenous plant species. *Agrobacterium* transformation generally involves the transfer of a binary vector (e.g. pGreenII0129), comprising the nucleic acid sequence of the present invention from *E. coli* to a suitable *Agrobacterium* strain (e.g. GV3101, EHA101 and LBA4404) by, for example, tri-parental mating with an *E. coli* strain carrying the recombinant binary vector and an *E. coli* strain carrying a helper plasmid capable of mobilizing the binary vector to the target *Agrobacterium* strain, or by DNA transformation of the *Agrobacterium* strain (Hofgen et al., Nucl. Acids. Res., 1988, 16:9877). Other techniques that may be used to transform dicotyledenous plant cells include biolistics (Sanford, 1988, Trends in Biotechn. 6:299-302); electroporation (Fromm et al., 1985, Proc. Natl. Acad. Sci. USA., 82:5824-5828); PEG mediated DNA uptake (Potrykus et al., 1985, Mol. Gen. Genetics, 199:169-177); microinjection (Reich et al., Bio/Techn., 1986, 4:1001-1004); and silicone carbide whiskers (Kaeppler et al., 1990, Plant Cell Rep., 9:415-418) or in planta transformation using, for example, a flower dipping methodology (Clough and Bent, 1998, Plant J., 16:735-743).

Monocotyledonous plant species may be transformed using a variety of methodologies including particle bombardment (Christou et al., 1991, Biotechn. 9:957-962; Weeks et al., Plant Physiol., 1993, 102:1077-1084; Gordon-Kamm et al., Plant Cell, 1990, 2:5603-618); PEG mediated DNA uptake (European Patents 0292 435; 0392 225) or *Agrobacterium* mediated transformation (Goto-Fumiyuki et al., 1999, Nature-Biotech. 17:282-286).

The exact plant transformation methodology may vary somewhat depending on the plant species and the plant cell type (e.g. seedling derived cell types such as hypocotyls and cotyledons or embryonic tissue) that is selected as the cell target for transformation. As hereinbefore mentioned in a particularly preferred embodiment potato is used. A methodology to obtain potato transformants is available (De Block M. 1988. Genotype-independent leaf disc transformation of potato (*Solanum tuberosum*) using *Agrobacterium tumefaciens*. Theor Appl Genet 76: 767-774)

Following transformation, the plant cells are grown and upon the emergence of differentiating tissue, such as shoots and roots, mature plants are regenerated. Typically a plurality of plants is regenerated. Methodologies to regenerate plants are generally plant species and cell type dependent and will be known to those skilled in the art. Further guidance with respect to plant tissue culture may be found in, for example: Plant Cell and Tissue Culture, 1994, Vasil and Thorpe Eds., Kluwer Academic Publishers; and in: Plant Cell Culture Protocols (Methods in Molecular Biology 111), 1999, Hall Eds, Humana Press.

The proteins of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

III. Applications

The present invention includes all uses of the nucleic acid molecule and C4H proteins of the invention including, but not limited to, the preparation of antibodies and antisense oligonucleotides, the preparation of diagnostic assays, the isolation of substances that modulate C4H expression and/or activity as well as the use of the C4H nucleic acid sequences and proteins and modulators thereof. Some of the uses are further described below.

(A) Antibodies

The isolation of the C4H protein enables the preparation of antibodies specific for C4H. Accordingly, the present invention provides an antibody that binds to a C4H protein.

Conventional methods can be used to prepare the antibodies. For example, by using a peptide of C4H, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the protein or peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for C4H as described herein.

The term "antibody" as used herein is intended to include fragments thereof which also specifically react with C4H. Antibodies can be fragmented using conventional techniques and the fragments screened for utility in the same manner as described above. For example, F(ab')2 fragments can be generated by treating antibody with pepsin. The resulting F(ab')2 fragment can be further treated to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of C4H antigens of the invention (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Nat!. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against C4H proteins may also be generated by screening expression libraries encoding immunoglobulin genes, or portions thereof, expressed in bacteria with peptides produced from the nucleic acid molecules of C4H. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a SCID-hu mouse, for example the model developed by Genpharm, can be used to produce antibodies or fragments thereof.

(B) Antisense Oligonucleotides

Isolation of a nucleic acid molecule encoding C4H enables the production of antisense oligonucleotides that can modulate the expression and/or activity of C4H.

Accordingly, the present invention provides an antisense oligonucleotide that is complementary to a nucleic acid sequence encoding C4H. In one embodiment, the nucleic acid sequence is a shown in Table 3.

The term "antisense oligonucleotide" as used herein means a nucleotide sequence that is complementary to its target.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complementary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The antisense oligonucleotides may be introduced into tissues or cells using techniques in the art including vectors (retroviral vectors, adenoviral vectors and DNA virus vectors) or physical techniques such as microinjection. The antisense oligonucleotides may be directly administered in vivo or may be used to transfect cells in vitro which are then administered in vivo.

(C) Diagnostic Assays

The present inventors have determined that there is a correlation between C4H and susceptibility to ACD, the higher the level of the C4H gene, the more susceptible the plant is to ACD.

Accordingly, the present invention provides a method of determining the susceptibility of a plant to ACD comprising assaying a sample from a plant for (a) a nucleic acid molecule encoding a C4H protein or a fragment thereof or (b) a C4H protein or a fragment thereof wherein increased levels of the C4H nucleic acid or protein indicates that the plant is more susceptible to ACD. The C4H protein preferably has the sequence shown in Table 4.

The plant sample can be from any plant, preferably a plant that demonstrates ACD. The plant is preferably an edible plant including, but not limited to, root vegetables and fruits. In one embodiment the plant is a fruit selected from apples and pears. In a preferred embodiment, the plant is the root vegetable, potato. One of skill in the art can readily determine how to prepare the samples for the assay using techniques known in the art. Details of how to prepare potato samples are provided in Example 2.

The levels of C4H in the sample will be compared to a suitable control. Suitable controls include samples from plants that are not susceptible to ACD or control samples that contain no C4H or are spiked to contain known quantities of C4H.

(i) Nucleic acid molecules

The nucleic acid molecules encoding C4H as described herein or fragments thereof, allow those skilled in the art to construct nucleotide probes and primers for use in the detection of nucleotide sequences encoding C4H or fragments thereof in plant samples.

Accordingly, the present invention provides a method for detecting a nucleic acid molecule encoding C4H in a sample comprising contacting the sample with a nucleotide probe capable of hybridizing with the nucleic acid molecule to form a hybridization product, under conditions which permit the formation of the hybridization product, and assaying for the hybridization product.

Example of probes that may be used in the above method include fragments of the nucleic acid sequences shown in Table 3 or SEQ. ID. NO.:1. A nucleotide probe may be labelled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labelled antibody, fluorescent compounds, enzymes, antibodies specific for a labelled antigen, and chemiluminescence. An appropriate label may be selected having regard to the rate of hybridization and binding of the probe to the nucleic acid to be detected and the amount of nucleic acid available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleotide probes may be used to detect genes, preferably in plant cells, that hybridize to the nucleic acid molecule of the present invention preferably, nucleic acid molecules which hybridize to the nucleic acid molecule of the invention under stringent hybridization conditions as described herein.

In one embodiment, the hybridization assay can be a Southern analysis where the sample is tested for a DNA sequence that hybridizes with a C4H specific probe. In another embodiment, the hybridization assay can be a Northern analysis where the sample is tested for an RNA sequence that hybridizes with a C4H specific probe. Southern and Northern analyses may be performed using techniques known in the art (see for example, Current Protocols in Molecular Biology, Ausubel, F. et al., eds., John Wiley & Sons).

Nucleic acid molecules encoding a C4H protein can be selectively amplified in a sample using the polymerase chain reaction (PCR) methods and cDNA or genomic DNA. It is possible to design synthetic oligonucleotide primers from the nucleotide sequence shown in Table 3, (SEQ. ID. NO.:1) for use in PCR. A nucleic acid can be amplified from cDNA or genomic DNA using oligonucleotide primers and standard PCR amplification techniques. The amplified nucleic acid can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

Samples may be screened using probes to detect the presence of a C4H gene by a variety of techniques. Genomic DNA used for the diagnosis may be obtained from cells. The DNA may be isolated and used directly for detection of a specific sequence or may be PCR amplified prior to analysis. RNA or cDNA may also be used. To detect a specific DNA sequence hybridization using specific oligonucleotides, direct DNA sequencing, restriction enzyme digest, RNase protection, chemical cleavage, and ligase-mediated detection are all methods which can be utilized. Oligonucleotides specific to mutant sequences can be chemically synthesized and labelled radioactively with isotopes, or non-radioactively using biotin tags, and hybridized to individual DNA samples immobilized on membranes or other solid-supports by dot-blot or transfer from gels after electrophoresis. The presence or absence of the C4H sequences is then visualized using methods such as autoradiography, fluorometry, or colorimetric reaction Direct DNA sequencing reveals the presence of C4H DNA. Cloned DNA segments may be used as probes to detect specific DNA segments. PCR can be used to enhance the sensitivity of this method. PCR is an enzymatic amplification directed by sequence-specific primers, and involves repeated cycles of heat denaturation of the DNA, annealing of the complementary primers and extension of the annealed primer with a DNA polymerase. This results in an exponential increase of the target DNA.

Other nucleotide sequence amplification techniques may be used, such as real-time PCR, ligation-mediated PCR, anchored PCR and enzymatic amplification as would be understood by those skilled in the art.

(ii) Proteins

The C4H protein may be detected in a sample using antibodies that bind to the protein as described in detail above. Accordingly, the present invention provides a method for detecting a C4H protein comprising contacting the sample with an antibody that binds to C4H which is capable of being detected after it becomes bound to the C4H in the sample.

Antibodies specifically reactive with C4H, or derivatives thereof, such as enzyme conjugates or labeled derivatives, may be used to detect C4H in various samples, for example they may be used in any known immunoassays which rely on the binding interaction between an antigenic determinant of C4H, and the antibodies. Examples of such assays are radioimmunoassays, enzyme immunoassays (e.g. ELISA), immunofluorescence, immunoprecipitation, latex agglutination, hemagglutination and histochemical tests. Thus, the antibodies may be used to detect and quantify C4H in a sample. In particular, the antibodies of the invention may be used in immuno-histochemical analyses, for example, at the cellular and sub-subcellular level, to detect C4H, to localise it to particular cells and tissues and to specific subcellular locations, and to quantitate the level of expression.

Cytochemical techniques known in the art for localizing antigens using light and electron microscopy may be used to detect C4H. Generally, an antibody of the invention may be labelled with a detectable substance and C4H may be localized in tissue based upon the presence of the detectable substance. Examples of detectable substances include various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine I-125, I-131 or 3-H. Antibodies may also be coupled to electron dense substances, such as ferritin or colloidal gold, which are readily visualised by electron microscopy.

Indirect methods may also be employed in which the primary antigen-antibody reaction is amplified by the introduction of a second antibody, having specificity for the antibody reactive against C4H. By way of example, if the antibody having specificity against C4H is a rabbit IgG antibody, the second antibody may be goat anti-rabbit gamma-globulin labelled with a detectable substance as described herein.

Where a radioactive label is used as a detectable substance, C4H may be localized by autoradiography. The results of autoradiography may be quantitated by determining the density of particles in the autoradiographs by various optical methods, or by counting the grains.

The ACD evaluation on the plant sample can be conducted using techniques known in the art including the methodology described in Example 2.

The inventors have also confirmed that the chlorogenic acid content in potato tubers is correlated with the degree of after-cooking darkening (ACD). Accordingly, the present invention provides a method of determining the susceptibility of a plant to ACD comprising assaying a sample from a plant for chlorogenic acid wherein increased levels of chlorogenic acid indicates that the plant is susceptible to ACD. The plant sample may be from any plant that is susceptible to ACD including edible plants such as root vegetables and fruit. Preferably the plant is potato.

(D) C4H Modulators

In addition to antibodies and antisense oligonucleotides described above, other substances that modulate C4H expression or activity may also be identified.

(i) Substances that Bind C4H

Substances that affect C4H activity can be identified based on their ability to bind to C4H.

Substances which can bind with the C4H of the invention may be identified by reacting the C4H with a substance which potentially binds to C4H, and assaying for complexes, for free substance, or for non-complexed C4H, or for activation of C4H. In particular, a yeast two hybrid assay system may be used to identify proteins which interact with C4H (Fields, S. and Song, O., 1989, Nature, 340:245-247). Systems of analysis which also may be used include ELISA.

Accordingly, the invention provides a method of identifying substances which can bind with C4H, comprising the steps of:
(a) reacting C4H and a test substance, under conditions which allow for formation of a complex between the C4H and the test substance, and
(b) assaying for complexes of C4H and the test substance, for free substance or for non complexed C4H, wherein the presence of complexes indicates that the test substance is capable of binding C4H.

The C4H protein used in the assay may have the amino acid sequence shown in Table 4 (SEQ.ID.NO.:2) or may be a fragment, analog, derivative, homolog or mimetic thereof as described herein.

Conditions which permit the formation of substance and C4H complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against C4H or the substance, or labelled C4H, or a labelled substance may be utilized. The antibodies, proteins, or substances may be labelled with a detectable substance as described above.

C4H, or the substance used in the method of the invention may be insolubilized. For example, C4H or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized protein or substance may be prepared by reacting the material with a suitable insoluble carrier using known chemical or physical methods, for example, cyanogen bromide coupling.

The proteins or substance may also be expressed on the surface of a cell using the methods described herein.

The invention also contemplates assaying for an antagonist or agonist of the action of C4H.

It will be understood that the agonists and antagonists that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of C4H. Thus, the invention may be used to assay for a substance that competes for the same binding site of C4H.

(ii) Peptide Mimetics

The present invention also includes peptide mimetics of the C4H protein of the invention. Such peptides may include competitive inhibitors, enhancers, peptide mimetics, and the like. All of these peptides as well as molecules substantially homologous, complementary or otherwise functionally or structurally equivalent to these peptides may be used for purposes of the present invention.

"Peptide mimetics" are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a peptide of the invention.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

(E) Modulating C4H Expression

The present invention also includes methods of modulating the expression and/or activity of the C4H gene or protein. Accordingly, the present invention provides a method of modulating C4H expression or activity comprising administering to a cell or plant in need thereof, an effective amount of agent that modulates C4H expression and/or activity. The present invention also provides a use of an agent that modulates C4H expression and/or activity.

The term "agent that modulates C4H expression and/or activity" or "C4H modulator" means any substance that can alter the expression and/or activity of the C4H gene or protein. Examples of agents which may be used include: a nucleic acid molecule encoding C4H; the C4H protein as well as fragments, analogs, derivatives or homologs thereof; antibodies; antisense nucleic acids; peptide mimetics; and substances isolated using the screening methods described herein.

The term "effective amount" as used herein means an amount effective, at dosages and for periods of time necessary to achieve the desired results.

The term "plant" as used herein includes all members of the plant kingdom, and is preferably an edible plant such as root vegetables or fruit. In a preferred embodiment, the plant is potato, apple or pear.

In one embodiment, the C4H modulator is an agent that enhances the expression and/or activity of the C4H gene or protein. Enhancing the expression of the C4H gene can lead to enhanced production of chlorogenic acid which is one of the major phenolic compounds in plants that is involved in plant defense functions against bacterial and viral pathogens. Enhancing C4H gene expression therefore can lead to enhanced disease resistance to these pathogens. Enhancing chlorogenic acid is also useful as it is a natural antioxidant and plants containing enhanced levels will be of greater nutritional value.

Accordingly, the present invention also provides a method of enhancing the production of chlorogenic acid comprising administering an effective amount of an agent that enhances C4H gene expression or protein activity to a cell or plant in need thereof. Agents that enhance C4H gene expression or protein activity include nucleic acid molecules encoding the C4H protein, C4H protein as well as fragments, analogs, derivatives or homologs thereof. In a specific embodiment, the C4H nucleic acid has the sequence shown in Table 3 (SEQ ID. No.1) and the C4H protein has a sequence shown in Table 4 (SEQ ID. No. 2).

In another embodiment, the C4H modulator is an agent that decreases C4H gene expression and/or C4H protein activity. Inhibiting C4H expression can be used to decrease ACD in plants as there is correlation between increased C4H levels and increased ACD in plants.

Accordingly, the present invention provides a method of decreasing ACD in plants comprising administering and effective amount of an agent that can inhibit the expression of the C4H gene and/or inhibit the activity of the C4H protein. Substances that can inhibit the expression of the C4H gene include antisense oligonucleotides.

Substances that inhibit the activity of the C4H protein include peptide mimetics, C4H antagonists as well as antibodies to C4H. The following non-limiting examples are illustrative of the present invention:

EXAMPLES

Example 1

This example demonstrated the cloning and sequencing of the C4H gene in potato genome and the evaluation of its expression levels in various potato samples with high or low degree of ACD.

Materials and Methods

Potato Tuber Samples

Cultivars Russet Burbank and Russet Norkotah potato tubers were harvested in 2002 from the Nova Scotia Agricultural College research field in Truro, Nova Scotia. The tubers were initially stored at 15° C. for 14 days at 95% relative humidity to promote suberization. The temperature was then gradually decreased over a one-month period to the final storage temperature of 9° C. Two diploid clones, 10908.06 and CH72.03, known for high and low degrees of ACD respectively, were obtained from the Potato Research Centre, Agriculture and Agri-Food Canada in Fredericton, New Brunswick and stored at 9° C. until needed.

Genomic DNA and Total RNA Isolation

Genomic DNA was isolated from Russet Burbank potato tubers using protocol of Doyle and Doyle (1990) with minor modifications. Total RNA was isolated from potato tubers according to the slightly modified method of Bachem et al. (1996). In preparation for RNA isolation, selected potato tubers were peeled and the cortex region removed. The remaining tuber tissue was cut into 1 cm cubes and immediately frozen in liquid nitrogen. The frozen tissue was then ground to a fine powder in liquid nitrogen and stored at −80° C., until the total RNA was extracted.

Primer Design and Sequences

Primers for PCR were designed based on highly conserved regions between the c4h cDNA of red pepper (*Capsicum annuum*) and c4h ESTs in tomato (*Lycopersicom esculentum*) (Table 1) and synthesized by Invitrogen Canada (ON, Canada).

Touchdown PCR

Touchdown PCR was used to amplify c4h gene from genomic DNA as the primers were designed based on sequences of another species and there were suspected mismatched nucleotides between the primer and the target sequences (Sambrook and Russell, 2001b). The PCR reaction mixture contained the following components in a final volume of 25 μL: 50 ng of genomic DNA, 2.5 μL of 10×PCR buffer, 1 μL of 10 mM dNTPs, 1.5 U FastStart Taq (Roche Applied Science, PQ, Canada), and 1 μL of each primer (0.01 mM). PCR cycle parameters were as follows: denaturation for 10 min at 95° C., followed by 30 cycles of denaturing for 20 sec at 94° C., annealing at 60° C. for 30 sec but after the first cycle the annealing temperature decreases by 0.5° C. every cycle there after, and extension at 65° C. for 1 min, following which there was another 30 cycles of 94° C. for 20 sec, 45° C. for 30 sec, and 65° C. for 1 min. There was then a final extension for 7 min at 72° C. The extension time during the cycle was changed from 1 min to 2 min depending on the length of the amplicon expected. If the amplified region was expected to be more than 2 kb in length, an extension time of 2 min was used.

Reverse Transcriptase-PCR (RT-PCR)

The two-step reverse transcriptase-PCR (RT-PCR) method was used to amplify the c4h coding region from synthesized cDNA, as described in the Eppendorf cMaster RTplusPCR kit (VWR International, PQ, Canada). The first step of the two-step method was the synthesis of first strand cDNA from total RNA. The second step of the Eppendorf cMaster RTplusPCR kit was the PCR amplification of the first strand cDNA. Primers at the 5' and 3' ends for RT-PCR reactions were designed based on the sequenced genomic DNA (5' primer: 5'-atggatct-tctcttactggag-3' (SEQ ID NO: 3); 3' primer: 5'-ggtttacacaaa-caaacaac-3'(SEQ ID NO: 4)).

5' and 3' Race

The protocol followed is as described in the 5'/3' RACE kit (Roche Applied Science, PQ, Canada). The primers used in this experiment are shown in Table 2, along with their sequences and melting temperatures. The primers labeled as SP are sequence specific primers designed against sequenced regions of the c4h gene in potato. The first strand cDNA was purified using the High Pure PCR Product Purification kit (Roche Applied Science, PQ, Canada) to remove unincorporated nucleotides and primers as per manufacturer's instructions. The addition of a homopolymeric A-tail to the 5' end of the cDNA was carried out by the enzyme terminal transferase (provided by the kit).

For rare mRNA such as for c4h, a second round of PCR with nested primers was required to obtain a visible PCR product. The nested sequence specific primer (SP3) was designed 75 bp within the previously amplified region, while the reverse nested primer was complementary to the Oligo dT-anchor primer (provided with the 5'/3' RACE kit). As the concentration of the amplified dA-tailed cDNA product was unknown, the nested PCR was performed on both undiluted and diluted (1:20 in water) amplified product. The PCR conditions for amplification were identical to the conditions used in the first round of amplification.

The method of 3' RACE (Rapid Amplification of cDNA Ends) takes advantage of the naturally occurring poly(A) tail of mRNA to amplify the 3' end of a gene. The 5'/3' RACE kit (Roche Applied Science, PQ, Canada) was used to synthesize first strand cDNA and amplify the 3' end using both sequence specific primers and supplied primers.

Cloning of PCR Products into a Plasmid Vector

Media for transformation were made according to standard protocols (Sambrook and Russell, 2001c). PCR reaction mixtures were filtered through the Millipore Ultrafree-DA filter kit (Fisher Scientific, ON, Canada) to remove salts, unincorporated dNTPs, and primers. The ligation of the PCR product to the pGEM®-T vector was set up according to manufacturer's instructions (Promega Corp., Wis., USA). The protocol for the production of E. coli DH5α competent cells and the subsequent transformation was followed as described by Inoue et al. (1990).

DNA Sequencing and Data Alignment

All sequencing of plasmid DNA and PCR products was performed by DNA Landmarks, Inc. (PQ, Canada). The universal primers, T7 (5'-TAATACGACTCACTATAGGG-3' (SEQ ID NO: 5)) and SP6 (5'-GATTTAGGTGACAC-TATAG-3' (SEQ ID NO: 6)) were used for sequencing of the pGEM®-T plasmid DNA constructs. Raw sequence chromatograms were visually edited using the software program Chromas (<http://www.technelvsium.com.au>). Alignment of the sequence data was conducted using the BLAST program available from the National Center for Biotechnology Information (<http://www.ncbi.nlm.nih.gov>) (Altschul et al., 1990).

Northern Hybridization

The probe used for Northern hybridization was a 550 bp cDNA fragment previously amplified using the primers AF and FR (see Table 1) from the Russet Burbank total RNA. The fragment was subcloned into the pGEM®-T vector, as described above. The QIAfilter Plasmid Maxi kit (Qiagen, ON, Canada) was used to isolate plasmid DNA on a large scale from transformed cells as per manufacturer's instructions. The restriction enzyme Pvu II was used to release the insert from the vector as it cuts outside of the T7 and SP6 promoter/primer sites of the vector, which are necessary for PCR amplification and transcription.

The c4h probe was then PCR amplified using the T7 and SP6 primers using standard PCR conditions. The amplified product was filtered through the Millipore Ultrafree-DA filter kit, prior to labeling. The probe was radioactively labeled using the DECAprime™ II Random Priming DNA Labeling kit (Ambion, Tex., USA). For use as a positive control, the c4h probe was transcribed to RNA (Sambrook and Russell, 2001a) and loaded to the denaturing gel along with the samples. Any DNA remaining was degraded by incubating for 15 min at 37° C. with 20 U of DNase I, after which it was diluted to 1:100 and 1:1000 and stored at −20° C. in 10 μL aliquots.

RNA from Russet Burbank and Russet Norkotah potato tubers as well the RNA from identified ACD-dark (10908.06) and ACD-light (CH72.03) diploid clones were analyzed. To ensure that the pattern and intensity of the hybridization signal measured for each of the four tuber samples was reproducible, the Northern hybridization experiment was replicated three times using identical conditions.

Denaturing gel electrophoresis and membrane transfer of the RNA samples (30 μg total RNA/sample) was performed according to standard protocols (Sambrook and Russell, 2001a). Prehybridization of the membrane was performed in 6 mL of Ultrahyb hybridization buffer (Ambion, Inc., TX, USA) for 1 h at 42° C. The buffer was replaced with 6 mL of new Ultrahyb solution containing the denatured probe. Hybridization of the membrane was performed overnight at 42° C. Following hybridization, the membrane was gently rinsed in 5×SSC at room temperature, then washed 2× for 5 min each at 37° C. in 5×SSC with 0.1% SDS, and lastly in 1×SSC with 0.1% SDS 2× for 15 min each at 37° C. The membrane was exposed to Kodak BioMax XAR film (Fisher Scientific, ON, Canada) 5 to 10 d prior to developing. The film was developed using Kodak GBX Developer and Fixer (Fisher Scientific, ON, Canada) as per manufacturer's instructions.

Evaluation of ACD in Cooked Potato Tubers

To correlate c4h transcript levels with the degree of tuber darkening; the ACD levels of each potato cultivar used in the Northern hybridization experiment were digitally measured. As the length of tuber storage affects the degree of darkening, ACD levels of the tuber samples were measured at the same time period as the tuber samples were frozen for subsequent hybridization experiments. The level of darkening was digitally measured based on a gray scale of 256 pixel units, where white has a pixel density of 255 and black a pixel density of 0. Therefore, a higher pixel density was indicative of a lighter tuber while a lower pixel density corresponded to a darker tuber.

Four tubers for each tetraploid cultivar and two tubers for each diploid clone were cooked by steaming, sliced lengthwise, and the cut surfaces exposed to air for 1 hour to allow darkening to develop. For the tetraploid cultivars, the pixel density of the entire surface of four tuber halves (one half from each tuber) was measured. As there were a limited number of tubers available for the diploid clones, the pixel density of both halves of each of the two cooked tubers was measured. The images of four tuber surfaces for each sample were captured and digitally evaluated using the UVP Chemi-Imager System and LabWorks Imaging Analysis and Acquisition Software.

The four ACD measurements for each tuber cultivar/clone were analyzed by a one-way analysis of variance using the Proc GLM (General Linear Model) procedure of SAS (Version 8, SAS Institute, NC, USA). Significance at the 5% level (P-value<0.05) was further examined using Tukey's honestly significant difference (hsd) test ($\alpha=0.05$) to compare the mean pixel densities. Normality and constant variance were tested using the Proc Univariate procedure of SAS using the predicted and residual values. The data proved to be normal without transformation of the data.

Results

The c4h Gene in Potato

The analysis of the sequencing data generated from the genomic DNA and cDNA clones led to the identification of the 5'- and 3'-UTR, three exons, and two introns from the 2986 bp DNA sequence of the potato genome. The complete c4h gene sequence is shown in Table 3. The coding region of the gene is 1518 bp in length, starting at the ATG nucleotides at positions 45 to 47 and stopping at nucleotides TAA at positions 2861 to 2863. The coding region contains three exons (shown in bold) and two introns. Exon 1 is 785 bp in length (from nucleotide 45 to 829), exon 2 is 134 bp (from nucleotide 1363 to 1496), while exon 3 is 599 bp (from nucleotide 2265 to 2863). Intron 1 and 2 are 533 and 768 bp, respectively. Intron 1 is located between nucleotides 785 and 786 of the coding region and intron 2 is located between nucleotides 919 and 920. The partially sequenced 5'- and 3'-UTR measures 44 (positions 1 to 44) and 123 bp (position 2864 to 2986) in length, respectively.

The C4H protein sequence is composed of 505 amino acids (not including the stop codon), as shown in Table 4. The typical start (ATG) and stop (TAA) codons are found at the beginning and end of the open reading frame. The splice sites for introns 1 and 2 are depicted by arrows in Table 4. Intron 1 is found between the second and third nucleotides of the codon (AA/G), which corresponds to the amino acid lysine (amino acid position 262). Intron 2 is positioned between the first and second nucleotides of the codon (G/CA), which codes for the amino acid alanine (amino acid position 307).

The Gene Expression of c4h in Tuber Tissues

The c4h hybridization signals in the four tuber samples are shown in FIG. 1, panel A. The size of the c4h transcript was measured based on the location and known size of the transcribed c4h probe (710 bp) and the 25S, 18S, and 5S ribosomal RNA bands (3.8 kb, 2.0 kb, 0.74 kb, respectively, FIG. 1, panel B). The size of the c4h signal is between 600 and 800 bp. The intensity of the c4h transcript for each potato sample was measured relative to the Russet Burbank signal, which was assigned a value of 1.0, using Labworks Imaging and Acquisition Software.

In order to verify that there was equal loading of the total RNA used for Northern hybridization, the ribosomal RNA (both the 18S and 25S bands) was quantified digitally from an underexposed agarose gel image (not shown), like that shown in FIG. 1B, prior to transferring the RNA to the membrane. The Russet Burbank 18S and 25S ribosomal RNA bands were assigned a value of 1.0. The relative intensities of the remaining three samples were given a value relative to the Russet Burbank RNA. The relative intensities of the c4h transcript were adjusted according to the proportion of RNA loaded for each sample. The mean adjusted c4h transcript levels of the four tuber samples are shown in Table 5. The mean c4h transcript levels are significantly different between the dark and light diploid samples with 1.70 and 0.91, respectively. The intensity of the c4h hybridization signal was not significantly different between the dark diploid sample and the two tetraploid cultivars. As well, there were no significant differences among the tetraploid cultivars and the light diploid sample.

Figure 2:
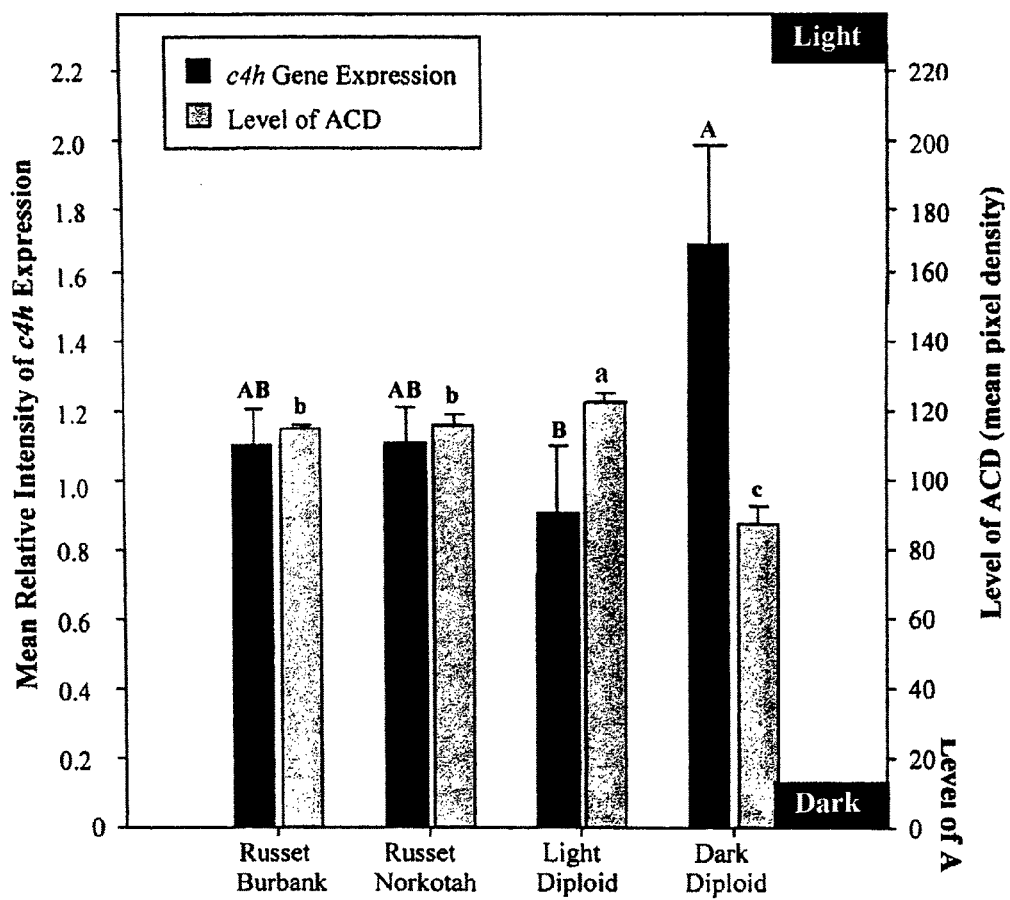
FIG. 2: A graph showing the relationship between c4h gene expression and ACD level in potato tubers. Black bars represent the mean relative intensity of c4h expression (left axis) and gray bars represent the digital measurement of ACD in the potato tubers (right axis). A lower pixel density reading (right axis) represents higher ACD. Different upper case letters represent significance for the mean relative intensity of c4h expression, according to Tukey's hsd test at $\alpha=0.05$. Different lower case letters represent significance between the ACD levels, according to Tukey's hsd test at $\alpha=0.05$.

The potential relationship between ACD and c4h gene expression was analyzed by comparing the mean relative c4h transcript levels to the mean degree of darkening previously measured for each tuber sample (FIG. 2). The mean pixel densities of Russet Burbank and Russet Norkotah tubers were found to be 113 and 114, respectively, which was not significantly different at $\alpha=0.05$. For the light diploid clone CH72.03, the mean pixel density was slightly higher (121 pixel units), which corresponded to a lower degree of ACD. The mean pixel density of the dark diploid clone 10908.06 was found to be significantly lower at 89 pixel units, which corresponds to a higher level of tuber darkening.

As seen in FIG. 2, there are no significant differences in the degree of ACD or in intensity of the c4h transcript in Russet Burbank and Russet Norkotah. In contrast, the degree of darkening in the identified dark diploid sample is significantly higher when compared to the identified light diploid, and the relative intensity of the c4h hybridization signal is also significantly higher in the dark diploid when compared to the light diploid. These results suggest that the level of the c4h transcript may determine the susceptibility of the tuber to ACD.

Discussion

In this study, the 2986 bp c4h gene was sequenced from the potato cultivar Russet Burbank. This full-length sequence included the coding region, two introns, and partial 5'- and 3'-UTR. The c4h gene has been sequenced in a number of plant species, however it had not previously been cloned from the potato genome. The coding sequence for the potato c4h gene, from the start codon (ATG) to the stop codon (TAA), is 1518 bp in length.

The similarity of class I c4h coding sequences from other plant species to the potato c4h coding sequence is shown in Table 6. The nucleotide sequence of red pepper is the most similar to potato at 91% (1379 bp of 1518 bp), which was anticipated as both belong to the Solanaceae family. The sequence similarity of the remaining plant species to the potato c4h coding sequence, range from 67% to 82%.

The c4h coding region in potato is 1518 bp in length, which is identical to the length of most other class I c4h coding regions (Table 6). From the species listed in Table 6, only three were of a different length when compared to potato. The coding region of alfalfa and Bishop's weed are 3 bp longer (1521 bp), corresponding to an additional amino acid. In alfalfa, the three extra nucleotides (codon GAT) occur at positions 848 to 850 of the coding sequence; translating to the amino acid aspartate at position 274 of the peptide sequence. Conversely, the additional amino acid in the Bishop's weed peptide sequence is a methionine occurring at position 1, after translation. This corresponds to the nucleotide codon ATG, which is followed by the typical ATG start codon. Sweet orange is the third plant species showing a significantly longer c4h coding region, with a length of 1560 bp. The sweet orange c4h coding region contains an additional 42 bp, corresponding to fourteen amino acids. The sweet orange c4h gene carries a unique N-terminus from nucleotides 10 to 106, which not only contains the 42 additional nucleotides but also shows no homology to this region in other c4h genes.

Figure 3:
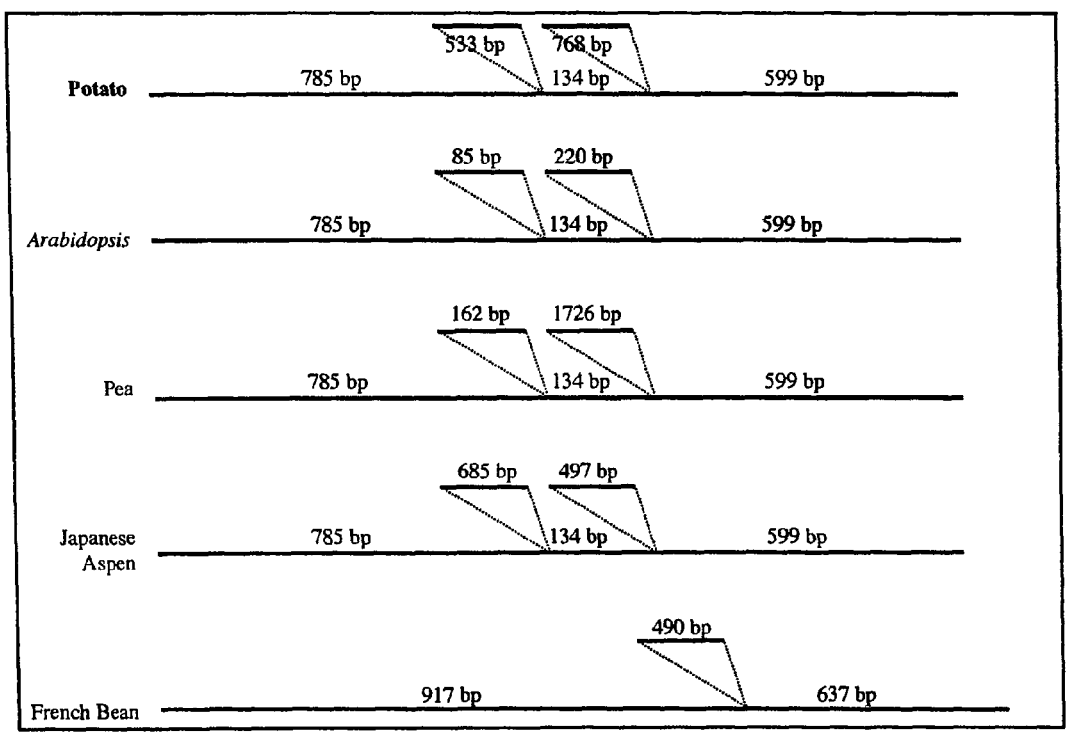
FIG. 3: Comparison of exon and intron lengths of the potato c4h gene to that of other plant species. Diagram not to scale.

In potato, the three individual exons are 785, 134, and 599 bp which together make up the complete c4h coding region. The lengths of the c4h gene have only been cloned from genomic DNA in *Arabidopsis*, pea (*Pisum sativum*), Japanese aspen, and French bean (*Phaseolus vulgaris*) (Kawai et al., 1996; Bell-Lelong et al., 1997; Nedelkina et al., 1999; Whitbred and Schuler, 2000). The first three are class I c4h genes, whereas the c4h gene from French bean is class II. FIG. 3 depicts the positions and lengths of the exons and introns in the four plant species as well as in potato. The similarity between the exon lengths of potato, *Arabidopsis*, pea, and Japanese aspen would suggest that there is a conserved splice position in all class I c4h genes. When compared, it was found that the nucleotides flanking the splice site positions for both introns were identical in all four plant species (FIG. 3). The splice site for intron 1 occurred between the second and third nucleotides of the codon AA/G at positions 785 and 786 of the coding region. The codon, disrupted by intron 1, corresponds to the amino acid lysine at position 262 of the protein sequence, Table 4. The second intron excision site is between nucleotides 919 and 920 of the coding region at codon G/CA. This codon represents the amino acid alanine at a position of 307 (Table 4). The class II c4h gene from French bean, differs from the others as it only contains two exons and one intronic region.

Two introns corresponding to those in the c4h gene were cloned from the potato genome. The lengths of the introns are 533 and 768 bp for the first and the second introns, respectively. Although the c4h gene in potato, *Arabidopsis*, pea, and Japanese aspen each contains the same number of introns, seemingly identical intron splice sites, and homologous coding regions; there is no homology among the intron sequences. Furthermore, a comparison of the potato c4h intron sequences to the entire Genbank® database resulted in no sequence matches. The lack of homology for the c4h introns is also reflected in the differences between the lengths of the introns.

The intron sizes appear to relate to the complexity and size of the corresponding plant genome. Evidence to this effect is demonstrated by the pea c4h gene, which has one of the largest introns (1726 bp). The genome size of pea is $4.8 \times 10^9$ bp, making it one of the largest and most complex genomes in the plant kingdom Ellis and Poyser, 2002). In contrast, *Arabidopsis* has the shortest introns and the smallest plant genome at $1.1 \times 10^8$ bp (The *Arabidopsis* Genome Initiative, 2000). Japanese aspen and potato fall into the mid-range with introns of approximately 500 to 800 bp and genome sizes of between $5.0 \times 10^8$ bp and $8.7 \times 10^8$ bp, respectively (Arumuganathan and Earle, 1991; Taylor, 2002). Previous studies have shown weak correlations between intron and genome size in eukaryotes, including humans, *Drosophila*, and Japanese pufferfish (*Fugu rubripes*) (Moriyama et al., 1998; McLysaght et al., 2000). There is little information on the correlation of intron size to genome size in plant species but it has been suggested that plants with small genomes also have smaller introns (Deutsch and Long, 1999). Conversely, it was demonstrated that different sized genomes in cotton species had no impact on intron size (Wendel et al., 2002).

The 5'-untranslated region (5'-UTR) is the region from the transcriptional initiation site to the start codon for translation. Previously, it was reported that the average length of the 5'-UTR in plants was 168 bp, while the average length in dicot species was 98 bp (Pesole et al., 1997; Kochetov et al., 2002). The complete 5'-UTR for c4h is only available in two other plant species: *Arabidopsis* and French bean where it was measured to be 86 and 78 bp, respectively. In comparison the 5'-UTR for the potato c4h gene was only 44 bp in length. This indicates that either the potato c4h 5'-UTR is much shorter than the average or that only the partial 5'-UTR in potato has been sequenced. Alignment of the 5'-UTR sequences from *Arabidopsis*, French bean, and potato has found that there is no similarity between any of the three sequences. A search of the Genbank® database for sequence similarity to the potato 5'-UTR also did not result in any significant similarities to any other 5'-UTRs. This makes it difficult to determine whether the one sequenced in potato is the entire 5'-UTR.

A sequence characteristic of the 5'-UTR is the pronounced imbalance between the levels of GC and AU. The partial c4h 5'-UTR in potato also demonstrates this imbalance with a GC content of 34.1% and an AU content of 65.9%. This is comparable to the average GC content in the 5'-UTR of dicot species of 39% (Kochetov et al., 2002). This low GC content reduces secondary structures allowing translational efficiency to be improved (Groenewald et al., 2000; Kochetov et al., 2002).

In this study, a 123 bp 3'-UTR was sequenced for the potato c4h gene. In plants, this region is thought to be much more variable in length among species than the 5'-UTR, ranging from 240 to 740 bp (Pesole et al., 1997). The GC content of the c4h 3'-UTR in potato is the lowest at 24.4%, when compared to other regions of the gene. A review on plant 3'-UTRs showed that the GC content is the lowest in the 3'-UTR (35%/o) when compared with other regions of the plant genome (Pesole et al., 1997). The c4h 3'-UTR GC content is much lower than the reported value however it would seem that every segment of the c4h gene contains a lower GC content when compared to published literature. A BLAST comparison of the 3'-UTR to other nucleotide sequences in Genbank®, resulted in only the c4h 3'-UTR from red pepper (Accession # AF212318) showing any homology. The sequence alignment of the 123 bp 3'-UTR from potato resulted in a match of 92 bp out of the first 123 bp in the red pepper 3'-UTR. In red pepper the 3'-UTR has a length of 219 bp, ending with the conserved polyadenylation signal. It is then believed that the 3'-UTR in potato is only partially cloned, since the polyadenylation signal was not identified at the 3' end.

The C4H protein consists of 505 amino acids, excluding the stop codon (Table 4). The alignment of C4H amino acid sequences showed high homology between potato and the same protein in many other plant species, as seen in Table 7. The highest sequence similarity to potato was shown to be the red pepper C4H amino acid sequence at 87%. The other 14 plant species were very similar to the potato C4H amino acid sequence with a similarity of between 84 and 80%.

A comparison of the potato C4H amino acid sequence to C4H sequences from other plant species allows homologous regions and domains unique to the CYP73 protein family to be identified. The alignment of six C4H sequences showing high similarity to potato (red pepper, lithospermum, Madagascar periwinkle, tree cotton, wild licorice, and poplar) is shown in Table 8 (SEQ ID NOS: 2, 29-34, respectively, in order of appearance). The first domain is a hydrophobic region at the N-terminus from position 3 to 23, represented by Box A in Table 8 (Ro et al., 2001). This region is responsible for membrane binding, protein stability, and is a signal-anchor to keep the protein on the cytoplasmic side of the endoplasmic reticulum (Hotze et al., 1995; Nedelkina et al., 1999). Among the plant species shown in Table 8, the majority of the substitutions involve the same five amino acids, isoleucine (1), valine (V), leucine (L), phenylalanine (F), and alanine (A), which are all hydrophobic in nature. This indicates that the presence of hydrophobic amino acids is partly responsible for the function of this domain, rather than the presence of specific amino acids.

The second domain is a proline rich region which occurs from amino acid 34 to 41 of the C4H protein sequence (Box B in Table 8). This region is thought to be responsible for correctly orientating and folding the protein in the membrane by breaking cc-helix bonds (Mizutani et al., 1997; Koopmann et al., 1999).

Cytochrome P450 proteins contain a conserved region that is involved in the binding and activation of dioxygen, which is necessary for oxygen incorporation into the corresponding substrates (Schalk et al., 1999). The consensus sequence for this region in plant P450 proteins is as follows; (A/G)(A/G)I (E/D)T. As seen in Table 8 (Box C), the sequence of the motif in the C4H protein family is AAIET and is identical in all plant species shown.

One of the most important domains in the P450 family of proteins is the heme-binding domain positioned at amino acids 439 to 449 (Box D of Table 8). The consensus sequence for this domain in P450 proteins is PFGXGRRXCXG. In the CYP73 family, the domain (PFGVGRRSCPG) is conserved in all plant species sequenced, indicating that there is a consensus sequence specifically for C4H. The importance of this domain is that it allows the binding of the heme molecule to the enzyme which is essential for catalysis and the ability to bind carbon monoxide (Chapple, 1998). The binding of the heme molecule occurs through a thiolate side chain that originates from the conserved cysteine amino acid at position 447 (Schalk et al., 1999). In the C4H family of proteins, the interaction of the conserved cysteine (C) and the subsequent proline (P) molecule enables the formation of a "cysteine pocket" in which the sulfur-iron bond is in the center of a hydrophobic environment (Schalk et al., 1999).

The objective of the Northern hybridization analysis was to determine if changes in c4h gene expression occurred in cultivars with varying degrees of ACD. The results of the Northern hybridization and the ACD evaluation data suggest that potentially there is a relationship between c4h gene expression and ACD, as seen in FIG. 1. The level of the darkening for Russet Burbank and Russet Norkotah tubers was similar at 113 and 114 mean pixel density, respectively.

Russet Norkotah generally is considered darker than Russet Burbank based on other researcher's observations (Wang-Pruski, personal communication), but samples from this growing location and year provided very similar ACD levels for both samples. As shown in FIG. 1, the mean relative intensity of c4h transcript in Russet Burbank and Russet Norkotah was also not significantly different.

The mean pixel density of the two tetraploid cultivars was significantly lower when compared to the light diploid clone. However, the mean relative intensity of the c4h transcript in the tetraploid cultivars was not significantly different to the light diploid clone. Although the dark diploid clone had a significantly lower mean pixel density as compared to the tetraploid cultivars; it was not significantly different in terms of the c4h transcript intensity. The mean relative intensity of the dark diploid sample was much higher than the other samples tested, however because of the high variability among the three replicates for the dark diploid clone (as shown by the standard error bars on FIG. 2) there was no significant differences to the tetraploid cultivars. Finally a comparison of the two diploid clones showed that the identified light diploid clone had a significantly higher mean pixel density (lower ACD susceptibility) and had significantly lower c4h transcript intensity. On the other hand, the identified dark diploid clone had a significantly lower mean pixel density (higher ACD susceptibility) and demonstrated significantly higher c4h transcript intensity.

The lack of significant differences between the tetraploid cultivars for ACD and c4h transcript intensity, as well as the significant differences in intensity for the dark and light diploid clones suggests that c4h is involved in the ACD mechanism. This evidence indicates that there is a possible relationship between c4h gene expression levels and the level of darkening in the tuber, where potato cultivars with higher c4h expression levels have an increased susceptibility to ACD, and vise versa.

The Northern hybridization results show that the size of the signal measured does not match the full-length 1.5 kb c4h transcript. The transcript detected is 600 to 800 bp in length, which is much shorter than the full-length cDNA cloned in this study. It is unlikely that non-specific hybridization occurred, as the probe was homologous to only those sequences encoding c4h in Genbank® and the transcript was detected at the same position in each of the four samples. Degradation of the RNA is not likely since electrophoresis of the total RNA used in the Northern hybridization experiment (FIG. 1A) showed intact 25S and 18S bands. The presence of intact and distinct 28S (25S in potato) and 18S ribosomal RNA bands is considered the simplest and best indicator of high quality RNA (Miller et al., 2004; Palmer and Prediger, 2004).

In this study, the hybridization probe was homologous to the 5' end of the gene (from 100 bp to 572 bp of the coding sequence), which means any degradation occurring at the 3' end would not have been detected. The truncation of an mRNA transcript can be the result of controlled degradation (decay) of the mRNA, alternative pre-mRNA splicing of exons/introns, or cleavage by microRNA (miRNA). All three of the above mechanisms are key in the regulation of gene expression at the mRNA level (Konig et al., 1998; Yu and Kumar, 2003).

Controlled degradation of the mRNA is the first possible mechanism for creating truncated mRNA in order to regulate the gene expression levels. In *E. coli*, mRNA levels are regulated by 3' to 5' exonucleases or endonucleolytic cleavage, followed by 3' to 5' exonucleolytic degradation of the products (Belasco and Higgins, 1988). Eukaryotic mRNA is polyadenylated and is degraded by first deadenylation and then degradation of the mRNA in a 3' to 5' direction. The speed of this degradation determines the half-life of the mRNA molecule. The degradation of eukaryotic mRNA is a fast and flexible form of posttranscriptional regulation and allows plants to adapt rapidly to changing conditions (Sullivan and Green, 1996).

In soybean and petunia, it was found that the degradation of mRNA encoding ribulose-1,5-bisphosphate carboxylase (rbcS) occurred by endonuclease cutting of the full-length transcript at several specific sites in a 3' to 5' direction (Tanzer and Meagher, 1994). The degradation of SAUR (small auxin up RNA) transcripts in soybean occurred within 10 to 50 min (Sullivan and Green, 1996). In mitochondrial transcripts analyzed from pea, it was found that the length of the poly(A) tail influences the rate of mRNA decay (Kuhn et al., 2001). A poly(A) tail composed of more than 10 adenine molecules results in the degradation of the full-length transcript after 10 min into multiple smaller products. When only 3 adenine molecules comprised the poly(A) tail, no degradation of the transcript occurred after 60 min (Kuhn et al., 2001).

Alternative pre-mRNA splicing of exons/introns is the second possible mechanism for the truncation of mRNA transcripts. The regulation of alternative splicing is dependent on factors such as: developmental stage, tissue type, and response to various stimuli including growth factors, hormones, cytokines, membrane depolarization, and wounding (Konig et al., 1998). The alternative splicing of a transcript can often lead to premature termination of translation, altered protein structure, and a loss of protein stability or function. Alternative pre-mRNA splicing of the introns has resulted in the presence of truncated mature transcripts in morning glory (*Ipomoea purpurea*), peach (*Prunus persica*), and tobacco (*Nicotiana tabacum*) (Dinesh-Kumar and Baker, 2000; Bassett et al., 2002; Zufall and Rausher, 2003). In morning glory, a large DNA insertion in an intronic region of the gene encoding flavonoid 3'-hydroxylase resulted in the mis-splicing of the pre-mRNA and a corresponding shift in the open reading frame. The resulting transcript was only 500 bp compared to the full-length transcript of 910 bp (Zufall and Rausher, 2003). Alternative splicing of an intron in an ethylene receptor gene in peach resulted in two different length mature transcripts (Bassett et al., 2002). The longer of the two transcripts produced was found to be the most abundant in developing fruit, suggesting that developmental processes regulate the alternative splicing of this gene. It seems unlikely that alternative splicing of the c4h transcript occurred, as it would probably lead to a loss of enzyme function. As the C4H enzyme is involved in the regulation of the phenylpropanoid pathway, it would be necessary for its activity to be maintained.

The final mechanism for truncation of the transcript is cleavage by miRNA. Recent findings have suggested that 21 nt miRNA are involved in gene expression regulation in plants through miRNA-directed cleavage (Xie et al., 2003). Each miRNA has an exact complementarity to the target mRNA. The miRNA binds to the target where it directs the cleavage of the mRNA transcript at the binding site (Floyd and Bowman, 2004). To date, most of the targets identified are transcriptional factors that are crucial to cell growth and development (Ke et al., 2003). Rhoades et al. (2002) found that out of 49 predicted targets for miRNA-directed cleavage, at least 34 encoded for known or putative transcription factors. Studies of miRNA-directed cleavage have been reported in the model plant species, *Arabidopsis*. The truncation of mature transcripts by miRNA-directed cleavage is a possible mechanism for posttranscriptional regulation. However, based on the limited studies available it seems as though miRNA-directed cleavage is a posttranscriptional form of regulation or transcriptional factors rather than functional genes, such as c4h.

Based on the evidence presented, the most likely mechanism for truncation of the potato c4h transcript would be controlled degradation. Although it has not been reported previously in potato tubers, controlled mRNA degradation of c4h is possible. The degradation of the c4h transcript would lead to the detection of different length hybridization signals. Since the C4H enzyme is in such low quantities in plant tissue; its rapid rate of degradation would lead to difficulties in detecting the full-length transcript. Also, as C4H is a regulatory enzyme in the phenylpropanoid pathway; controlled mRNA degradation would be a fast and efficient way to regulate c4h transcript levels during the biosynthesis of CA.

Example 2

The goal of this example was to study the differential gene expression of C4H gene in ACD susceptible (dark) and ACD resistant (light) diploid potato clones and tetraploid cultivars that are involved in the ACD trait.

Differential gene expression analysis of C4H gene in ACD dark and light clones of diploid families and tetraploid cultivars were performed using relative quantitative RT-PCR. Chlorogenic acid, citric acid, and chlorogenic acid to citric acid ratio in the selected samples were analyzed. Statistical methods were used to find the significant differences in differential gene expression data and chemical concentration data among ACD dark and ACD light samples.

Statistical analyses were performed to study the effect of ACD (dark and light) on the expressions of the C4H gene and the chemical concentration in the samples.

Materials and Methods

Potato Samples

Potato clones of two diploid families and two tetraploid cultivars were used in this study. The clones of the diploid families used were the progenies of two individual crosses between the ACD dark and ACD light parents. The clones originated from one cross were named family 13610 and the clones originated from another cross were named family 3395. The clones of the family 13610 grown at the research field at Nova Scotia Agricultural College, Truro, Nova Scotia was named as 13610-T. The clones of the family 13395 were grown at Potato Research Centre, Agriculture and Agri-Food Canada, Benton Ridge, Fredericton, New Brunswick was named as 13395-B. The two tetraploid cultivars, Russet Burbank and Shepody were grown at the research field at Nova Scotia Agricultural College, Truro, Nova Scotia. All the tubers were grown and harvested in 2002 and 2003 season. Standard field practices were carried out for all the tubers. Only tubers from 2003 seasons were used for differential gene expression analyses.

The harvested tubers were packed in paper bags and subsequently stored in the cold storage room, at 15° C. and 95% relative humidity for two weeks at. The storage temperature was decreased gradually to 10° C. over a month, tubers were finally stored at 9° C. with 95% relative humidity.

ACD Evaluation

ACD evaluation was performed for all the tubers of the diploid families and tetraploid cultivars. The ACD levels of the stored tubers were measured in January. That is, ACD levels for tubers harvested in year 2002 was carried out in 2003 and for the tubers harvested in 2003 were performed in 2004. The January ACD measurements of 2003 and 2004 were used for sample selection in this study. ACD evaluation was done using digital imaging (Wang-Pruski and Tarn, 2003) by a lab technician for both the years. Digital images of the cooked tuber surface were taken using a cooled CCD camera attached to the UVP Biochemi Imaging System (UVP Inc., Upland, Calif., USA). The LabWorks™ image acquisition and analysis software (UVP Inc., Upland, Calif., USA) was used for acquiring the digital image of the cooked tubers. The degrees of ACD in the cooked tubers were measured using mean raw pixel density (MRD) at 0-255 pixel levels (where 0 is black and 255 is white). Only the potato clones with white flesh color were used.

Sample Selection

The ACD levels were evaluated in all the tubers of diploid families for January 2003 and January 2004. The tubers with the lowest MRD are considered to be susceptible to ACD (ACD dark) and the tubers with the highest MRD are considered to be resistant to ACD (ACD light). The ACD values measured were plotted in ascending order (lowest MRD to the highest MRD) against the respective clones of each diploid family under study. The ACD data collected from the two years (January 2003 and January 2004) were correlated. Two or three diploid clones showing similar ACD values in both January 2003 and January 2004 were chosen. Similarly the ACD measurements of tetraploid cultivars, Shepody and Russet Burbank were measured in January 2003 and 2004.

Sample Preparation

Figure 4:
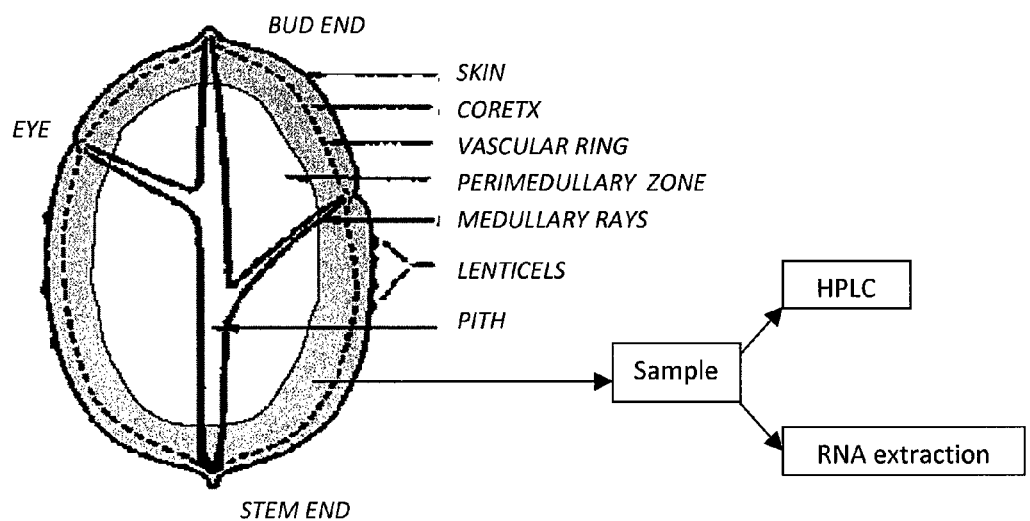
FIG. 4: Schematic representation of tissue sampling for HPLC analysis and RNA extraction.

The selected potato tubers were carefully peeled to remove the outer skin. The tubers were then cut in half and the center region including the pith was carved out. The outer layer (FIG. 4), which was about 1 cm in breadth, was chopped using a knife. The chopped tuber pieces were used for: 1) fresh tuber samples were used for the measurement of chlorogenic acid and citric acid by high performance liquid chromatography (HPLC), and 2) the remaining tuber pieces were frozen in liquid nitrogen and stored at −80° C. for total RNA extraction.

Primer Design

The nucleotide sequences of the cDNA of selected candidate genes were either obtained from Genbank (http://www.ncbi.nlm.nih.gov/), or from the potato molecular biology lab at NSAC. The obtained sequences were used to design primers using online primer designing software Primer3 (http://frodo.wi.mit.edu/cgi-bin/primer3/primer3_www.cgi). The primers were selected based on the following characteristics: the minimum primer length was 15 nucleotides, the product size was less than 700 bp, melting temperature was between 55° C. to 65° C., GC concentration was between 45% to 60%, base pair self complimentarity was less than 4 nucleotide pairs, 3' complimentarity was less than 3 nucleotide pairs.

Total RNA Extraction from Potato Tubers

Total RNA was extracted using the protocol followed by Singh et al. (2003). The frozen potato tubers were ground with a presterilized pestle in a mortar using liquid nitrogen. About 300 mg of the frozen tuber was transferred to a 2 ml microcentrifuge tube. To the frozen potato powder 500 µf extraction buffer (50 mM Tris-HCl, pH 9.0; 150 mM NaCl; 1% sarkosyl; 20 mM EDTA; 5 mM DTT) was added. After vortexing the tube, 500 µl of phenol:chloroform:isoamyl alcohol (25:24:1) was added. The tube was vortexed again and centrifuged at 19,000 g for 6 minutes at 4° C. After the centrifugation the upper aqueous layer (~600 µl) was carefully removed and placed in a new tube. To the aqueous phase 650 µl of guanidium buffer (8M guanidine hydrochloride; 2 mM EDTA; 20 mM MES, pH 7.0) was added, then β-mercaptoethanol with final concentration of 20 mM was added. The solution was mixed well and then 350 µl of phenol: chloroform:isoamyl alcohol (25:24:1) was added. The tube was then centrifuged at 19,000 g for 6 minutes at 4° C. After the centrifuge the upper aqueous phase was removed without disturbing the interface. To the upper aqueous phase 500 µl of chloroform was added and mixed well. The tube was again centrifuged at 19,000 g for 6 minutes at 4° C. The upper aqueous phase containing the nucleic acids was carefully transferred to two new 2 ml microcentrifuge tube (~600 µl each). To each tube, 60 µl of 3M sodium acetate (pH 5.2) and 1.2 ml of chilled 100% ethanol was added. The tubers were inverted gently and then incubated at −75° C. for 2 hours. After incubation the tubes were centrifuged at 19,000 g for 20 minutes at 4° C. The supernatant was discarded and the RNA pellet was washed with 80% ethanol. The tube was then air dried at room temperature for 10 minutes. The RNA pellet was dissolved in 20 µl of autoclaved deionised filter-sterilized water. The RNA was run on a 1% agarose gel to check for the quantity and quality.

DNase Treatment

The isolated RNA was treated by DNase-I (Promega Corp., WI, USA) to remove any residual DNA contamination that may interfere with the RT-PCR reactions. The RQ1 RNAse free-DNase (Promega Corp., WI, USA) was used to treat the isolated total RNA. The 40 µl DNAse reaction mix contained the following 20 µl (~10 µg) RNA, 4 µl 10× DNAse buffer (400 mM Tris-HCl, pH 8.0; 100 mM MgSO$_4$; 10 mM CaCl$_2$), 25U RNAse inhibitor (Promega Corp., WI, USA), 15 µl RNAse free water. The mixture was mixed well and then incubated at 37° C. for 1 hour. After the incubation the volume of the reaction mix was made up to 300 µl using RNAse free water. To the solution 300 µl of phenol:chloroform:isoamyl alcohol (25:24:1) was added and mixed well. The tube was centrifuged at 14,000 g for 10 minutes. The upper aqueous phase was removed carefully to a new microcentrifuge tube. To the solution 200 µl of chloroform was added, mixed well and centrifuged for 10 minutes at 14,000 g. The upper aqueous phase (µ300 µl) was removed and 30 µl of 3M sodium acetate (pH 5.2) and 600 µl of chilled 100% ethanol was added. The solution was mixed gently and then incubated at −75° C. for 2 hours. After incubation the tube was centrifuged at 19,000 g for 20 minutes at 4° C. The RNA pellet was washed with 80% ethanol, air dried for 10 minutes and dissolved in 10 µl of autoclaved deionised filter-sterilized water. One microliter of the RNA sample was loaded in a 1% agarose gel to estimate the concentration and test the quality of the total RNA.

Reverse Transcription

The single stranded cDNA synthesis from the total RNA was carried out using avian myeloblastosis virus reverse transcriptase (AMV-RT) (Roche Applied Science, PQ, Canada). Random Primers (Roche Applied Science, PQ, Canada) were used to reverse transcribe the RNA to single stranded cDNA. A 25 µl reverse transcription reaction mix contains ~650 ng of total RNA, 20U of AMV-RT (Roche Applied Science, PQ, Canada), 5 µl of incubation buffer (50 mM Tris-HCl; 8 mM MgCl$_2$; 3 mM KCl; 1 mM dithiothreithol, pH 8.5), 5 µl dNTPs (10 mM), 2.5 µl of 10× random hexanucleotides (Roche Applied Science, PQ, Canada), 25U of RNAse inhibitor (Promega Corp., WI, USA) and ddH$_2$O to a total volume of 25 µl. The mixture was incubated at 42° C. for 70 minutes and the enzyme was deactivated at 80° C. for 5 minutes.

Determination of Linear Range Sensitivity for Imaging Device

The UVP Imaging device was used to quantify the differential gene expression analysis. The linear range of sensitivity of the device has to be determined for absolute quantification of intensities of the PCR product bands in an agarose gel. This was determined by performing a series of PCR experiments with varying initial copy numbers of a vector plasmid. The vector plasmid used was a pGEMT vector cloned with the C4H gene PCR product of about 514 bp. The copynumbers of the plasmid was estimated on the size and concentration of the plasmid (Arumugananthan and Earle, 1991). The initial copy numbers of the plasmid ranged from $10^2$ to $10^{10}$ copies. A 27 cycle PCR was carried out and the PCR products were run on a 1.2% agarose gel. The intensities of the bands were measured using the Labworks™ software (UVP Inc., Upland, Calif., USA). A graph was plotted for measured the maximum pixel density of the bands against the initial copynumbers.

Optimization for Relative Quantitative RT-PCR

Accurate quantification of differential gene expression analysis using relative quantitative RT-PCR needs optimization of the following; 1) annealing temperature for selected gene specific primers, 2) PCR cycle numbers and 3) the internal standard for each selected candidate gene. All the PCRs for optimization and relative quantitative RT-PCR were performed in Bio-Rad iCycler thermal cycler (Bio-Rad Laboratories, ON, Canada).

1) Optimization of Annealing Temperature and PCR Cycle Number

The annealing temperature of the selected genes was first optimized by performing RT-PCR for each gene with varying annealing temperatures. The annealing temperatures tested were ranged from 50° C. to 53° C.

In a PCR the amplified products tend to reach a plateau stage after reaching a threshold cycle. It is therefore necessary to find the threshold cycle limit for each candidate gene before analyzing them together for differential gene expression analysis. The threshold limit for the PCR cycle was determined by performing a series of PCR.

2) Optimization of Internal Standard

The 18 s rRNA primers (QuantumRNA™, Ambion inc., TX, USA) can amplify 315 bp fragment specific to 18 s rRNA in all plants. The 18 s rRNA primers were used as an internal standard to monitor any sample to sample variation in the amount of initial cDNA. It also acts as an internal control for any differences in the reverse transcription and/or PCR processes. The 18 s rRNA is abundant in the isolated total RNA which makes it difficult to be used as an internal control. The use of competimers overcomes this difficulty. The competimers are short sequences homologous to 18 s rRNA primers but their 3' end is blocked, therefore they cannot be amplified by the Taq polymerase. The competimers (homologous to 18 s rRNA primers) compete with the cDNA of 18 s rRNA for binding with the 18 s rRNA primers. Thus, the use of competimers along with the 18 s rRNA primers reduce the amplification of the 315 bp fragment of 18 sRNA PCR product during PCR. Therefore the ratio of the primer to competimer determines the amount of 315 bp fragment of 18 sRNA during a PCR (Ambion inc. Tx, USA).

The internal standard 18 s rRNA primers and competimers were mixed in appropriate proportions (Table 9) to obtain the respective ratio. The optimum primer to competimer ratio to be used as an internal standard for each candidate gene had to be identified. This was determined by performing PCR for the gene with varying 18 s rRNA primers to competimer ratios (3:7, 2:8, 1:9). To each 20 µl PCR reaction tube, 1.6 µl of the appropriate 18 s rRNA primers to competimer ratio mix were added and PCR was performed at respective annealing temperatures. The PCR products were run on a 1.2% agarose gel.

Relative Quantitative RT-PCR

Single-stranded cDNA served as the template for relative quantitative RT-PCR. The designed gene specific primers with optimized annealing temperatures, PCR cycle numbers and 18 s rRNA primers to competimers ratio were used to determine the differential gene expression levels of C4H. Each relative quantitative RT-PCR mix contained one unit of Master Taq polymerase (Eppendorf, Brinkmann instruments inc., Canada); 2 µl of the single stranded cDNA template, 2 µl of PCR reaction buffer (10×) containing 100 mM Tris-HCl, pH 8.3; 15 mM $MgCl_2$; 500 mM KCl; 1% Triton X-100; 2 µl Taqmaster (5×PCR enhancer), 200 µM of each dNTP; 0.5 µM of upstream and downstream primers (specific for each selected candidate gene); 1.6 µl of optimized 18 s rRNA primers and competimers mix (Table 9) and the final volume was made up to 20 µl. PCR was done with initial denaturation at 95° C. for 2 minutes, followed by optimized cycles of denaturation at 95° C. for 45 seconds, annealing (temperature varies for each primer pair) for 45 seconds, extension at 72° C. for 45 seconds and a final extension at 72° C. for 7 minutes. The PCR product was examined on 1.2% agarose gel.

Quantification of Differential Gene Expression

The relative quantitative RT-PCR products were run on an agarose gel and the intensities of the bands were measured using the Labworks™ software (UVP Inc., Upland, Calif., USA). Maximum pixel intensities were measured for each relative quantitative PCR reaction. There should be two bands present on a single lane, one band represents the amplified candidate gene specific fragment and other the 315 bp fragment of the internal standard (18 s rRNA fragment). A blank reading of maximum pixel density with no band was also measured for each gel. The maximum pixel density readings of both bands were taken and subtracted by the maximum pixel density of the blank. The absolute measurement of gene expression level was calculated using Equation 1 given below.

$$\text{Gene expression level} = \frac{\text{Target gene pixel density} - \text{Blank}}{\text{Internal standard pixel density} - \text{Blank}} \times \text{Internal standard ratio}$$

Equation 1: Equation used to normalize the gene expression data obtained in maximum pixel intensities.

Measurement of Chlorogenic Acid and Citric Acid Contents

Fresh potato tuber samples were used for measuring chlorogenic acid and citric from tubers. Two repeated measurements for chlorogenic acid and citric acid were taken for each tuber sample.

1) Extraction of Organic Acids from Tubers

The potato tubers were washed and peeled with a vegetable peeler to remove all skin. Any bruising or rotten spots were removed using a small paring knife. One centimeter outer layer tissue was used and each tuber was chopped into small pieces. The chopped pieces were blend in a food processor for about 2 minutes. Accurately 25.000 g (±0.001 g) of the blended tuber was weighed in a beaker. To the blended tuber, 50 ml of extract solution (70% methanol) was added and mixed for 5 minutes on the magnetic mixer. The sample was then filtered through Whitman No.2 filter paper using a Buckner filtration set up. The filter paper was washed with 50 ml of 70% methanol into the original beaker. The sample slurry was registered and pooled together with the previous filtrates. One milliliter of the extract was pipetted into an acid wash. The sample was then dried using nitrogen evaporator at 40° C. The dry sample was stored at −20° C. until analyzed by HPLC.

2) HPLC Analysis

The sample stored in −20° C. was re-dissolved in 1 ml of mobile phase (2 mM potassium phosphate buffer, pH 2.7) by overtaxing and brief sanitation. The sample was then filtered through a 0.22 µm syringe filter. Twenty microliters of the sample was injected into the LKB (Bromma) HPLC. The HPLC was connected to a variable wavelength detector and a spectra-physics SP4290 integrator.

For chlorogenic acid (CgA), the mobile phase was 15% acetonitrile in 20 mM potassium phosphate buffer (pH 2.7). The sample was run on an isocratic run at 0.75 ml/minute for 20 minutes. The absorbance was measured at 325 nm. For citric acid (CA), the mobile phase was 2 mM potassium phosphate buffer (pH 2.7), with the flow rate of 0.75 ml/minute on an isocratic run. The absorbance was measured at 230 nm.

Experimental Design

Figure 5:
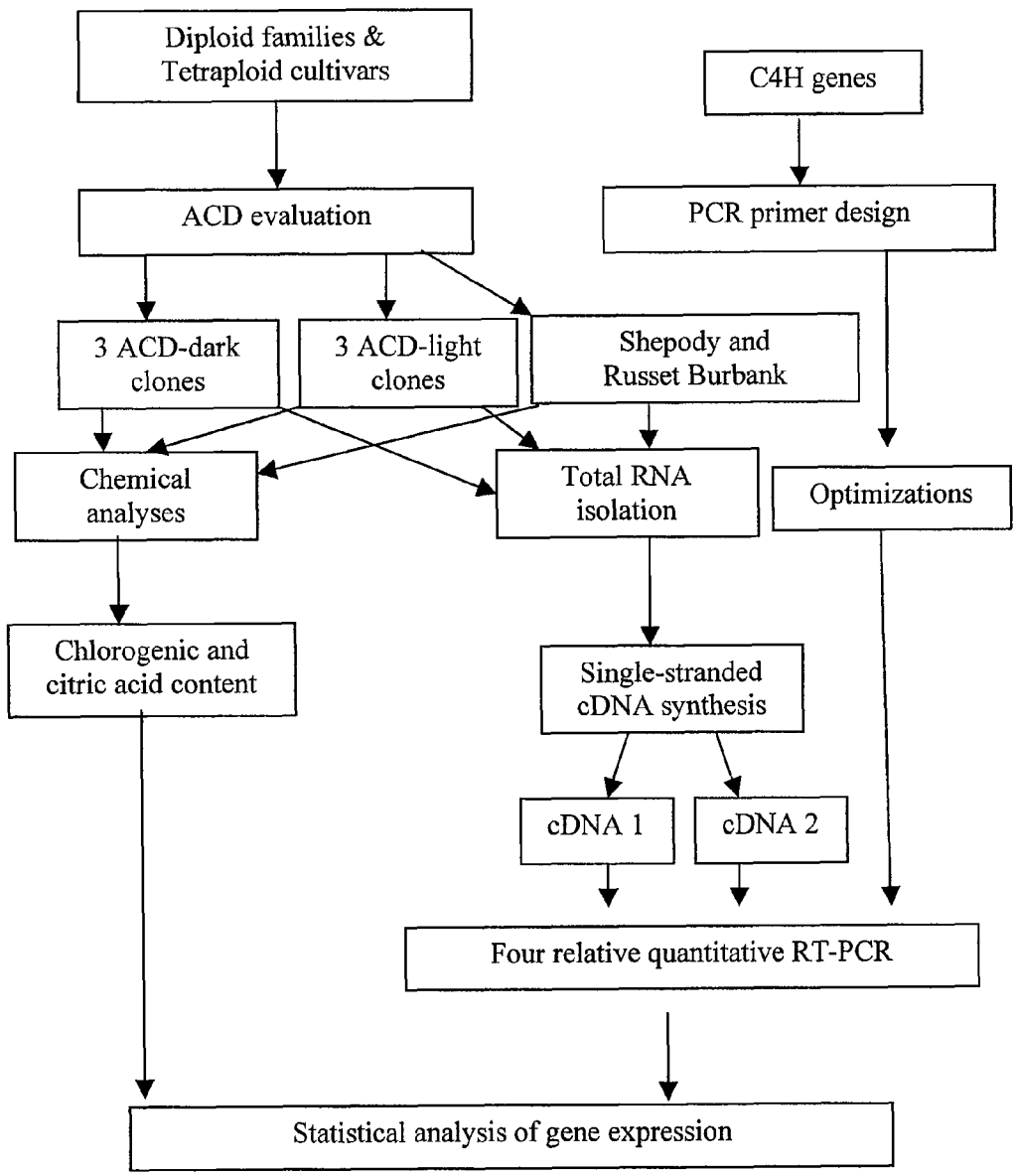
FIG. 5: Schematic representation of the methodology followed to achieve the objectives in Example 2.

The experimental design of this study has two different sections: 1) for differential gene expression analysis using relative quantitative RT-PCR and 2) for chemical content measurements, such as chlorogenic acid (CgA), citric acid (CA), and chlorogenic acid to citric acid ratio (CgA:CA). A schematic representation of the experimental design is given in FIG. 5.

The RNA samples from the selected ACD dark or light samples of each diploid families (13610-T and 13395-B) were pooled together for differential gene expression analysis using relative quantitative RT-PCR. Two separate reverse transcription reactions for single-stranded cDNA synthesis were performed using pooled ACD dark or ACD light RNA samples individually for each diploid family (13610-T and 13395-B). From each single-stranded cDNA sample obtained, two relative quantitative PCR experiments were carried out. Therefore, there were four individual relative quantitative PCR experiments carried out. Similar arrangement was done for the differential gene expression of C4H in the tetraploid cultivars Shepody and Russet Burbank. All the four individual relative quantitative PCR experiments were considered as four replications in this study.

Chlorogenic acid, citric acid and chlorogenic acid to citric acid measurements for all the diploid families (13610-T and 13395-B) and tetraploid cultivars (Shepody and Russet Burbank) were determined twice, individually for each selected tuber sample. The CgA, CA and CGA:CA measurements of selected ACD dark or light tubers were considered as replications for ACD dark or light clones in this study.

Statistical Analysis

1) Differential Gene Expression Analyses

The pixel density values obtained from four individual relative quantitative RT-PCR analyses were normalized separately using the Equation 1. The statistical analyses of the normalized gene expression data was done in two ways. First the fold increase or decrease in the expression of the candidate in the dark clones against the light clones was analyzed using students t test. Secondly, significant differences in the candidate gene expressions among the dark and light clones of each family and tetraploid cultivars were analyzed individually using one-way ANOVA. The four individual PCR experiments carried out from two separately synthesized single-stranded cDNAs were assumed as four replications of an experiment. The statistical analyses were carried out only for the data set that achieved normality. All the significant differences among the means were found at p<0.05.

2) Statistical Analyses on Chemical Analyses

Significant differences in the concentration of CgA, CA, and CgA to CA ratio among the dark and light clones of each family and tetraploid cultivars were analyzed individually using one-way ANOVA. The concentration of CgA, CA, and CgA to CA ratio obtained from each clone of dark or light were pooled together for each family. This pooled chemical data was assumed to be replicated values of the dark or light sample of that family. The statistical analyses were carried out only for the data set that achieved normality at p>0.1. All the significant differences among the means were found at p<0.05.

Results and Discussion

ACD Evaluation

Two diploid families, 13610-T and 13395-B, and two tetraploid cultivars, Shepody and Russet Burbank, were evaluated for their ACD in January, 2003 and January, 2004. The ACD levels for the tubers were determined using the mean pixel density values obtained by Labworks® digital imaging analysis software. ACD light tubers were determined by high pixel density values and ACD dark tubers determined by low pixel density values.

Many methods on evaluation of ACD in potato tubers have been reported, they include the use of visual evaluation, high performance liquid chromatography (HPLC), gas chromatography, UV spectrophotometry and nitrous acid (Hughes 1962; Chubey and Mazza, 1983; Siciliano et al., 1969; Griffiths et al., 1992). The ACD evaluation methods involving HPLC and gas chromatography are time consuming. The visual evaluation of ACD, requires proper standards to eliminate the subjectivity of the evaluator. Also some of the methods were unreliable as they analyze only a small portion of the tuber tissue. After-cooking darkening was evaluated using digital-imaging system in this study (Wang-Pruski and Tarn, 2003). The evaluation of ACD of potato tubers using the digital-imaging, in comparison to the earlier methods is fast, simple, accurate and consistent. The digital imaging analysis approach allowed the entire surface of the tuber to be analyzed; thereby any internal variation was taken into account. ACD evaluation was carried out using 2 tubers (4 halves) from each sample. The entire ACD evaluations for all the families, Shepody and Russet Burbank were performed by the same lab technician for the two year (2003 and 2004) period, which reduces potential manual error.

Figure 6:
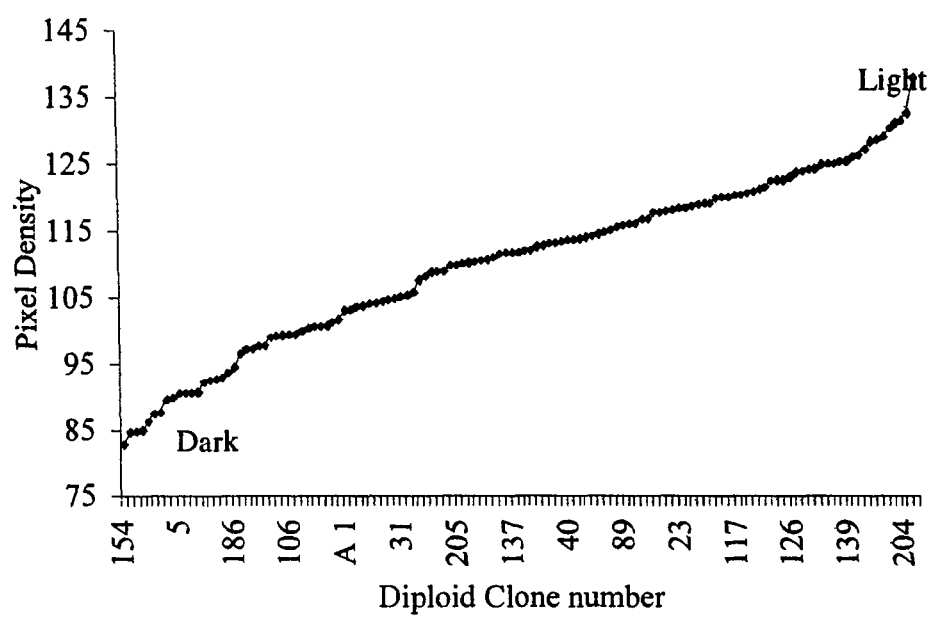
FIG. 6: Graph showing the pattern of ACD distribution among 129 clones of family 13610-T.
Figure 7:
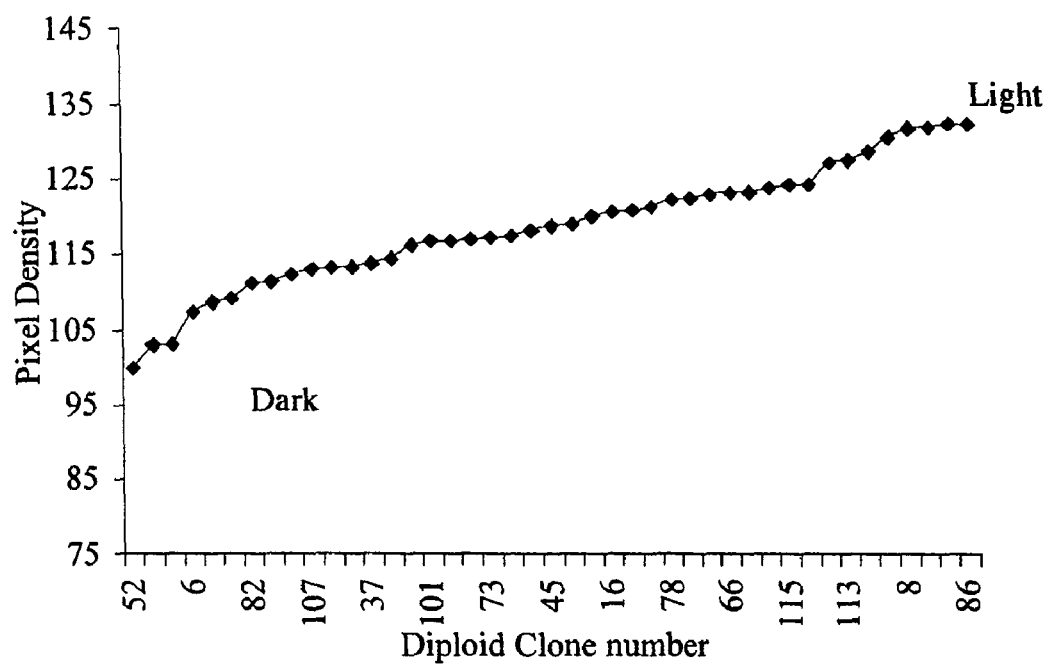
FIG. 7: Graph showing the pattern of ACD distribution among 43 clones of family 13395-B.

The distributions of the ACD among the clones of are shown in the FIG. 6 and FIG. 7, respectively. The distribution of ACD was similar in family 13610-T and 13395-B. In the family 13610-T, the pixel densities of the darkest clones were 82.07 and the pixel densities of the lightest clones were 134.48, respectively (Table 10). Family 13395-B did not show as wide a distribution pattern as 13610-T, but segregated well for ACD. The pixel density of the darkest clone in family 13395-B was 98.52 and the lightest clone had a pixel density reading of 132.41 (Table 10).

After-cooking darkening was evenly segregated among the progenies of the diploid families in this study. The segregation data showed that diploid family 13610-T had a more wide range of segregation (Table 10) than the 13395-B family (Table 10) (Wang-Pruski, unpublished).

Sample Selection

The clones were selected based on their ACD values of both January 2003 and January 2004. The ACD dark sample groups contained clones that showed very high ACD levels in both years; the ACD light group contained clones that showed very low ACD levels in both years. Three clones with the lowest or the highest pixel density readings in both January, 2003 and 2004, from the families 13610-T were selected (Table 11). Similarly two clones each with lowest and highest pixel density reading in both January 2003 and 2004 was selected in family 13395-B. The pixel density values of ACD dark and light clones selected from the families 13610-T and 13395-B with their respective clone numbers are tabulated in Table 11. The two tetraploid cultivars selected were Shepody and Russet Burbank in the same table. The ACD measurements were performed for the two cultivars as well.

Total RNA Isolation

Figure 8:
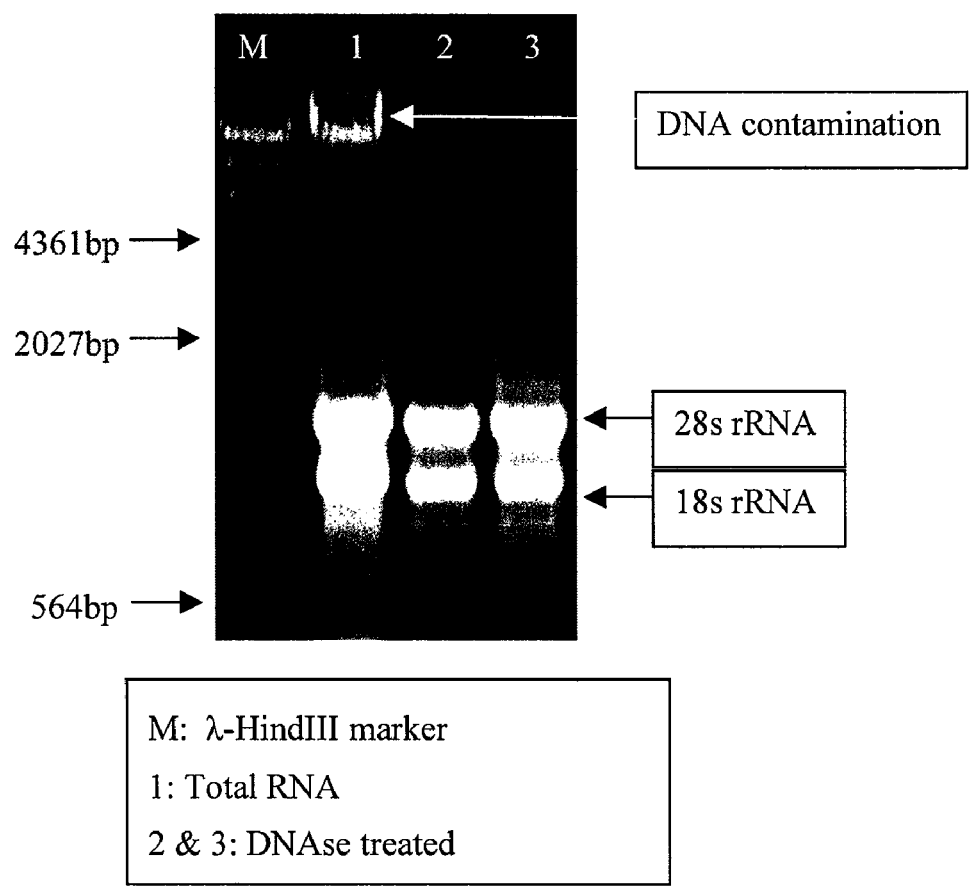
FIG. 8: Total RNA isolation after DNAse treatment and phenol chloroform extraction.

Total RNA was isolated from the frozen tuber samples based the protocol given by Singh et al (2003). The quality of the isolated total RNA was tested on a 1.0% agarose gel (FIG. 8). FIG. 8 shows the total RNA with two ribosomal RNA (rRNA) bands, one for 28 s rRNA and another for 18 s rRNA. The intensities of both the bands were in the ratio of 2:1, and there was no visible degradation of RNA (Lane 1; FIG. 8). The isolated total RNA was treated with DNase and extracted using phenol:chloroform as previously described. The DNAse treatment efficiently removed the DNA contamination found in the total RNA isolation (Lane 2, 3; FIG. 8). The concentration of the isolated total RNA was calculated by the Labworks™ software using the known concentration of the λ-Hind III marker bands. About 20 to 25 µg of total RNA was isolated from 300 mg of ground potato tissue. The isolated total RNA was used for single-stranded cDNA synthesis.

Single-Stranded cDNA Synthesis

Figure 9:
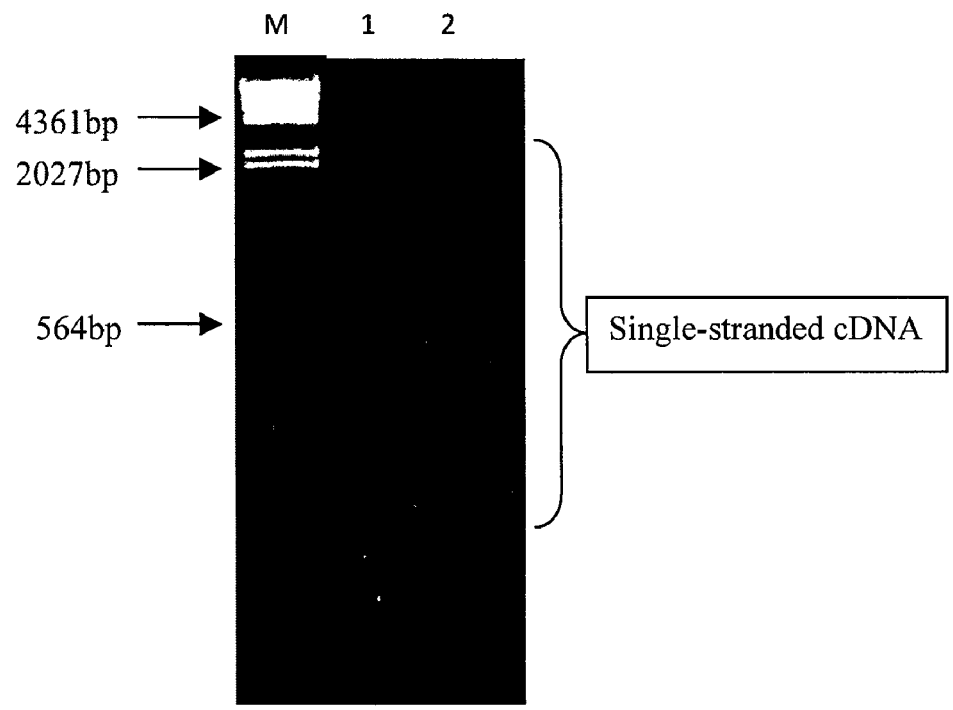
FIG. 9: Single-stranded cDNA synthesis from isolated total RNA using AMV reverse transcriptase and random primers.

Single-stranded cDNA was synthesized from the pooled total RNA from dark or light samples of 13610-T and 13395-B by reverse transcription (FIG. 9). The total RNA from the dark or light clones of the diploid families was pooled together in single-stranded cDNA synthesis for use in differential gene expression analysis. Pooling RNA from similar samples have been proven to be more effective that using them separately (Kendziorski et al., 2003; Xuejun et al., 2003). RNA samples are pooled together in microarray analyses to reduce the cost of the experiment and also avoid the biological variation (Kendziorski et al., 2003). Gene expression measurement by RT-PCR in individual samples shows that the variability in the measurements is due to the biological and technical variability. In the case of RNA samples pooled together the variability observed in RT-PCR measurements are only due to experimental variability (Kendziorski et al., 2003). Investigations on statistical properties of RNA pooling using data from real experiments and computer simulations, showed appropriate pooling of biological samples is statistically valid and more efficient for microarray experiments (Xuejun et al., 2003).

The pooled total RNA samples of dark or light samples of diploid families and total RNA from Shepody and Russet Burbank were reverse transcribed to single-stranded cDNA using random primers. Random primers are used as AMV reverse transcriptase can reverse transcribe both rRNA and messenger RNA (mRNA). The reverse transcribed rRNA was required for the use of 18 s rRNA primers which were used as an internal standard for relative-quantitative RT-PCR. The quality of the synthesized single-stranded cDNA was determined by visualization on 1.0% agarose gel using gel electrophoresis (FIG. 9). The quality appeared to be satisfactory as it had an even smear between 5000 bp to 500 bp. The cDNA samples were quantified by the calculating the pixel density area of the cDNA smear on the gel against the λ-Hind III marker bands using Labworks™ software. The differential analyses of candidate genes were carried out using ACD dark or light single-stranded cDNA with appropriate candidate gene specific primers and internal standards.

Determination C4H Specific Primers

The C4H specific primers were designed using Primer3 software for the nucleotide sequences of the candidate gene cinnamic4 hydroxylase (C4H). The full length cDNA sequences identified from example 1 from potato was used for designing primers (Table 12). The gene specific primers target the 514 bp fragment of C4H. The nucleotide sequence of the chosen set of primers for the C4H gene is given in Table 13. These gene specific forward and reverse primers were used in relative quantitative RT-PCR for determining the differential gene expression analysis.

Optimization for Relative Quantitative RT-PCR

Relative quantitative RT-PCR is a semi-quantitative, medium throughput technique for differential gene expression analysis on a small scale. The relative quantitative RT-PCR technique was selected in this study for its simplicity and reproducibility compared to other differential gene expression analysis methods such as Northern hybridization, competitive RT-PCR, or real-time RT-PCR. One major issue of relative quantitative RT-PCR is that several optimizations have to be performed for obtaining reproducible and valid results. Some of the parameters to be optimized for relative quantitiative RT-PCR are: to determine the linear range sensitivity of the imaging device, optimal annealing and PCR cycle numbers and use of an optimized internal standard (18 s rRNA primers to competimers ratio in this study).

1) Linear range sensitivity for imaging device

Figure 10:
FIG. 10: Intensities of PCR products amplified after 27 cycles with varying initial copies.
Figure 11:
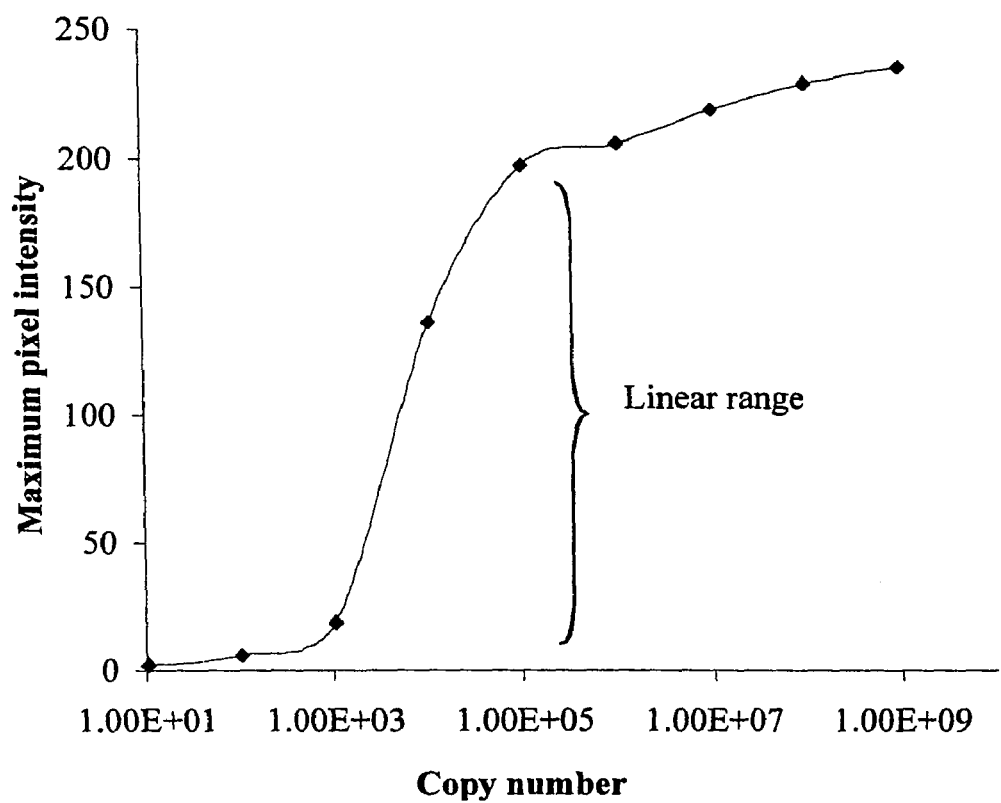
FIG. 11: Graph showing the linear range of the PCR cycle showing sensitivity of the imaging device based on the gel picture shown in FIG. 10.

The threshold limit of the imaging device to differentiate between two white pixels is determined by its linear range sensitivity. A PCR with increasing copy numbers of the pGEN4T vector containing C4H PCR product was performed. The maximum pixel densities of the amplified bands were measured using the UVP imaging device (FIG. 10). A graph (FIG. 11) was plotted for intensities of the bands in FIG. 10 against the initial copy numbers of the plasmid. The graph shows an initial phase followed by the exponential phase and finally a plateau phase. The lag phase shows the minimum level of sensitivity of the imaging device to identify the band intensity. The plateau phase shows the maximum level of sensitivity of the imaging device. The linear range of sensitivity of the imaging device is the exponential phase was between 6 pixels to 215 pixels (FIG. 11).

2) Annealing temperature and PCR cycle number

The optimum annealing temperature at which the designed primers can efficiently bind to the target fragment was determined. The annealing temperature for C4H specific primers was 53° C.

Figure 12:
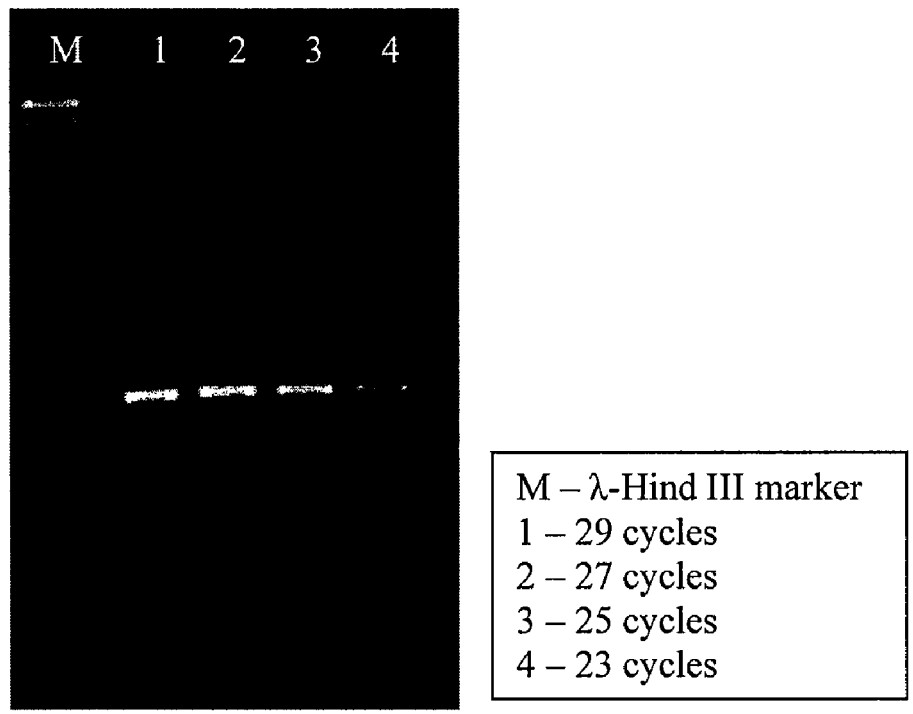
FIG. 12: Gel electrophoresis showing increasing intensities of the PCR products at different PCR amplification cycles.

The threshold limit for the PCR cycle was determined by stopping the PCR at various cycles ranging from 23 to 29. FIG. 12 shows the amplified PCR products at different cycles. The maximum pixel densities of the amplified products were measured and the cycle number 27 was found to be optimum for all the candidate genes tested. The intensity of the amplified DNA product at cycle 27 (178.0 maximum pixel density) was within the linear range of the sensitivity of the imaging device.

3) Optimization of 18 s rRNA internal standard

The optimal primer to competimer ratio for each candidate gene, to be used as an internal standard was determined. Polymerase chain reactions for the candidate gene (C4H) with the 18 s rRNA primer to competimer ratio (1:9), was carried out at respective optimal annealing temperatures. The bands were visualized using UVP imaging device to determine the intensity of the two bands on a single lane. The first band represented the PCR product of the target gene with respective fragment size and the other represented the 315 bp PCR product of the 18 s rRNA internal standard. The ratios of the intensities of both the bands were measured The relative quantitative RT-PCR uses 18 s rRNA as an internal control for normalizing the gene expression data obtained. The 18 s rRNA internal control helped in normalization of gene expression that accounted for any tube to tube variation caused by variable RNA or cDNA quality, inaccurate quantitation or pipetting. The use of 18 s rRNA primers and competimers from Ambion gave reproducible results once the ratios were optimized for different genes. Competimers along with the 18 s rRNA primers increased the possibility of identifying differential gene expression profiles of extremely rare mRNA transcripts. The 18 srRNA primers to competimer ratio helped in determining the true gene expression of the candidate genes using the Equation 1.

The Equation 1 was used to normalize the gene expression levels based on the 18 s rRNA internal control. The normalized gene expression values obtained using Equation 1 can be directly correlated to the level of gene expression in the samples. The pixel density values of the internal controls for the dark or light samples of respective candidate gene in a PCR experiment was similar. This validates the efficiency of the internal control used.

The optimization of the annealing temperatures for the designed gene specific primers, PCR cycle numbers for differential expression of candidate genes, linear range sensitivity of the imaging device and the 18 s rRNA primer to competimer ratios of the internal standard were important for differential gene expression analysis using relative quantitative RT-PCR. These optimizations validate the results obtained, and account for reproducibility. Using these optimizations, the differential gene expression analysis was performed on the selected dark and light clones of diploid families and the tetraploid cultivars.

Differential Expression of C4Hgene and its Relationship to ACD

In this study, Families 13610-T, 13395-B and Russet Burbank/Shepody were selected as a model to study C4H gene expression and its relationship to ACD. This section focuses on the results and discussion of ACD data analysis, chemical content analysis and differential expression of C4H for the family 13610-T. The relationships of chemicals such as CgA, CA, and CgA to CA ratio are correlated to ACD. The differential expression of C4H gene is correlated to its respective chemical products and finally to ACD.

1) ACD data analysis

The ACD values of the selected dark and light clones of the families of 13610-T and 13395-B were measured as shown in Table 14.

2) Chemical data analysis

The concentration of CgA and CA concentration in the selected dark and light clones of families of 13610-T and 13395-B were measured using HPLC. One way ANOVA analyses was performed on the CgA, CA contents, and CgA to CA ratio in the dark and light clones separately. The mean concentrations of CgA, CA, and CgA to CA ratio in the selected tuber clones are tabulated in Table 15. The concentration of CgA was higher in the dark clones of family 13610-T than that of the light clones.

The CA concentration in the light clones of family 13610-T was higher than that of the dark clones. The CgA to CA ratio also was found to be higher in the dark clones of 13610-T compared to the light clones.

The results show that the CgA in the dark clones of family 13610-T was significantly higher than that of the light clones (P=0.046). In family 13610-T, the mean CgA content in the dark clones was 0.49 mg $100^{-1}$ g and the mean CgA content in the light clones was 0.24 mg $100^{-1}$ g. The statistical analysis of CA concentration among the dark and light clones of family 13610-T are tabulated in Table 15.

The results show that the CA content in the dark and the light clones are not significantly different (P=0.617). The mean CA concentration of the dark clones and the light clones of family 13610-T are 808.15 mg $100^{-1}$ g and 833.47 mg $100^{-1}$ g. The statistical results of CgA to CA ratio are given in Table 15. The results show that the CgA to CA ratio in the dark clones of family 13610-T was significantly higher than that of the light clones (P=0.049). The mean CgA to CA ratio of the dark clones and the light clones were $6.05 \times 10^{-4}$ and $2.95 \times 10^{-4}$, respectively. Similar results were also reported by Hughes and Swain (1962b). Hughes and Swain (1962b) from their in-vitro experiments on CgA, CA and CGA:CA found that CgA and CgA to CA ratio to play an important role in ACD. They also found no significant changes in the citric acid levels among the tubers they analyzed.

3) Relative Quantitative RT-PCR

Relative quantitative RT-PCR was performed for the pooled ACD dark or light clones of the families 13610-T, 13395-B and Russet Burbank and Shpody. The relative quantitative RT-PCR was done separately for single-stranded cDNA from dark or light samples. Four separate PCR experiments (PCR1, PCR2, PCR3 and PCR4) were carried out for each gene from two separately synthesized single-stranded cDNA of dark or light samples. All the PCR experiments were carried out for 27 cycles.

Figure 20:
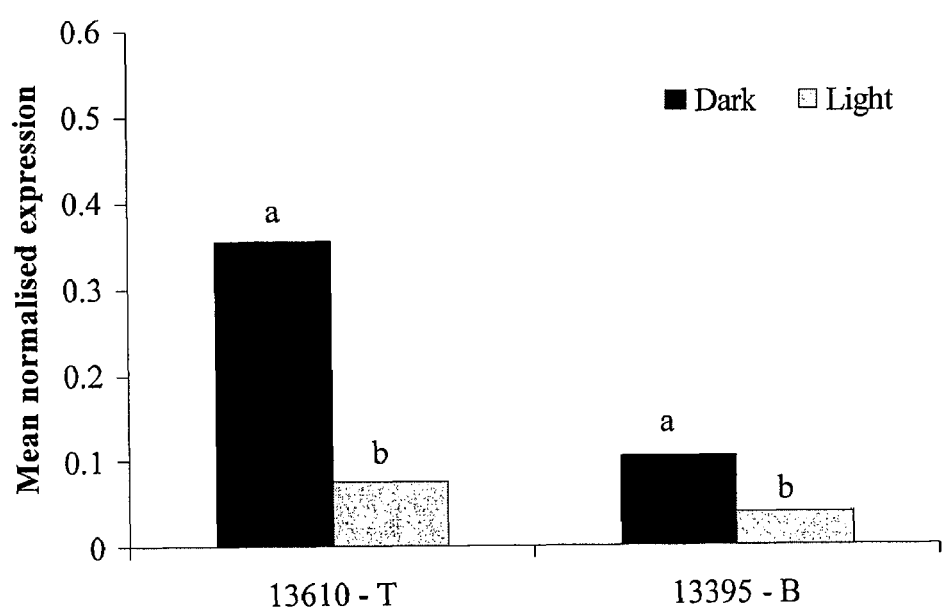
FIG. 20: Graph showing mean normalized C4H gene expression in ACD dark and light clones of the diploid families 13610-T and 13395-B. The significances were statistically analyzed using one-way ANOVA at $p<0.05$
Figure 21:
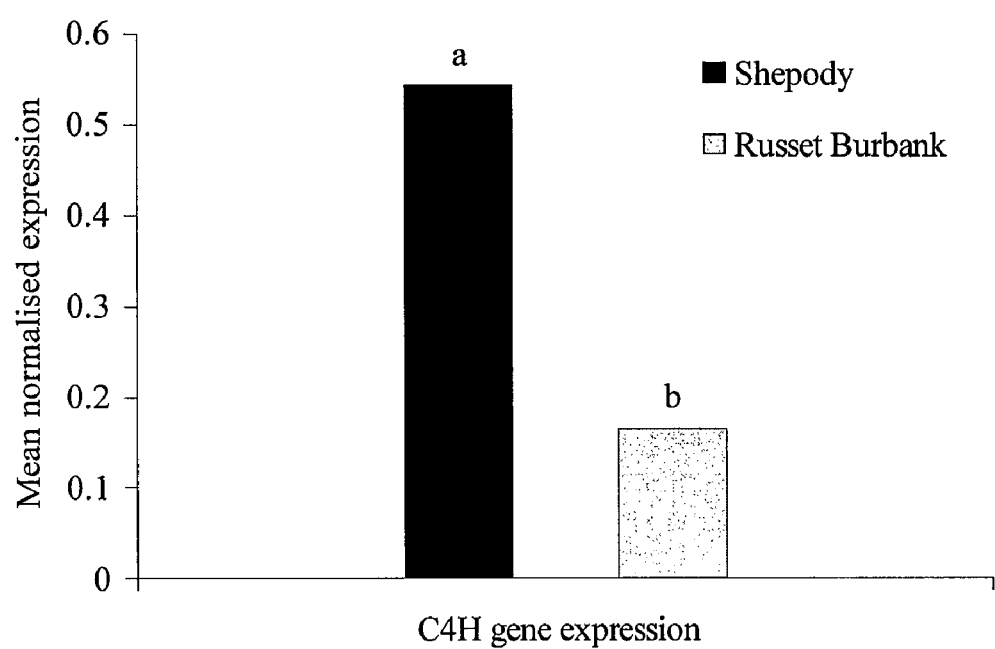
FIG. 21: Graph showing mean normalized C4H gene expression in Shepody and Russet Burbank. The significances were statistically analyzed using one-way ANOVA at $p<0.05$

The relative quantitative RT-PCR results obtained for the four PCR experiments are show in FIGS. 13 through 18. Each relative quantitative RT-PCR shows two bands: the amplification of the gene specific band of the candidate gene and the 315 bp internal standard amplified by the 18 s rRNA primers. The amplification of the internal standard differs according to the ratio of the 18 s rRNA primer and competimer used. The maximum pixel densities (MPD) for the two bands and a blank reading were measured. The normalized gene expression level for each PCR was calculated using Equation 1. The maximum pixel densities and the normalized gene expression are illustrated in Tables 16, 17, and 18. The graphical representation of the normalized gene expression levels of the C4H are shown in FIGS. 19, 20 and 21.

4) Differential cinnamic acid 4-hydroxylase gene expression

Figure 13:
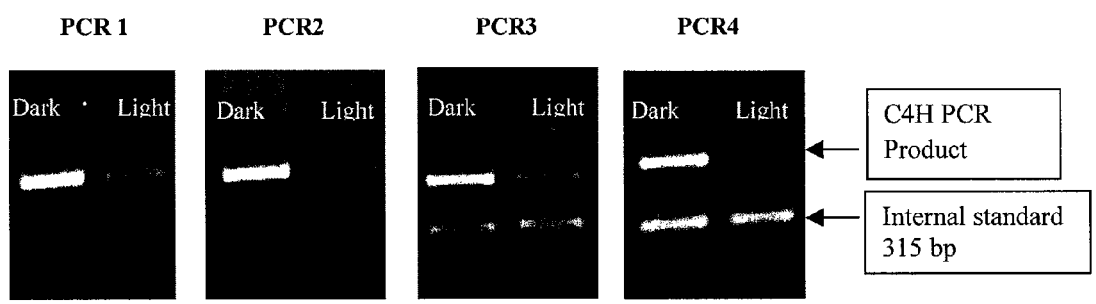
FIG. 13: Gel electrophoresis showing C4H gene expression profiles along with internal standard in dark and light clones of family 13610-T. PCR 1 to PCR 4 are the four individually repeated PCR experiments.
Figure 14:
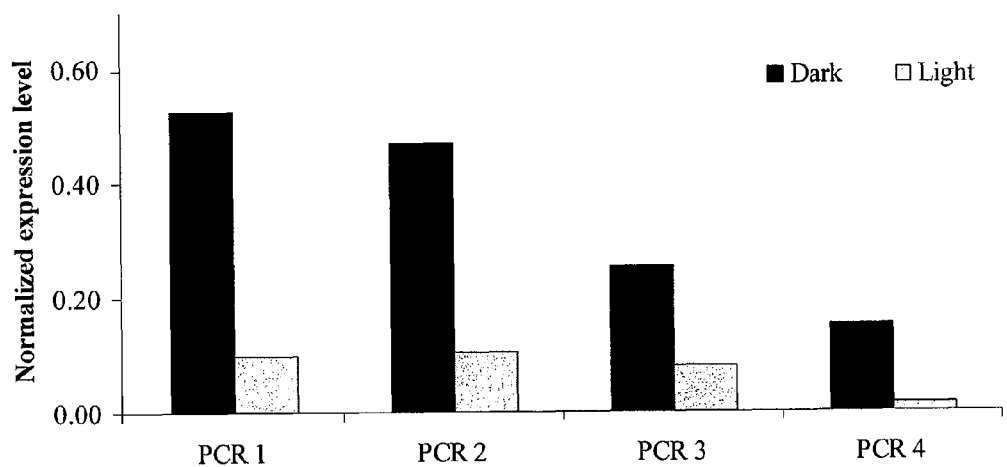
FIG. 14: Normalized gene expression level of four repeated PCR experiments for C4H gene in ACD dark and light clones of family 13610-T.
Figure 15:
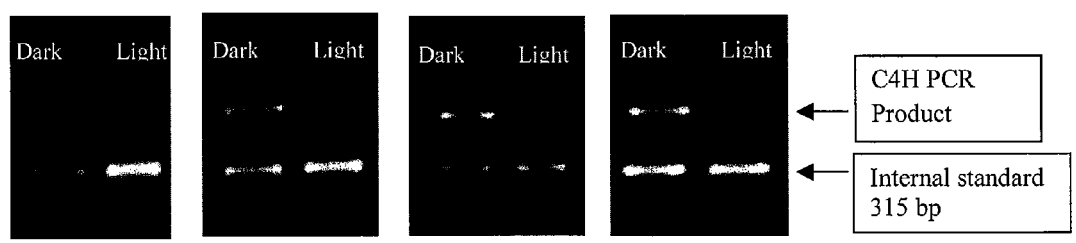
FIG. 15: Gel electrophoresis showing C4H gene expression profiles along with internal standard in dark and light clones of family 13395-B. PCR 1 to PCR 4 are the four individually repeated PCR experiments.
Figure 16:
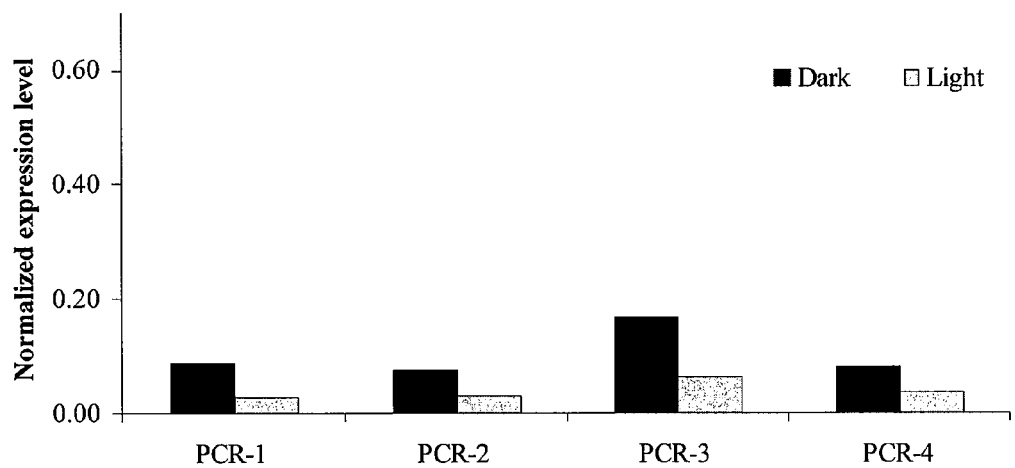
FIG. 16: Graph showing normalized gene expression level of four repeated PCR experiments for C4H gene in ACD dark and light clones of family 13395-B.
Figure 17:
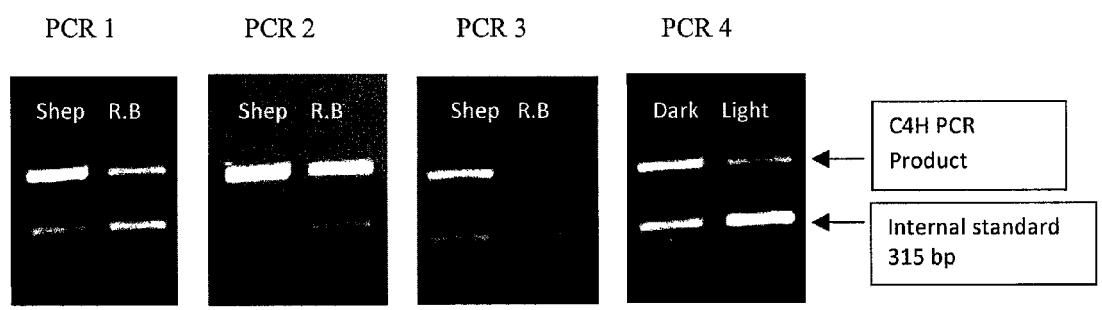
FIG. 17: Gel electrophoresis showing C4H gene expression profiles along with internal standard in cultivars Shepody and Russet Burbank.
Figure 18:
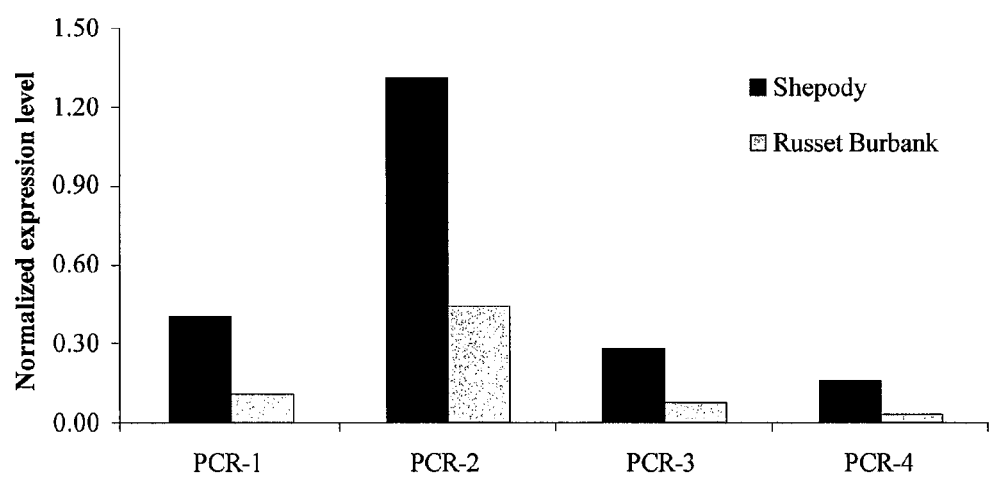
FIG. 18: Graph showing normalized gene expression level of four repeated PCR experiments for C4H gene in cultivar Shepody and Russet Burbank.

The differential expressions of cinnamic acid 4-hydroxylase (C4H) gene between dark and light samples of family 13610-T are shown in FIGS. 13 and 14. It contains the gel pictures of four PCR experiments. The C4H gene specific PCR product of about 514 bp was detected consistently in all the four PCR experiments along with the 315 bp internal standard. The internal standard ratio of the 18 s rRNA primers and competimers used for C4H gene differential analysis is 1:9. The maximum pixel densities (MPD) of the bands are given in Table 16. The table shows the normalized gene expression levels of C4H gene calculated using the Equation 1. The normalized gene expression values of the dark clones are consistently higher than that of the light clones in the family 13610-T (FIG. 14).

Figure 19:
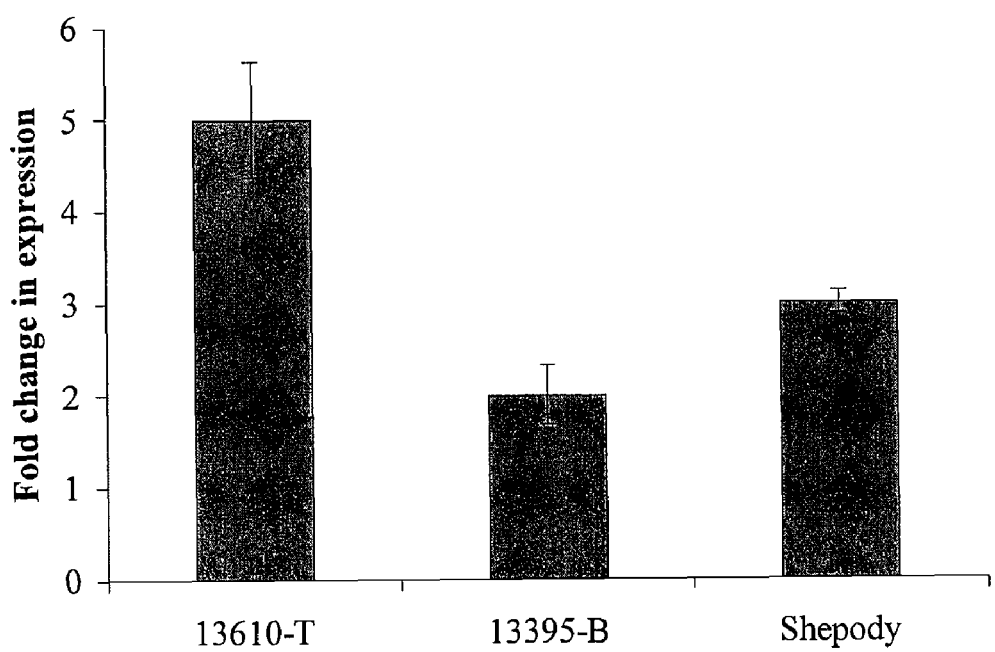
FIG. 19: Graph showing fold changes in the expression of candidate genes in dark clones comparing to that of the light clones in family 13610-T and family 13395-B, and cultivars Shepody comparing to Russet Burbank. The numbers above the bars are the mean fold changes for the C4H gene. The error bars are the standard error mean calculated using students t test.

The C4H gene expression in the dark clones of family 13610-T was about 6 fold higher than that of the light samples, when the means of the normalized C4H gene expressions between dark and light clones were compared (FIG. 19). The four repeated PCR experiments showed a consistently higher expression of C4H gene expression in the dark samples compared to that of the light samples (FIG. 14). The one way ANOVA results on the normalized C4H gene expression levels of dark and light samples of family 13610-T are shown in FIG. 20. The results of the one-way ANOVA analysis on C4H gene expression showed that the dark samples of family 13610-T is significantly higher than that of the light samples (P=0.021). The highest mean normalized C4H gene expression was 0.36 for the dark samples and the lowest mean normalized C4H gene expression was 0.08 in the light samples (FIG. 20).

The C4H gene expression in the ACD dark clones of 13610-T was about 6 fold higher than the light clones (FIG. 19). This shows that in family 13610-T, ACD dark clones had high level of C4H gene expression and the ACD light clones of family 13610-T had low level of C4H gene expression. It was also be noted that the ACD levels between the dark and light clones were significantly apart in family 13610-T (Table 11). The normalized gene expression values of C4H gene were always higher in the ACD dark clones than that of the ACD light clones (Table 16). Therefore, it could be concluded that the C4H gene expression is always higher in the ACD dark clones and the expression of C4H gene was lower in the ACD light clones in this study.

One-way ANOVA was performed to study the significant differences between the C4H gene expression between the ACD dark and light clones (FIG. 20). The statistical analysis showed that the C4H gene expressions in the ACD dark clones of family 13610-T was significantly higher than that of the light clones (P=0.021). This shows that C4H gene was highly expressed in ACD dark clones of family 13610-T and the C4H gene expression in the ACD light clones was considerably lower. This correlates with the 6 fold increase in the C4H gene expression in the ACD dark clones of family 13610-T than that of the ACD light clones (FIG. 19). Cantle (2005) performed Northern hybridization analysis to determine C4H gene expression between ACD dark and light clones. She reported that ACD dark clone had higher C4H gene expression than that of the ACD light clone. Therefore it is evident that the C4H gene expression is significantly higher in the tubers with high ACD levels and the C4H gene expression is lower in tubers with low ACD levels.

The CgA and CgA to CA concentration in the dark clones of family 13610-T was also significantly higher than that of the light clones (Table 15). This shows that CgA and CgA to CA ratio are high in the dark clones compared to the light clones. Similar results were reported by Hughes and Swain (1962a, b). It is noted that the significant increase in the expression of C4H is followed by a significant increase in CgA in dark clones of family 13610-T. This shows that there is a strong correlation between the expression of C4H and CgA concentration in the tubers. C4H enzyme being an important enzyme in the phenylpropanoid pathway could possibly play an important role in the synthesis of CgA.

In this study, the relative quantitative RT-PCR data strongly correlated with the C4H gene expression to ACD at different levels. The fold increase of C4H gene expression also correlated with the difference in the ACD dark and light clones in the diploid families. C4H gene expression correlated with the CgA concentrations in the samples studies. From these observations, it can be concluded that C4H gene is a potential gene for regulating ACD levels in potato tubers.

Very similar data have been obtained from 13395-B and the two tetraploid samples (Tables 14, 15, 17, 18 and FIGS. 15, 16, 17, 18, 19, 20, 21). The data from samples for family 13395-B and the tetraploid cultivars have shown very similar gene expression patterns as 13610-T; the chemical contents of these samples also correlate with ACD in these samples.

Family 13610-T was selected as a model to study the relationship of candidate gene expressions and chemical contents to ACD. The ACD values of the dark and light clones selected were significant to provide enough information on ACD. The findings from this study support the hypothesis that CgA is the main chemical involved in ACD. Also the chlorogenic to CA ratio was found to play a major role in ACD. The CA did not show any relationship to ACD. These results support the findings of Hughes and Swain (1962a, b), Swiniarski (1968), Wang-Pruski et al. (2003). This confirms that the selected dark and light clones of family 13610-T served as a good model for studying ACD trait. Therefore, the use of these selected clones to study the differential expression of candidate genes will be appropriate.

This is the first study to report the differential expression of candidate gene C4H and its respective chemical product for the relationship to ACD.

The differential gene expression studies proved our hypothesis that the expression of C4H gene would be high in the clones with increased CgA levels. Our differential gene expression analysis results supported the findings of Landschutze et al (1995), Ma et al. (2001), Petit et al. (2002), Cantle (2005), Topley (2004), Niggeweg et al. (2004). This showed that the differential gene expression analysis using relative quantitative RT-PCR is an efficient tool for differential gene expression. The differential gene expression analysis indicated that C4H genes could be considered as potential gene candidates for ACD trait analysis.

Example 3

This experiment was to further exam the C4H gene expression levels in relationship to potato ACD using the most advanced real-time quantitative PCR technique.

Materials and Methods

Potato Samples:

Four diploid clones that shown lower or higher degree of ACD were selected in this study. They were two dark clones of 13610-T (family 13610 grown in Truro Nova Scotia Canada location), two light clones of 13610-T, two dark clones of 13610-B (family 13610 grown in Benton Ridge, New Brunswick, Canada location), and two light clones of 13610-B.

Real Time PCR Protocol:

A1 µl of gene specific forward primer and reverse primer was added to 25 µl of platinum SYBR green qPCR super mix with ROX. The volume was made up to 48 µl with water. After that, 1 µl of C4H gene standard was added to 24 µl of the PCR mix and the real-time PCR was carried out. The PCR reaction conditions are listed as following:

| Cycle 1: (1×) | |
|---|---|
| Step 1: | 50.0° C. for 02:00 |
| Cycle 2: (1×) | |
| Step 1: | 95.0° C. for 02:00 |
| Cycle 3: (35×) | |
| Step 1: | 95.0° C. for 00:15 |
| Step 2: | 53.0° C. for 00:30 |
| Steo 3: | 72.0° C. for 00:30 |

Data collection and real-time analysis enabled.

| Cycle 4: (1×) | |
|---|---|
| Step 1: | 72.0° C. for 05:00 |
| Cycle 5: (250×) | |
| Step 1: | 95.0° C. for 00:15 |

Decrease set point temperature after cycle 2 by 0.1° C.

Quantitatation of Gene Expression:
  P C4H gene expression was quantified using an internal standard Ubi3, a constitutively expressed gene in plants. The gene expression levels were calculated based on the method of Bio-Rad Laboratories, Inc. Real-Time PCR Application Guide, page 41. Cycle threshold (Ct) was used for the quantitation.

Figure 24:
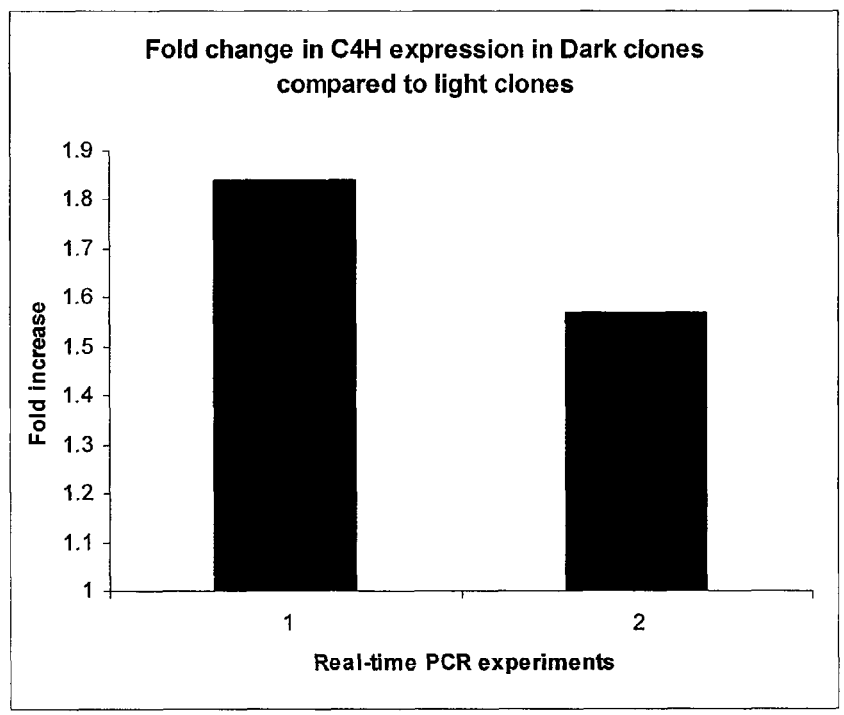
FIG. 24: Graph showing fold change in C4H expression in dark clones compared to light clones in 13610-T. The two individual experiments are marked as 1 and 2.
Figure 25:
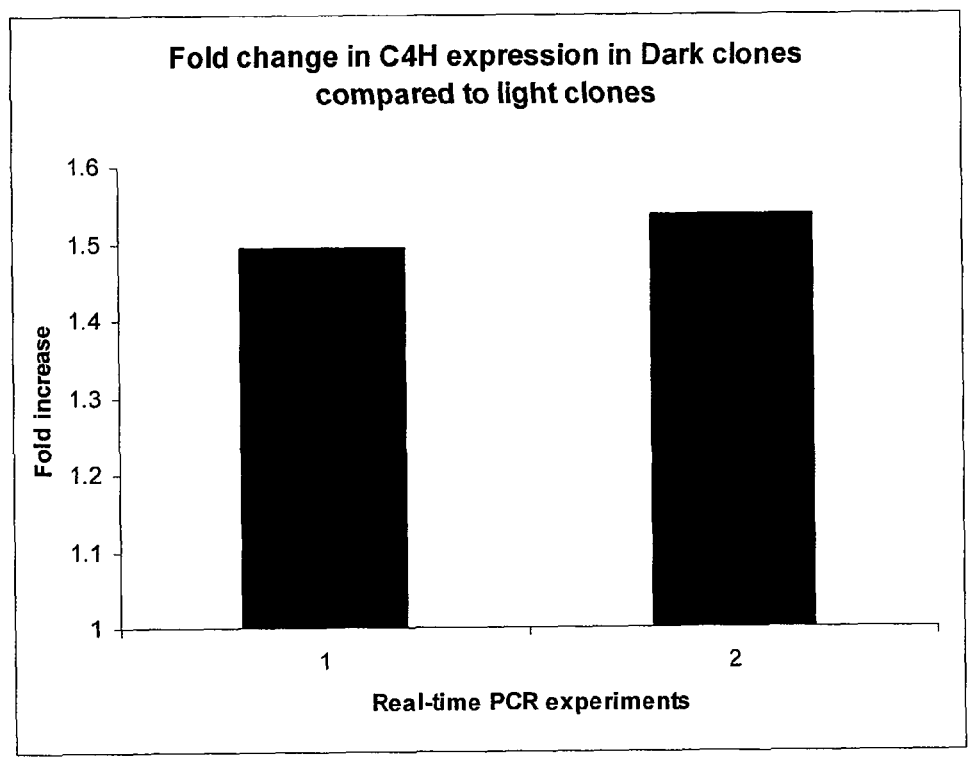
FIG. 25: Graph showing fold change in C4H expression in dark clones compared to light clones in 13610-B. The two individual experiments are marked as 1 and 2.

Results:

Table 19 and Table 20 summarized the PCR data as Ct for the C4H gene and the internal standard Ubi3 gene. The C4H gene expression levels in the dark and light clones in both 13610-T and 13610-B were calculated and fold changes are listed in Table 19 and Table 20 as well. These two independent experiments used samples that were different from the previous two Experiments (Experiment 1 and Experiment 2 in this document). The dark clones from 13610-T showed 1.84 and 1.57 fold higher C4H gene expression comparing to the ones of the light clones.). The dark clones from 13610-B showed 1.50 and 1.54 fold higher C4H gene expression comparing to the ones of the light clones. These fold changes were also illustrated in FIG. 24 and FIG. 25.

Example 4

This experiment demonstrated the work on inhibition of C4H gene expression in potato using RNAi technique. RNAi technique has recently been used to inhibit gene expression in wide range of organisms, including plants. Literatures in this regard can be found from Schattat et al. (2004), Susi et al. (2004), Agrawal et al. (2003), and Derek et al. (2003).

Inhibition of C4H gene expression experiment in potato has been carried out in the following two steps.

1. Generation of C4H Silencing Cassette

Figure 22:
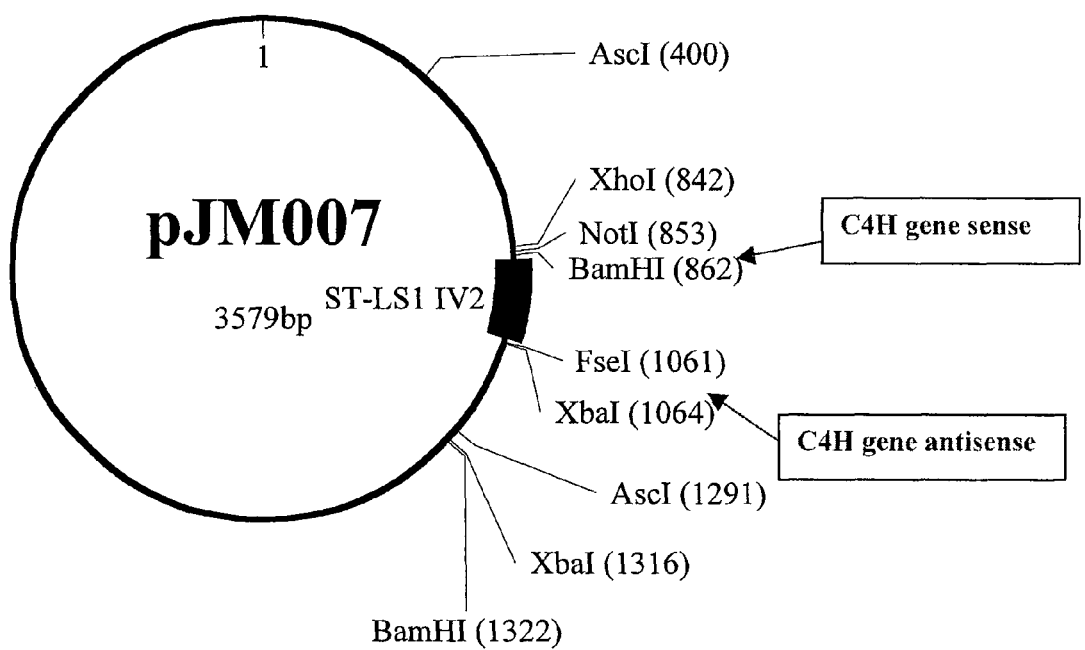
FIG. 22: A schematic of the RNAi construct for inhibition of C4H gene expression.
Figure 23:
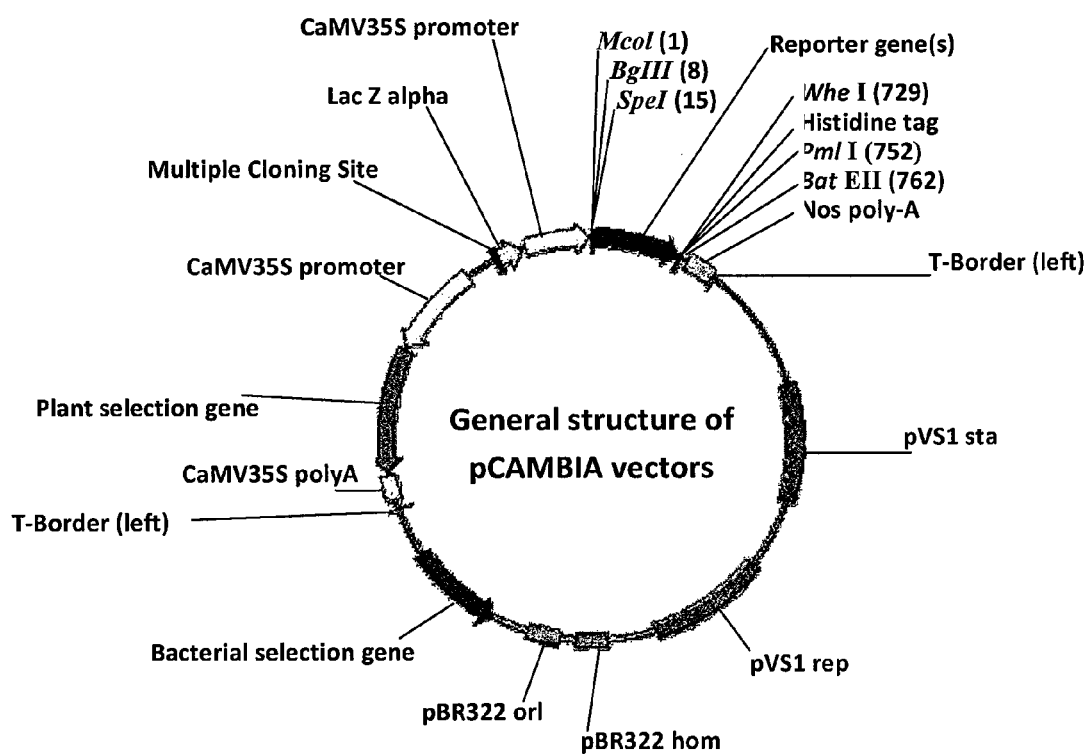
FIG. 23: A schematic of the vector pCAMBIA1302 for overexpression of the C4H gene where the gene is subcloned under the CaMV35S promoter between NcoI and BglII restriction sites.

The pJM007 (Schattat, et al., 2004, Plant Molecular Biology Reporter 22: 145-153) vector system was used for this study. It contained the second intron (IV2) of the ST-LS1 gene from potato. The full length and partial gene of C4H (the partial sequence of C4H, around 500 bp, comes form the 5' end of the gene) were used to generate two separate constructs. The sequence in sense orientation was ligated into the pJM007 at the right side of the ST-LS1 intron and the antisense on the right side. Therefore, the developed C4H RNAi cassette contains the sense sequence of C4H, ST-LS1 intron and the antisense sequence of C4H in order to produce the hairpin RNA with the intron in the middle as the loop, which will trigger the specific gene inhibition. The RNAi construct is shown in FIG. 22.

2. Plant Transformation (Method Listed Previously)

The above silencing cassettes were excised from pJM007 and cloned into the binary vector pGreenII0129. Electroporation was used to transfer the resulting constructs to *Agrobacterium tumefaciens* GV3101 (pMP90). Potato explants (cultivar Bintje) were transformed under the Agrobacterium mediation and selected on CSM (callus selective medium) containing 50 μg/ml of kanamycin. The transformed plants will be verified using PCR and Southern hybridization, and the gene specific antisense expression will be verified using RT-PCR method. Antisense activity will be further assessed and the biological assays will follow. Chlorogenic acid content will be evaluated in tubers when the plants are grown to full size. The degree of ACD in potato tuber will also be measured.

Example 5

Figure 26:
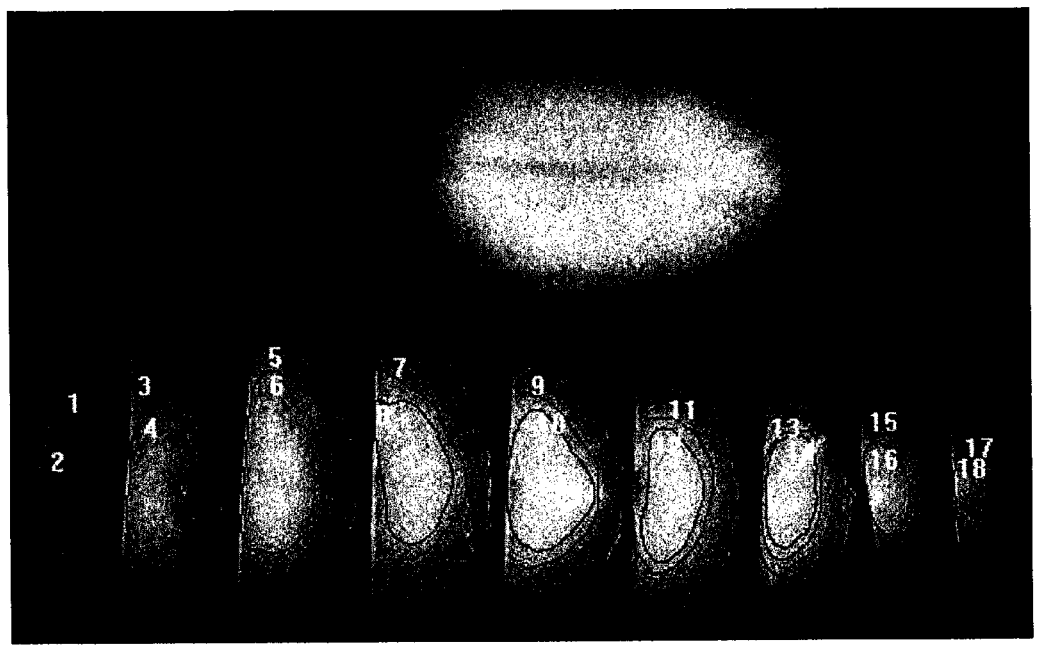
FIG. 26: Distribution of ACD in a tuber of cultivar Russet Burbank. A. The tuber was vertically cut into two halves. One half is displayed on the top, the other half was sliced into nine pieces and is displayed in sequence on the bottom. Interior areas and exterior areas were selected from each slice and numbered from 1-18. The areas with odd numbers represent exterior tissues; the areas with even numbers represent the interior tissues. B. Localization of the darkening levels of these 18 areas. The left is stem end, and the right is apical end of the tuber. The darkening levels from the exterior tissues are shown in blue broken bars and the interior tissues are shown in red bars. The ACD levels are generated based on the MRD data from area 1-18.
Figure 26:
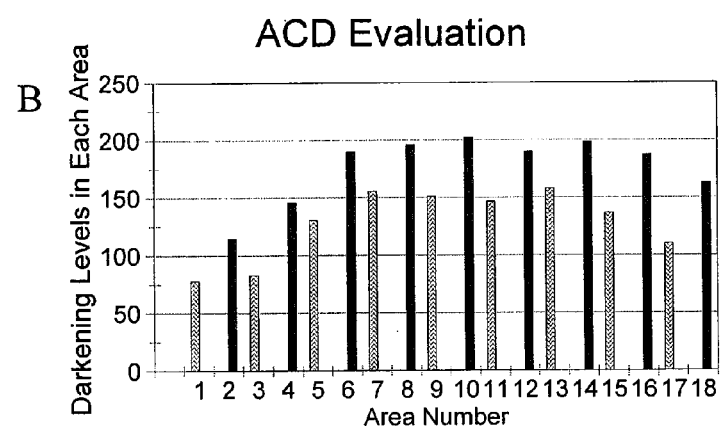

This experiment is to demonstrate that the chlorogenic acid levels in potato tuber is correlated with the degree of ACD in the different location of the tubers. This is based on our finding (Wang-Pruski, 2006) that degree of ACD is not evenly distributed. The degree of ACD at stem end of the tuber is always higher comparing to the apical end of the tuber. Similarly, the exterior of the tuber is always darker than the interior of the tuber (FIG. 26).

Table 21 shows the results of cholorogenic acid content measured by HPLC in different portions of potato tuber tissues (methods are identical as described previously). The results confirmed that the cholorogenic acid content is correlated with the degree of after-cooking darkening (ACD). This experiment was done using potato cultivar Russet Burbank, the most widely used French fry processing variety in North America. The stem end which has the highest ACD showed the highest content of chlorogenic acid. The ACD in the apical end is lower than that of stem end, the center region of the tuber has lower ACD compared to the tissues in the exterior region. All these ACD distribution patterns correlate with the content of chlorogenic acid. Since C4H is the key enzyme for chlorogenic acid biosynthesis, its gene expression will determine the content of chlorogenic acid in potato tubers.

TABLE 1

Sequences of designed primers for cloning of c4h by PCR*

| Primer ID | SEQ ID NO | Primer Sequence (5' to 3') | Tm (° C.) |
|---|---|---|---|
| AF AR | 7 | 5'-CCCCAGGTCCAATTCCA-3' | 60.25 |
|  | 8 | 5'-TTCAGGGGATGACACAACAG-3' | 59.52 |
| BF BR | 9 | 5'-CTGTTGTGTCATCCCCTGAA-3' | 59.52 |
|  | 10 | 5'-CCTCATTTTCCTCCAGTGCT-3' | 59.28 |
| CF CR | 11 | 5'-GGCCTTTCTTGAGGGGTTAC-3' | 59.94 |
|  | 12 | 5'-CCTCGTTGATCTCTCCCTTCT-3' | 59.83 |
| DF DR | 13 | 5'-GAAGGGAGAGATCAACGAGG-3' | 58.82 |
|  | 14 | 5'-TCACAGCCTGAAGGTATGG-3' | 57.16 |
| EF ER | 15 | 5'-CCACTGGAAGAAACCTGAAG-3' | 57.36 |
|  | 16 | 5'-TTCTGCACCAAACGTCC-3' | 56.43 |
| FF FR | 17 | 5'-AGCATTGGAGGAAGATGAGG-3' | 59.24 |
|  | 18 | 5'-GCCAATCTACTCCTCTCAGCA-3' | 59.59 |
| GF GR | 19 | 5'-GGCTTTGAATGGTGAGAGGA-3' | 60.20 |
|  | 20 | 5'-TGGATATGAGGGTGGTTGAC-3' | 58.20 |

*The first letter refers to the primer name (A to F) and the second letter indicates the direction of the primer, forward or reverse (e.g. AF, AR).

TABLE 2

Sequences of primers for cloning c4h by 5' and 3' RACE*

| Primer ID | SEQ ID NO | Primer Sequence (5' to 3') | Tm (° C.) |
|---|---|---|---|
| SP1 | 21 | 5'-TTCCTCCAGTGCTCACCATAC-3' | 60.13 |
| SP2 | 22 | 5'-GGTATAGAACTGGGAAGGGACA-3' | 59.35 |
| SP3 | 23 | 5'-CAGGGGATGACACAACAACT-3' | 58.41 |
| SP4 | 24 | 5'-AGAGGAGAAGCACGTTGAGG-3' | 59.60 |
| Oligo dT-Anchor | 25 | 5'-GACCACGCGTATCGATGTCGACTTTTTTTTTTTTTTTV-3' V = A, C, or G | n/a |
| PCR Anchor | 26 | 5'-GACCACGCGTATCGATGTCGAC-3' | 67.13 |

*Primers SP1, SP2, SP3, and SP4 were designed based on the c4h gene sequence in potato. The remaining primers were supplied with the 5'/3' RACE kit. Abbreviation: SP - sequence specific primer.

TABLE 3

Sequence of the c4h gene in potato (SEQ ID NO:1)

| 1 | AAACATTCTT | TTCTCAAACT | TCCCTCTGAA | AGAACTCACC | AAAAATGGAT | 5'-UTR |
| 51 | CTTCTCTTAC | TGGAGAAGAC | CTTAATAGGT | CTTTTCTTTG | CTATTTTAAT | |
| 101 | CGCTATTATT | GTCTCTAAAC | TTCGTTCCAA | GCGATTTAAA | CTACCCCCAG | |

TABLE 3-continued

Sequence of the c4h gene in potato (SEQ ID NO:1)

```
 151 GTCCAATTCC AGTCCCAGTT TTTGGAAATT GGCTTCAAGT TGGTGATGAT
 201 TTGAACCATA GAAACCTTAC TGAGTATGCT AAAAAGTTTG GTGATGTGTT
 251 CTTGCTTAGA ATGGGGCAAA GGAACTTAGT TGTTGTGTCA TCCCCTGAAT
 301 TAGCTAAAGA AGTTTTACAC ACACAAGGGG TTGAATTTGG TTCAAGAACA
 351 AGAAATGTTG TTTTTGATAT TTTTACAGGG AAGGGTCAAG ATATGGTTTT
 401 TACAGTGTAT GGTGAGCACT GGAGGAAAAT GAGGAGGATT ATGACTGTAC Exon 1
 451 CCTTTTTTAC TAATAAGGTG GTGCAGCAGT ATAGAGGGGG GTGGGAGTCT
 501 GAGGCTGCTA GTGTAGTTGA GGATGTGAAG AAAAACCCTG AATCTGCTAC
 551 AAATGGGATT GTTTTGAGGA AAAGATTGCA GCTTATGATG TATAATAACA
 601 TGTTTAGGAT TATGTTTGAT AGGAGATTTG AGAGTGAAGA TGATCCCCTT
 651 TTTGTTAAGC TTAGGGCTTT GAATGGTGAG AGGAGTAGAT TGGCTCAGAG
 701 CTTTGAGTAC AACTATGGTG ATTTTATCCC TATTTTGAGG CCTTTCTTGA
 751 GAGGGTACTT GAAGATTTGT AAGGAGGTTA AGGAGAAGAG GTTGAAGCTA
 801 TTCAAAGACT ACTTTGTTGA TGAAAGAAAG TAAGTTCACT TTTTTCTTGT
 851 TAATCCCTTT ATGCTCAATT TGATCATTTG TATCAGTTTT ATTTATTAGT
 901 TTAGTTTAGT TGTAAGGGGT GTTTGACTAA ATCTTGGAAC AGTATGGATC
 951 AATTTTGAAT AGAAAAGGAA GTACTAGTTG ACATTTCAGA ATAGTAAGGG
1001 TCCATTGGTT AAATTTTAAA AAAGGTAGTT CTTGTTTTCT GTTTTCAAAG
1051 TGATAATGAA AATTAGCGTG GTGTTTGGCA TATTTGGAGT TGTTTTGCGA Intron 1
1101 TTCTCCTGTG GCAATTAGAG GTTTGTCGTA ACGGTGGCCT GTGAGAGCCT
1151 AGCTTGCAGT GGTAAGAGTA GTGAGTGATT TGGAGTAAAA AAGTTAATAA
1201 CTTTTTGATT GATGTTTTTT AAATTTTTAG TTGAATTCCA GAATTGGCCA
1251 ATAAGAATCA TGTATGATTT AGTGATAGTT AAAGTGCTTT GAGGTACTGT
1301 TAGGTAGCTT TTGATGGTGG ACCTTGTGTT TTAGTTTGTA ATATTTTTAT
1351 TGCTTTACAC AGGAAGCTTG CAAATACCAA GAGCATGGAC AGCAATGCTC
1401 TAAAATGTGC AATTGATCAC ATTCTTGAAG CTCAACAGAA GGGAGAGATC Exon 2
1451 AACGAGGATA ACGTTCTTTA CATCCTTGAG AACATCAATG TTGCTGGTAT
1501 GTTTCGAAAT AACATATCTT TGATTCTCTA GAGTAAAATT TGTTCTAGTT
1551 TGGTTTAAAT GATTGCATCC TAGTTAGAAT AAAAGTAATT TATAAGTGAA
1601 TGAAAATCCA ATTCCAATTT TGTCTATTTT TCTCAAAAGT AGTAGTTGAG
1651 AGTTACCAAA TAAGGGGCCC AAGATTTAAC TGTTTTTTAT GTTGCCAAGG
1701 ACTAGTTGGT GCCTGGGCCC TGGGGGGTAC ACACACCAA TTTCTTGTGG
1751 TAAATAAGAT GTTATGTTTA CATCCAAGGA AGACATGTAG TTTCCAAGTT
1801 TGAAGGGGAA ATAAGTACTA TAGTAAAATG AACCACATGT TTCAAGTGAT
1851 GGCGATGTTT CTAGGCTAGG TTACAAAGAC TTGTTAGGTA CCACAATTCT Intron 2
1901 TATACTACTA TAAGACTTAA GTCCCAAACA AGTTGGATA CAATCGGGTT
1951 CTATGGGTTT TACTGAATTC ATTGCTTTTG AAGTGTGCAT ACATATGAAA
2001 AAGAATTTGT AATGTATACA TATGTAATGA GATCATACAT ATTTTGAACT
2051 CAATAACGGG TAGATCTTGG AATTGCCTCT TGTCCGGAAG TTGTTTCATT
```

TABLE 3-continued

Sequence of the c4h gene in potato (SEQ ID NO:1)

```
2101 TATTGCATCG CCTTGTAGTA AGTAATACAT GAGTTTTGAT ATGGTCTTAA

2151 ACTTAAAAAG TCACACATCC TACCATTGAA GCATGTTTTG TTGTTTATAT

2201 CTGTTCGTAA ACTTCTTGGT TAGTTGATTA TTCAGCTGAT ATGCTTAATT

2251 ACTGTCGTGA CCAGCAATCG AAACAACATT GTGGTCAATT GAGTGGGGTA

2301 TCGCGGAACT AGTCAACCAC CCTCATATCC AAAAGAAACT CCGTGATGAG

2351 ATTGATACAG TTCTTGGACC AGGAATGCAA GTGACTGAGC CAGACATGCC

2401 CAAGCTTCCG TACCTTCAGG CTGTGATCAA GGAGACTCTT AGACTCAGGA

2451 TGGCAATTCC TCTTTTAGTC CCACACATGA ACCTTCATGA TGCAAAGCTT

2501 GCTGGATACG ATATTCCAGC TGAAAGCAAA ATCTTAGTTA ACGCTTGGTG Exon3

2551 GCTAGCTAAC AACCCCGCTC ACTGGAAGAA ACCTGAACAG TTCAGACCTG

2601 AGAGGTTCTT CGAAGAGGAG AAGCACGTTG AGGCCAATGG CAACGACTTC

2651 AGATTTCTTC CTTTCGGTGT TGGTAGGAGG AGTTGCCCCG GAATTATCCT

2701 TGCATTGCCA ATTCTCGGCA TCACTTTGGG ACGTTTGGTG CAGAACTTTG

2751 AGATGTTGCC TCCTCCAGGA CAGTCAAAGC TCGACACCTC GGAGAAAGGT

2801 GGACAGTTCA GTCTCCACAT TTTGAAGCAT TCCACCATTG TGATGAAACC

2851 AAGATCTTTC TAAACTTTGT AATGCTATCA ATTAATCATG ATTGTTGTTT

2901 GTTTGTGTAA ACCTTTTAAG TTTGACAGAA AACATTCTTC TTTCTTATGT 3'-UTR

2951 TTTATAAAAG TCTTATTGGA CTAGATTATT CATTAT
```

TABLE 4

The c4h coding sequence and predicted amino acid (SEQ ID NO:2) sequence in potato

```
  1 ATG GAT CTT CTC TTA CTG GAG AAG ACC TTA ATA GGT CTT TTC TTT GCT ATT
  1 M   D   L   L   L   L   E   K   T   L   I   G   L   F   F   A   I

52 TTA ATC GCT ATT ATT GTC TCT AAA CTT CGT TCC AAG CGA TTT AAA CTA CCC
 18 L   I   A   I   I   V   S   K   L   R   S   K   R   F   K   L   P

103 CCA GGT CCA ATT CCA GTC CCA GTT TTT GGA AAT TGG CTT CAA GTT GGT GAT
 35 P   G   P   I   P   V   P   V   F   G   N   W   L   Q   V   G   D

154 GAT TTG AAC CAT AGA AAC CTT ACT GAG TAT GCT AAA AAG TTT GGT GAT GTG
 52 D   L   N   H   R   N   L   T   E   Y   A   K   K   F   G   D   V

205 TTC TTG CTT AGA ATG GGG CAA AGG AAC TTA GTT GTT GTG TCA TCC CCT GAA
 69 F   L   L   R   M   G   Q   R   N   L   V   V   V   S   S   P   E

256 TTA GCT AAA GAA GTT TTA CAC ACA CAA GGG GTT GAA TTT GGT TCA AGA ACA
 86 L   A   K   E   V   L   H   T   Q   G   V   E   F   G   S   R   T

307 AGA AAT GTT GTT TTT GAT ATT TTT ACA GGG AAG GGT CAA GAT ATG GTT TTT
103 R   N   V   V   F   D   I   F   T   G   K   G   Q   D   M   V   F

358 ACA GTG TAT GGT GAG CAC TGG AGG AAA ATG AGG AGG ATT ATG ACT GTA CCC
120 T   V   Y   G   E   H   W   R   K   M   R   R   I   M   T   V   P

409 TTT TTT ACT AAT AAG GTG GTG CAG CAG TAT AGA GGG GGG TGG GAG TCT GAG
137 F   F   T   N   K   V   V   Q   Q   Y   R   G   G   W   E   S   E

460 GCT GCT AGT GTA GTT GAG GAT GTG AAG AAA AAC CCT GAA TCT GCT ACA AAT
154 A   A   S   V   V   E   D   V   K   K   N   P   E   S   A   T   N

511 GGG ATT GTT TTG AGG AAA AGA TTG CAG CTT ATG ATG TAT AAT AAC ATG TTT
171 G   I   V   L   R   K   R   L   Q   L   M   M   Y   N   N   M   F
```

TABLE 4-continued

The c4h coding sequence and predicted amino acid (SEQ ID NO:2) sequence in potato

```
 562 AGG ATT ATG TTT GAT AGG AGA TTT GAG AGT GAA GAT GAT CCC CTT TTT GTT
 188 R   I   M   F   D   R   R   F   E   S   E   D   D   P   L   F   V

613 AAG CTT AGG GCT TTG AAT GGT GAG AGG AGT AGA TTG GCT CAG AGC TTT GAG
 205 K   L   R   A   L   N   G   E   R   S   R   L   A   Q   S   F   E

664 TAC AAC TAT GGT GAT TTT ATC CCT ATT TTG AGG CCT TTC TTG AGA GGG TAC
 222 Y   N   Y   G   D   F   I   P   I   L   R   P   F   L   R   G   Y

715 TTG AAG ATT TGT AAG GAG GTT AAG GAG AAG AGG TTG AAG CTA TTC AAA GAC
 239 L   K   I   C   K   E   V   K   E   K   R   L   K   L   F   K   D

766 TAC TTT GTT GAT GAA AGA AAGAAG CTT GCA AAT ACC AAG AGC ATG GAC AGC
 256 Y   F   V   D   E   R   K   K   L   A   N   T   K   S   M   D   S

817 AAT GCT CTA AAA TGT GCA ATT GAT CAC ATT CTT GAA GCT CAA CAG AAG GGA
 273 N   A   L   K   C   A   I   D   H   I   L   E   A   Q   Q   K   G

868 GAG ATC AAC GAG CAT AAC GTT CTT TAC ATC GTT GAG AAC ATC AAT GTT GCT
 290 E   I   N   E   D   N   V   L   Y   I   V   E   N   I   N   V   A

919 GCAATC GAA ACA ACA TTG TGG TCA ATT GAG TGG GGT ATC GCG GAA CTA GTC
 307 A   I   E   T   T   L   W   S   I   E   W   G   I   A   E   L   V

970 AAC CAC CCT CAT ATC CAA AAG AAA CTC CGT GAT GAG ATT GAT ACA GTT CTT
 324 N   H   P   H   I   Q   K   K   L   R   D   E   I   D   T   V   L

1021 GGA CCA GGA ATG CAA GTG ACT GAG CCA GAC ATG CCC AAG CTT CCG TAC CTT
 341 G   P   G   M   Q   V   T   E   P   D   M   P   K   L   P   Y   L

1072 CAG GCT GTG ATC AAG GAG ACT CTT AGA CTC AGG ATG GCA ATT CCT CTT TTA
 358 Q   A   V   I   K   E   T   L   R   L   R   M   A   I   P   L   L

1123 GTC CCA CAC ATG AAC CTT CAT GAT GCA AAG CTT GCT GGA TAC GAT ATT CCA
 375 V   P   H   M   N   L   H   D   A   K   L   A   G   Y   D   I   P

1174 GCT GAA AGC AAA ATC TTA GTT AAC GCT TGG TGG CTA GCT AAC AAC CCC GCT
 392 A   E   S   K   I   L   V   N   A   W   W   L   A   N   N   P   A

1225 CAC TGG AAG AAA CCT GAA GAG TTC AGA CCT GAG AGG TTC TTC GAA GAG GAG
 409 H   W   K   K   P   E   E   F   R   P   E   R   F   F   E   E   E

1276 AAG CAC GTT GAG CCC AAT GGC AAC GAC TTC AGA TTT CTT CCT TTC GGT GTT
 426 K   H   V   E   P   N   G   N   D   F   R   F   L   P   F   G   V

1327 GGT AGG AGG AGT TGC CCC GGA ATT ATC CTT GCA TTG CCA ATT CTC GGC ATC
 443 G   R   R   S   C   P   G   I   I   L   A   L   P   I   L   G   I

1378 ACT TTG GGA CGT TTG GTG CAG AAC TTT GAG ATG TTG CCT CCT CCA GGA CAG
 460 T   L   G   R   L   V   Q   N   F   E   M   L   P   P   P   G   Q

1429 TCA AAG CTC GAC ACC TCG GAG AAA GGT GGA CAG TTC AGT CTC CAC ATT TTG
 477 S   K   L   D   T   S   E   K   G   G   Q   F   S   L   H   I   L

1480 AAG CAT TCC ACC ATT GTG ATG AAA CCA AGA TCT TTC TAA
 494 K   H   S   T   I   V   M   K   P   R   S   F   *
```

TABLE 5

Mean relative intensity of c4h expression as detected by Northern hybridization analyses*

| Tuber Sample | Number of Observations | Mean Relative Intensity of c4h Expression | |
|---|---|---|---|
| Dark Diploid (10908.06) | 3 | 1.70 +/− 0.53 | a |
| Russet Burbank | 3 | 1.12 +/− 0.10 | ab |
| Russet Norkotah | 3 | 1.12 +/− 0.11 | ab |
| Light Diploid (CH72.03) | 3 | 0.91 +/− 0.18 | b |

*Means followed by the same letter are not significantly different according to Tukey's hsd test at α = 0.05.

TABLE 6

Length and similarity of plant class I c4h coding sequences to potato

| Species | Length (bp) | Sequence Identity bp (%) | Genbank ® Acc. # |
|---|---|---|---|
| Red Pepper (*Capsicum annuum*) | 1518 | 1379 (91) | AF212318 |
| *Lithospermum* (*Lithospermum erythrorhizon*), c4h-2 | 1518 | 1249 (82) | AB055508 |
| Poplar (*Populus* x *generosa*) | 1518 | 1200 (79) | AF302495 |
| Japanese Aspen (*Populus kitakamiensis*) | 1518 | 1197 (79) | D82815 |
| Quaking Aspen (*Populus tremuloides*) | 1518 | 1194 (79) | U47293 |
| *Lithospermum* (*Lithospermum erythrorhizon*), c4h-1 | 1518 | 1182 (78) | AB055507 |
| Grapefruit (*Citrus x paradisi*) | 1518 | 1159 (76) | AF378333 |
| Chickpea (*Cicer arietinum*) | 1518 | 1155 (76) | AJ007449 |
| Tree Cotton (*Gossypium arboreum*) | 1518 | 1144 (75) | AF286648 |
| Madagascar Periwinkle (*Catharanthus roseus*) | 1518 | 1143 (75) | Z32563 |
| Sweet Orange (*Citrus sinensis*), c4h-2 (Class I) | 1560 | 1113 (73) | AF255014 |
| Alfalfa (*Medicago sativa*) | 1521 | 1112 (73) | L11046 |
| Zinnia (*Zinnia elegans*) | 1518 | 1093 (72) | U19922 |
| Bishop's weed (*Ammi majus*) | 1521 | 1088 (72) | AY219918 |
| Arabidopsis (*Arabidopsis thaliana*) | 1518 | 1083 (71) | U71080 |
| Jerusalem Artichoke (*Helianthus tuberosus*) | 1518 | 1073 (71) | Z17369 |
| Wild Licorice (*Glycyrrhiza echinata*) | 1518 | 1018 (67) | D87520 |

TABLE 7

Length and similarity of plant C4H amino acid sequences to potato

| Species | Length (amino acid) | Sequence Identity amino acid (%) | Genbank ® Accession # |
|---|---|---|---|
| Red Pepper | 505 | 441 (87) | AAG43824 |
| *Lithospermum* | 505 | 425 (84) | BAB71716 |
| Madagascar Periwinkle | 505 | 422 (83) | CAA83552 |
| Tree Cotton | 505 | 420 (83) | AAG10197 |
| Wild Licorice | 505 | 418 (82) | BAA13414 |
| Poplar | 505 | 418 (82) | AAG50231 |
| Japanese Aspen | 505 | 418 (82) | BAA11579 |
| Quaking Aspen | 505 | 415 (82) | AAB67874 |
| Grapefruit | 505 | 413 (81) | AAK57011 |
| Zinnia | 505 | 407 (81) | AAB42024 |
| *Arabidopsis* | 505 | 407 (81) | AAB58355 |
| Jerusalem Artichoke | 505 | 407 (81) | CAA78982 |
| Chick Pea | 505 | 406 (80) | CAA07519 |
| Alfalfa | 506 | 406 (80) | S36878 |
| Bishop's Weed | 506 | 403 (80) | AAO62904 |

TABLE 8

```
                     BOX A                        BOX B
     Potato  MDLLLLLEKTLIGLFFAILIAIIVSKLRSKRFKLPPGPIPVPVFGNWLQVGD   51
 Red Pepper  MDLLLLLEKTLVGLFFAIVVAIIVSKLRSKRFKLPPGPIPVPVFGNWLQVGD
Lithospermum MDLLLLLEKALIGLFFSFIIAIVISKLRSKRFKLPPGPIPVPIFGNWLQVGD
M. Periwinkle MDLLLLEKTLLGLFAAIIVASIVSKLRSKRFKLPPGPIPVPVFGNWLQVGD
 Tree Cotton MDLLFLEKVLISLFFTIIFAILVSKLRSKRFKLPPGPLPIPVFGNWLQVGD
Wild Licorice MDLLLLEKTLLGLFIAAITAIAISKLRSKRFKLPPGPIPVPIFGNWLQVGD
      Poplar MDLLLLEKTLLGSFVAILVAILVSKLRSKRFKLPPGPIPVPVFGNWLQVGD Potato  DLNHRNLTEYAKKFGDVFLLRMGQRNLVVVSSPELAKEVLHTQGVEFGSRT  102
 Red Pepper  DLNHRNLTDYAKKFGDIFLLRMGQRNLVVVSSPESAKEVLHTQGVEFGSRT
Lithospermum DLNHRNLTEYAKKFGEIFLLRMGQRNLVVVSSPDLAKEVLHTQGVEFGSRT
M. Periwinkle DLNHRNLSDYAKKFGEIFLLRMGQRNLVVVSSPELAKEVLHTQGVEFGSRT
 Tree Cotton DLNHRNLTDLAKKFGDIFLLRMGQRNLVVISSPELAKEVLHTQGVEFGSRT
Wild Licorice DLNHRNLTDLAKRFGDIFLLRMGQRNLVVVSSPELAKEVLHTQGVEFGSRT
      Poplar DLNHRNLTDLAKKFGDIFLLRMGQRNLVVVSSPDLSKEVLHTQGVEFGSRT Potato  RNVVFDIFTGKGQDMVFTVYGEHWRKMRRIMTVPFFTNKVVQQYRGGWESE  153
 Red Pepper  RNVVFDIFTGKGQDMVFTVYGEHWRKMRRIMTVPFFTNKVVQQYRGGWESE
Lithospermum RNVVFDIFTGKGQDMVFTVYGEHWRKMRRIMTVPFFTNKVVQQYRKGWESE
M. Periwinkle RNVVFDIFTGKGQDMVFTVYGEHWRKMRRIMTVPFFTNKVVQQYRYGWEEE
 Tree Cotton RNVVFDIFTGKGQDMVFTVYGEHWRKMRRIMTVPFFTNKVVQQYRHGWEDE
Wild Licorice RNVVFDIFTGKGQDMVFTVYGEHWRKMRRIMTVPFFTNKVVQQYRFGWESE
      Poplar RNVVFDIFTGKGQDMVFTVYGEHWRKMRRIMTVPFFTNKVVQQYRYGWEEE
```

TABLE 8-continued

```
       Potato  AASVVEDVKKNPESATNGIVLRKRLQLMMYNNMFRIMFDRRFESEDDPLFV  204
   Red Pepper  VASVVEDVKKNPESATNGIVLRKRLQLMMYNNMFRIMFDRRFESEDDPPFV
  Lithospermum  VESVIEDVKKIPESETVGIVLRKRLQLMMYNNMFRIMFDRRFESENDPLFM
  M. Periwinkle AARVVEDVKKNPESATNGIVLRRRLQLMMYNNMYRIMFDRRFESEDDPLFV
   Tree Cotton  AASVVEDVKKNPEAATNGIVLRRRLQLMMYNNMYRIMFDRRFESEEDPLFV
  Wild Licorice AASVVDDVRRNPDAAAGGIVLRRKLQLMMYNNMYRIMFDRRFESEEDPLFV
        Poplar  AAQVVEDVKKNPEAATNGIVLRRKLQLMMYNNMYRIMFDRRFESEEDPLFN Potato  KLRALNGERSRLAQSFEYNYGDFIPILRPFLRGYLKICKEVKEKRLKLFKD  255
   Red Pepper  KLRALNAERSRLAQSFEYNYGDFIPILRPFLRGYLKICKEVKEKRLQLFKD
  Lithospermum  KLRALNGERSRLAQSFDYNYGDFIPILRPFLRGYLKICKEVKETRLKLFKD
  M. Periwinkle KLKALNGERSRLAQGFEYNYGDFIPILRPFLRGYLRICKEVKERRLQLFKD
   Tree Cotton  KLKALNGERSRLAQSFEYNYGDFIPILRPFLRGYLKLCKEVKEIRLQLFRD
  Wild Licorice KLKALNGERSRLAQSFEYNYGDFIPILRPFLKGYLKICKEVKERRLKLFRD
        Poplar  KLKALNGERSRLAQSFDYNYGDFIPILRPFLRGYLKICQEVKERRLQLFRD BOX
       Potato  YFVDERKKLANTKSMDSNALKCAIDHILEAQQKGEINEDVNLYIVENINVA  306
   Red Pepper  YFVDERKKLSNTKSMDSNALKCAIDHILEAQQKGEINEDVNLYIVENINVA
  Lithospermum  YFVEERKKIASTKSTTTNGLKCAIDHILEAQQKGEINEDVNLYIVENINVA
  M. Periwinkle YFVDERKKFGSTKSMDNNSLKCAIDHILEAQQKGEINEDVNLYIVENINVA
   Tree Cotton  QFLEERKKLATTKRIDNNALKCAIDHILDAQRKGEINEDVNLYIVENINVA
  Wild Licorice YFVDERMKLESTKSTSNEGLKCAIDHILDAQKKGEINEDVNLYIVENINVA
        Poplar  YFVDERKKLASTKNMSNEGLKCAIDHILDAQKKGEINEDVNLYIVENINVA C
       Potato  AIETTLWSIEWGIAELVNHPHIQKKLRDEIDTVLGPGMQVTEPDMPKLPYL  357
   Red Pepper  AIETTLWSIEWGIAELVNHPHIQQKLREEIDAVLGPGVQVTEPDTPKLPDL
  Lithospermum  AIETTLWSIEWGIAELVNHPEIQKKLRDEIDTILGPGVQVTEPDTPKLPYL
  M. Periwinkle AIETTLWSIEWGIAELVNHPEIQKKLRDELETVLGPGVQITEPDTYKLPYL
   Tree Cotton  AIETTLWSIEWGIAELVNHPEIQQKLRNEIDTVLGPGVQVTEPDTHKLPYL
  Wild Licorice AIETTLWSIEWGIAELVNHPEIQKKVRDEIDRVLGPGHQVTEPDMQKLPYL
        Poplar  AIETTLWSIEWGIAELVNHPEIQKKLRHELDTLLGPGHQITEPDTYKLPYL Potato  QAVIKETLRLRMAIPLLVPHMNLHDAKLAGYDIPAESKILVNAWWLANNPA  408
   Red Pepper  QAVIKETLRLRMATPLLVPHMNIHDAKLAGYDIPAESKILVNPWWLANNPA
  Lithospermum  QAVIKETLRLRMAIPLLVPHMNLHDAKLNGYDIPAESKILVNAWWLANNPA
  M. Periwinkle QAVIKETLRLRMAIPLFLPHMNLHDAKLGGYDIPAESKILVNAWFLANNPE
   Tree Cotton  QAVIKETLRLRMAIPLLVPHMNLHDAKLGGYDIPAESKILVNAWWLANNPA
  Wild Licorice QAVIKETLRLRMAIPLLVPHMNLHDAKLGGYDIPAESKILVNAWWLANNPA
        Poplar  NAVIKETLRLRMAIPLLVPHMNLHDAKLGGFDIPAESKILVNAWWLANNPA BOX D
       Potato  HWKKPEEFRPERFFEEEKHVEANGNDFRRFLPFGVGRRSCPGIILALPILGI  459
   Red Pepper  HWKKPEEFRPERFLKEEKHVDANGNDFRRFLPFGVGRRSCPGIILALPILGI
  Lithospermum  QWKNPEEFRPERFLEEEAKVEANGNDFRYLPFGVGRRSCPGIILALPILGI
  M. Periwinkle HWKNPEEFRPERFLEEESKVEANGNDFRYLPFGVGRRSCPGIILALPILGI
   Tree Cotton  HWKNPEEFRPERFFEEESKVEANGNDFRYLPFGVGRRSCPGIILALPILGI
  Wild Licorice NWKRPEEFRPERFLEEESHVEANGNDFRYLPFGVGRRSCPGIILALPILGI
        Poplar  HWKNPEEFRPERFLEEEAKVEANGNDFRYLPFGVGRRSCPGIILALPILGI Potato  TLGRLVQNFEMLPPPGQSKLDTSEKGGQFSLHILKHSTIVMKPRSF*  505
   Red Pepper  TLGRLVQNFELLPPPGQSKLDTTEKGGQFSLHILKHSTIVMKPRSF*
  Lithospermum  TLGRLVQNFELLPPPGQSKLDTSEKGGQFSLHILKHSTIVMKPRSF*
  M. Periwinkle TIGRLVQNFELLPPPGKSKLDTSEKGGQFSLHILKHSTIVLKPRTF*
   Tree Cotton  TLGRLVQNFELLPPKGQSKLDTSEKGGQFSLHILKHSTIVAKPRVF*
  Wild Licorice TLGRLVQNFELLPPPGQSKLDTAEKGGQFSLHILKHSTIVAKPRSF*
        Poplar  TLGRLVQNFELLPPPGQSKIDTAEKGGQFSLHILKHSTIVAKPRSF*
```

TABLE 9

The volumes of 18s rRNA primer and competimer to obtain the required 18s rRNA to competimer ratio.

| | Ratio | | |
|---|---|---|---|
| | 1:9 | 2:8 | 3:7 |
| 18s rRNA primer | 1 μl | 2 μl | 3 μl |
| Competimer | 9 μl | 8 μl | 7 μl |

TABLE 10

Summary of statistical analysis on clones of diploid families; 13610-T and 13395-B.

| | 13610-T | 13395-B |
|---|---|---|
| Mean | 108.03 | 112.98 |
| Standard Error | 0.93 | 0.94 |
| Standard Deviation | 11.17 | 7.84 |
| Kurtosis Dark | −0.42 | −0.71 |
| Skewness | −0.09 | 0.10 |
| Minimum | 82.07 | 98.52 |
| Maximum | 134.48 | 132.41 |
| Count | 145 | 69 |
| Confidence Level (95.0%) | 1.83 | 1.88 |

TABLE 11

ACD evaluation data for the selected diploid and tetraploid samples.*

| Family | Clone Number | Degree of ACD | January 2003 Pixel density | January 2004 pixel density | February 2004 pixel density |
|---|---|---|---|---|---|
| 13610-T | 13610 - T - 224 | Dark | 85.4 | 86.3 | 86.3 |
| | 13610 - T - 154 | Dark | 89.3 | 82.8 | 81.9 |
| | 13610 - T - 151 | Dark | 95.8 | 84.9 | 89.0 |
| | 13610 - T - 070 | Light | 140.1 | 128.6 | 136.0 |
| | 13610 - T - 167 | Light | 137.3 | 132.6 | 125.4 |
| | 13610 - T - 231 | Light | 133.0 | 137.8 | 133.2 |
| 13395-B | 13395 - B - 055 | Dark | 103.1 | 113.3 | 120.5 |
| | 13395 - B - 052 | Dark | 105.2 | 100.1 | 111.3 |
| | 13395 - B - 113 | Light | 123.3 | 127.7 | 124.1 |
| | 13395 - B - 096 | Light | 122.0 | 132.1 | 111.4 |
| Tetraploid | Shepody | Dark | 131.2 | 132.2 | 120.6 |
| | Russet Burbank | Light | 124.2 | 126.9 | 129.7 |

*ACD light tubers are determined by higher pixel density values whereas ACD dark tubers have lower pixel density values.

TABLE 12

Candidate gene C4H and its full length cDNA sources used in this study.

| Name of gene candidates | Plant | Gene Sequences |
|---|---|---|
| Cinnamic acid 4-hydroxylase (C4H) | Potato | Identified at NSAC* |

*Cantel, S. 2005.

TABLE 13

Designed primer sets for differential expression analysis of C4H gene.

| Selected primer sets | | Tm ° C. | Length (nt) |
|---|---|---|---|
| Forward Primer | 5'-GAAGGGAGAGATCAACGAGG-3' (SEQ ID NO:27) | 60 | 20 |
| Reverse Primer | 5'-TTCTGCACCAAACGTCC-3' (SEQ ID NO:28) | 57 | 17 |

TABLE 14

Mean ACD values of selected three sample groups grown and harvested in year 2002 and 2003.

| | Mean ACD value in January 2003* (MRD) | Mean ACD value in January 2004* (MRD) | Mean ACD value in February 2004* (MRD) |
|---|---|---|---|
| 13610-T | | | |
| Dark | 90.17 a | 84.67 a | 85.73 a |
| Light | 136.80 b | 133.00 b | 131.53 b |
| 13395-B | | | |
| Dark | 104.15 a | 106.7 a | 115.90 a |
| Light | 122.65 b | 129.9 b | 117.75 a |
| Tetraploid | | | |
| Shepody | 131.20 a | 132.20 a | 120.60 b |
| Russet Burbank | 124.20 b | 126.90 b | 129.70 a |

*Significant difference determined using one-way ANOVA at P < 0.05 and significances are shown as "a" and "b"

TABLE 15

One-way ANOVA results of CgA, CA and CgA to CA ratio contents in the dark and light clones of family 13610-T, 13395-B and tetraploid samples.

| | Mean CgA content (mg $100^{-1}$ g)* | Mean CA content (mg $100^{-1}$ g)* | Mean CgA:CA content (mg $100^{-1}$ g)* |
|---|---|---|---|
| 13610-T | | | |
| Dark | 0.49 a | 808.15 a | $6.06 \times 10^{-4}$ a |
| Light | 0.24 b | 833.47 a | $2.88 \times 10^{-4}$ b |
| 13395-B | | | |
| Dark | 0.06 b | 458.08 a | $1.24 \times 10^{-4}$ b |
| Light | 0.47 a | 393.33 a | $11.95 \times 10^{-4}$ a |
| Tetraploid | | | |
| Shepody (Dark) | 0.12 a | 749.94 a | $1.61 \times 10^{-4}$ a |
| Russet Burbank (Light) | 0.11 a | 724.19 a | $1.51 \times 10^{-4}$ a |

*Small case "a" and "b" refers to significances from one-way ANOVA results at P < 0.05, the analyses were done for dark and light clones of each chemical separately.

TABLE 16

Normalized geene expression level of C4H in ACD dark and light clones of 13610-T diploid family. (MPD-maximum pixel density)

| | PCR 1 | | PCR 2 | | PCR 3 | | PCR 4 | |
|---|---|---|---|---|---|---|---|---|
| | Dark | Light | Dark | Light | Dark | Light | Dark | Light |
| C4H (MPD) | 120.35 | 23.46 | 83.08 | 10.97 | 79.35 | 29.06 | 108.68 | 8.90 |
| Internal Standard (MPD) | 25.35 | 25.64 | 19.56 | 11.48 | 34.33 | 39.16 | 77.48 | 62.15 |
| Blank (MPD) | 4.00 | 4.00 | 3.06 | 3.06 | 2.23 | 2.23 | 4.56 | 4.56 |
| Normalized gene expression level* | 0.53 | 0.10 | 0.47 | 0.11 | 0.26 | 0.08 | 0.16 | 0.02 |

*Gene expression level = $\dfrac{\text{Target gene MPD} - \text{Blank MPD}}{\text{Internal Standard MPD} - \text{Blank MPD}} \times 1:9$

TABLE 17

Normalized gene expression level of C4H in ACD dark and light clones of family 13395-B. (MPD-maximum pixel density)

| | PCR 1 | | PCR 2 | | PCR 3 | | PCR 4 | |
|---|---|---|---|---|---|---|---|---|
| | Dark | Light | Dark | Light | Dark | Light | Dark | Light |
| C4H (MPD) | 58.57 | 22.97 | 44.97 | 32.92 | 45.83 | 22.41 | 61.76 | 28.72 |
| Int. Std (MPD) | 72.76 | 87.67 | 65.67 | 121.11 | 30 | 38.83 | 82.24 | 81.55 |
| Blank (MPD) | 4.53 | 4.53 | 4.76 | 4.76 | 7.67 | 7.67 | 5.89 | 5.89 |
| Normalized gene expression level* | 0.09 | 0.03 | 0.08 | 0.03 | 0.17 | 0.06 | 0.08 | 0.04 |

*Gene expression level = $\dfrac{\text{Target gene MPD} - \text{Blank MPD}}{\text{Internal Standard MPD} - \text{Blank MPD}} \times 1:9$

TABLE 18

Normalized gene expression level of C4H in Shepody and Russet Burbank. (MPD-maximum pixel density)

| | PCR 1 | | PCR 2 | | PCR 3 | | PCR 4 | |
|---|---|---|---|---|---|---|---|---|
| | Dark | Light | Dark | Light | Dark | Light | Dark | Light |
| C4H (MPD) | 210.41 | 89.25 | 190.4 | 142.62 | 180 | 32.11 | 129.14 | 56.91 |
| Internal Standard (MPD) | 57.45 | 88.41 | 16.03 | 35.63 | 70.62 | 45.11 | 85.92 | 192.47 |
| Blank (MPD) | 0.00 | 0.00 | 7.21 | 7.21 | 3.23 | 3.23 | 0.00 | 0.00 |
| Normalized gene expression level* | 0.41 | 0.11 | 1.32 | 0.44 | 0.28 | 0.08 | 0.17 | 0.03 |

*Gene expression level = $\dfrac{\text{Target gene MPD} - \text{Blank MPD}}{\text{Internal Standard MPD} - \text{Blank MPD}} \times 1:9$

TABLE 19

Ct values of real-time PCR for gene expression of C4H in 13610-T clones.

| Sample | C4H ct | Ubi3 ct | A | B |
|---|---|---|---|---|
| 13610-T Dark -1 | 24.5 | 20.74 | 3.76 | |
| 13610-T Dark -2 | 24.04 | 20.86 | 3.18 | |
| 13610-T Light -2 | 23.45 | 18.81 | | 4.64 |
| 13610-T Light -2 | 22.85 | 19.02 | | 3.83 |

| Clones | A − B = C | Fold change (dark/light) |
|---|---|---|
| Dark | −0.88 | 1.840 |
| Light | −0.65 | 1.569 |

TABLE 20

Ct values of real-time PCR for gene expression of C4H in 13610-B clones.

| Sample | C4Hct | Ubi3 ct | A | B |
|---|---|---|---|---|
| 13610-B Dark -1 | 22.15 | 17.00 | 5.15 | |
| 13610-B Dark -2 | 23.43 | 17.54 | 5.89 | |
| 13610-B Light -2 | 23.11 | 17.38 | | 5.73 |
| 13610-B Light -2 | 24.60 | 18.09 | | 6.51 |

TABLE 20-continued

Ct values of real-time PCR for gene expression of C4H in 13610-B clones.

| Clones | A − B = C | Fold change (dark/light) |
|---|---|---|
| Dark | −0.58 | 1.495 |
| Light | −0.62 | 1.537 |

TABLE 21

Chlorogenic acid content in different parts of the tuber tissue of potato cultivar Russet Burbank.

| Tuber Parts | Chlorogenic Acid* (:g/100 g fresh tissue) |
|---|---|
| Stem end | 50.4364 a |
| Apical end | 39.9151 b |
| Center region | 18.7739 c |
| Exterior region | 38.35335 b |

*Means followed by the same letter are not significantly different according to Tukey's hsd test at α = 0.05.

REFERENCES

Agrawal, N., P. V. N. Dasaradhi, Asif Mohmmed, Pawan Malhotra, Raj K. Bhatnagar, and Sunil K. Mukherjee. RNA Interference: Biology, Mechanism, and Applications. Microbiology and Molecular Biology Reviews, 2003, 67(4): 657-685.

Altschul, S. F., Gish, W., Miller, W., Myers, E. W., and Lipman, D. J. 1990. Basic local alignment search tool. J. Mol. Biol. 215: 403-410.

Arumuganathan, K. and Earle, E. D. 1991. Nuclear DNA content of some important plant species. Plant Mol. Biol. Rep. 9: 211-215.

Bachem, C. W. B., van der Hoeven, R. S., de Brujin, S. M., Vreugdenhil, D., Zabeau, M., and Visser, R. G. F. 1996. Visualization of differential gene expression using a novel method of RNA fingerprinting based on AFLP: Analysis of gene expression during potato tuber development. Plant J. 9: 745-753.

Bassett, C. L., Artlip, T. S., and Callahan, A. M. 2002. Characterization of the peach homologue of the ethylene receptor, PpETR1, reveals some unusual features regarding transcript processing. Planta 215: 679-688.

Batard, Y., Schalk, M., Pierrel, M., Zimmerlin, A., Durst, F., and Werck-Reichhart, D. 1997. Regulation of the cinnamate 4-hydroxylase (CYP73A1) in Jerusalem artichoke tubers in response to wounding and chemical treatments. Plant Physiol. 113: 951-959.

Belasco, J. G. and Higgins, C. F. 1988. Mechanisms of mRNA decay in bacteria: a perspective. Gene 72: 15-23.

Bell-Lelong, D. A., Cusumano, J. C., Meyer K. and Chapple, C. 1997. Cinnamate-4-Hydroxylase Expression in *Arabidopsis* (Regulation in Response to Development and the Environment). Plant Physiol. 113: 729-738.

Betz, C., McCollum, T. G., and Mayer, R. T. 2001. Differential expression of two cinnamate 4-hydroxylase genes in 'Valencia' orange (*Citrus sinensis* Osbeck). Plant Mol. Biol. 46: 741-748.

Blee, K., Choi, J. W., O'Connell, A. P., Jupe, S. C., Schuch, W., Lewis, N. G., and Bolwell, G. P. 2001. Antisense and sense expression of cDNA coding for CYP73A15, a class II cinnamate 4-hydroxylase, leads to a delayed and reduced production of lignin in tobacco. Phytochemistry 57: 1159-1166.

Bradshaw, J. E., Barker, H., Dale, M. F. B., Mackay, G. R., Millam, S., Solomon-Blackburn, R. M., and Stewart, H. E. 1998. Scottish Crop Research Institute Annual Report 1997/1998. Scottish Crop Research Institute. http://www.scri.sari.ac.uk/Date Accessed: Nov. 21, 2001.

Cantle, S. 2005. Gene structure and expression of cinnamic acid 4-hydroxylase in potato and its relationship to after-cooking darkening. Thesis. Dalhousie University, Halifax, Canada.

Chapple, C. 1998. Molecular genetic analysis of plant cytochrome P450-dependent monooxygenases. Annu. Rev. Plant Physiol. Plant Mol. Biol. 49: 311-343.

Chubey, B. B. and Mazza, G. 1983. A non-destructive method for rapid evaluation of boiling quality of potato tubers. Am. Potato J. 60: 693-698.

Dale, M. F. B. and Mackay, G. R. 1994. Inheritance of table and processing quality. In: Bradshaw, J. E. and Mackay, G. R. (eds), Potato Genetics. CAB International Publishers, Wallingford, UK. pp. 296-298.

Derek M. dykxhoorn, Carl D. Novina and Phillip A. Sharp. Killing the messenger: Short RNAs that silence gene expression. Nature, 2003, 4: 457-467.

Deutsch, M. and Long, M. 1999. Intron-exon structure of eukaryotic model organisms. Nucleic Acids Res. 27: 3219-3228.

Dinesh-Kumar, S. P. and Baker, B. J. 2000. Alternatively spliced N resistance gene transcripts: their possible role in tobacco mosaic virus resistance. Proc. Natl. Acad. Sci. USA 97: 1908-1913.

Doyle, J. J. and Doyle, J. L. 1990. Isolation of plant DNA from fresh tissue. Focus 1: 13-15.

Ellis, T. H. N. and Poyser, S. J. 2002. An integrated and comparative view of pea genetic and cytogenetic maps. New Phytol. 153: 17-25.

Fahrendorf, T. and Dixon, R. A. 1993. Stress responses in alfalfa (*Medicago sativa* L.) XVIII: Molecular cloning and expression of the elicitor-inducible cinnamic acid 4-hydroxylase cytochrome P450. Arch. Biochem. Biophy. 305: 509-515.

Floyd, S. K. and Bowman, J. L. 2004. Ancient microRNA target sequences in plants. Nature 428: 485-486.

Friedman, M. 1997. Chemistry, biochemistry, and dietary role of potato polyphenols. J. Agric. Food Chem. 45: 1523-1540.

Griffiths, D. W, Bain, H., and Dale, M. F. B. 1992. Development of arapid colorimetric method for the determination of chlorogenic acid in freeze-dried potato tubers. J. Sci. Food Agr. 58: 41-48.

Griffiths, D. W. and Bain, H. 1997. Photo-induced changes in the concentrations of individual chlorogenic acid isomers in potato (*Solanum tuberosum*) tubers and their complexation with ferric ions. Potato Res. 40: 307-315.

Groenewald, J. H., Hiten, N. F., and Botha, F. C. 2000. The introduction of an inverted repeat to the 5' untranslated leader sequence of a transgene strongly inhibits gene expression. Plant Cell Rep. 19: 1098-1101.

Hotze, M., Schröder, G., and Schröder, J. 1995. Cinnamate 4-hydroxylase from *Catharanthus roseus*, and a strategy for the functional expression of plant cytochrome P450 proteins as translational fusions with P450 reductase in *Escherichia coli*. FEBS Lett. 374: 345-350.

Hughes, J. C. and Swain, T. 1962a. After-cooking blackening in potatoes. II. Core experiments. J. Sci. Food Agr. 13: 229-236.

Hughes, J. C. and Swain, T. 1962b. After-cooking blackening in potatoes. III. Examination of the interaction of factors by in vitro experiments. J. Sci. Food Agric. 13: 358-363.

Hughes, J. C. 1962. Chemistry of after-cooking discoloration in potatoes. J. Nat. Inst. Agric. Bot. 9: 235-236.

Inoue, H., Nojima, H., and Okayama, H. 1990. High efficiency transformation of *Escherichia coli* with plasmids. Gene 96: 23-28.

Kawai, S., Mori, A., Shiokawa, T., Kajita, S., Katayama, Y., and Morohoshi, N. 1996. Isolation and analysis of cinnamic acid 4-hydroxylase homologous genes from a hybrid aspen, *Populus kitakamiensis*. Biosci. Biotech. Biochem. 60: 1586-1597.

Ke, X., Liu, C., Liu, D., and Liang, C. 2003. MicroRNAs: key participants in gene regulatory networks. Curr. Opin. Chem. Biol. 7: 516-523.

Kendziorski, C. M., Zhang, Y., Lan, H. and Attie, A. D. 2003. The efficiency of pooling mRNA in microarray experiments. Biostatistics 4: 465-477.

Kochetov, A. V., Sirnik, 0. A., Rogosin, I. B., Glazko, G. V., Komarova, M. L., and Shumny, V. K. 2002. Contextual features of higher plant mRNA 5'-untranslated regions. Mol. Biol. 36: 510-516.

Konig, H., Ponta, H., and Herrlich, P. 1998. Coupling of signal transduction to alternative pre-mRNA splicing by a composite splice regulator. EMBO J. 17: 2904-2913.

Koopmann, E., Logemann, E., and Hahlbrock, K. 1999. Regulation and functional expression of cinnamate 4-hydroxylase from parsley. Plant Physiol. 119: 49-55.

Kuhn, J., Tengler, U., and Binder, S. 2001. Transcript lifetime is balanced between stabilizing stem-loop structures and degradation-promoting polyadenylation in plant mitochondria. Mol. Cell. Biol. 21: 731-742.

Kühnl, T., Koch, U., Heller, W., and Wellmann, E. 1987. Chlorogenic acid biosynthesis: characterization of a light-induced microsomal 5-O-(4-coumaroyl)-D-quinate/shikimate 3'-hydroxylase from carrot (*Daucus carota* L.) cell suspension cultures. Arch. Biochem. Biophys. 258: 226-232.

Landschutze V, Muller-Rober B and Willmitzer L, 1995. Mitochondrial citrate synthase from potato: predominant expression in mature leaves and young flower buds. Planta, 196: 756-64.

Lewis, C. E., Walker, J. R. L., Lancaster, J. E., and Sutton, K. H. 1998. Determination of anthocyanins, flavonoids, and phenolic acids in potatoes. I: Colored cultivars of *Solanum tuberosum* L. J. Sci. Food Agric. 77: 45-57.

Lugasi, A., Almeida, D. P. F., and Dworschak, E. 1999. Chlorogenic acid content and antioxidant properties of potato tubers as related to nitrogen fertilization. Acta Aliment. 28: 183-195.

Ma, R., Cohen, M. B., Berenbaum, M. R., Schuler, M. A. 1994. Black swallowtail (*Papilio polyxenes*) alleles encode cytochrome P450 s that selectively metabolize linear furanocoumarins. Arch Biochem Biophys 310: 332-340.

McLysaght, A., Enright, A. J., Skrabanek, L., and Wolfe, K. H. 2000. Estimation of synteny conservation and genome compaction between pufferfish (*Fugu*) and human. Yeast 17: 22-36.

Miller, C. L., Diglisic, S., Leister, F., Webster, M., and Yolken, R. H. 2004. Evaluating RNA status for RT-PCR in extracts of postmortem human brain tissue. BioTechniques 36: 628-633.

Mizutani, M., Ohta, D., and Sato, R. 1997. Isolation of a cDNA and a genomic clone encoding cinnamate 4-hydroxylase from *Arabidopsis* and its expression manner in planta. Plant Physiol. 113: 755-763.

Moriyama, E. N., Petrov, D. A., and Hartl, D. L. 1998. Genome size and intron size in *Drosophila*. Mol. Biol. Evol. 15: 770-773.

Nedelkina, S., Jupe, S. C., Blee, K. A., Schalk, M., Werck-Reichhart, D., and Bolwell, G. P. 1999. Novel characteristics and regulation of a divergent cinnamate 4-hydroxylase (CYP73A15) from French bean: engineering expression in yeast. Plant Mol. Biol. 39: 1079-1090.

Niggeweg R, Michael A J, Martin C, 2004. Engineering plants with increased levels of the antioxidant chlorogenic acid. Nat. Biotech. 22: 746-754.

Palmer, M. and Prediger, E. 2004. TechNotes 11: Assessing RNA quality. Ambion, Inc. http://www.ambion.com/techlib/tn/111/8.html Date Accessed: May 23, 2004.

Percival, G. C. and Baird, L. 2000. Influence of storage upon light-induced chlorogenic acid accumulation in potato tubers (*Solanum tuberosum* L.). J. Agric. Food Chem. 48: 2476-2482.

Petit J M, Wuytswinkel O V, Briat J F, Lobréaux S (2001) Characterization of an iron-dependent regulatory sequence involved in the transcriptional control of atfer1 and zmfer1 plant ferritin genes by iron. J Biol Chem 276: 5584-5590.

Pesole, G., Liuni, S., Grillo, G., and Saccone, C. 1997. Structural and compositional features of untranslated regions of eukaryotic mRNAs. Gene 205: 95-102.

Petersen, M. 2003. Cinnamic acid 4-hydroxylase from cell cultures of the hornwort *Anthoceros agrestis*. Planta 217: 96-101.

Rhoades, M. W., Reinhart, B. J., Lim, L. P., Burge, C. B., Bartel, B., and Bartel, D. P. 2002. Prediction of plant microRNA targets. Cell 110: 513-520.

Ro, D. K., Mah, N., Ellis, B. E., and Douglas, C. J. 2001. Functional characterization and subcellular localization of popular (*Populus trichocarpa×Populus deltoids*) cinnamate 4-hydroxylase. Plant Physiol. 126: 317-329.

Sambrook, J. and Russell, D. W. 2001a. Molecular Cloning: A Laboratory Manual 3$^{rd}$ Ed., Volume 1. Cold Spring Harbor Laboratory Press, New York, USA. pp. 1.31-1.34, 7.70-7.72, 7.31-7.34.

Sambrook, J. and Russell, D. W. 2001b. Molecular Cloning: A Laboratory Manual 3$^{rd}$ Ed., Volume 2. Cold Spring Harbor Laboratory Press, New York, USA. pp. 8.112-8.113.

Sambrook, J. and Russell, D. W. 2001c. Molecular Cloning: A Laboratory Manual 3$^{rd}$ Ed., Volume 3. Cold Spring Harbor Laboratory Press, New York, USA. pp. A2.2-A2.3.

Schalk, M., Nedelkina, S., Schoch, G., Batard, Y., and Werck-Reichhart, D. 1999. Role of unusual amino acid residues in the proximal and distal heme regions of a plant P450, CYP73A1. Biochem. 38: 6093-6103.

Schattat, M. H., Klosgen, R. B., and Maroues, J. P. A Novel Vector for Efficient Gene Silencing in Plants. Plant Molecular Biology Reporter, 2004, 22: 145-153.

Siciliano J, Heisler E G, and Porter W L, 1969. Relation of potato size to after-cooking blackening tendency. Am. Potato J. 46: 91-97.

Singh G, Kumar S and Singh P, 2003. A quick method to isolate RNA from wheat and other carbohydrate rich seeds. Plant mol. bio. rep. 21: 93a-93f.

Smith, O. 1987. Effect of cultural and environmental conditions on potatoes for processing. In: Talburt, W. F. and Smith, O. (eds), Potato Processing 4$^{th}$ Ed. Van Nostrand Reihold Company Inc., New York, USA. pp. 107-119.

Sullivan, M. L. and Green, P. J. 1996. Mutational analysis of the DST element in tobacco cells and transgenic plants: identification of residues critical for mRNA instability. RNA 2: 308-315.

Susi, P., Hohkuri, M., Wahlroos, T. and Kilby, N. J. 2004. Characteristics of RNA silencing in plants: similarities and differences across kingdoms. Plant Molecular Biology, 00: 1-18.

Swiniarski, E. 1968. Zwiazek pomiedzy ciemnieniem ziemniaka po ugotowaniu a niektorymi czynnikami jego skladu (After-cooking darkening and some chemical constituents of potato tubers). Hod Rost Akl Nas 12: 369-384.

Tanaka, Y., Kojima, M., and Uritani, I. 1974. Properties, development, and cellular-localization of cinnamic acid 4-hydroxylase in cut-injured sweet potato. Plant Cell Physiol. 15: 843-854.

Tanzer, M. M. and Meagher, R. B. 1994. Faithfuil degradation of soybean rbcS mRNA in vitro. Mol. Cell. Biol. 14: 2640-2650.

Taylor, G. 2002. *Populus: Arabidopsis* for forestry. Do we need a model tree? Ann. Bot. 90: 681-689.

The Arabidopsis Genome Initiative. 2000. Analysis of the genome sequence of the flowering plant *Arabidopsis thaliana*. Nature 408: 796-815.

Topley H, 2004. Thesis: Gene expression analysis of potato (*Solanum tuberosum* L.CV. Russet Burbank) tubers during long-term storage and its relationship with after-cooking darkening.

Wang-Pruski G. 2006. Digital imaging for evaluation of potato after-cooking darkening and its comparison with other methods. Inter J Food Sci and Tech in press.

Wang-Pruski, G. and Tarn, T. R. 2003. Digital imaging analysis—a new method for evaluation of potato after-cooking darkening. Acta Hort. 619: 399-404.

Wang-Pruski, G. and Nowak, J. 2004. Potato after-cooking darkening. Amer. J. Potato Res. 81: 7-16.

Wang-Pruski, G., Astatkie, T., DeJong, H., Lederc, Y. 2003. Genetic and environmental interactions affecting potato after-cooking darkening. Acta Hort 619: 45-52.

Wendel, J. F., Cronn, R. C., Alvarez, I., Liu, B., Small, R. L., and Senchina, D. S. 2002. Intron size and genome size in plants. Mol. Biol. Evol. 19: 2346-2352.

Whitbred, J. M. and Schuler, M. A. 2000. Molecular characterization of CYP73A9 and CYP82A1 P450 genes involved in plant defense in pea. Plant Physiol. 124: 47-58.

Xie, Z., Kasschau, K. D., and Carrington, J. C. 2003. Negative feedback regulation of Dicer-Like1 in *Arabidopsis* by microRNA-guided mRNA degradation. Curr. Biol. 13: 784-789.

Xuejun, P., Constance, L. W., Eric, M. B., Kuey, C. C., Philip, W. L. and Arnold, J. S. 2003. Statistical implications pooling RNA samples for microarray experiments. BMC Bioinformatics (www.biomedcentral.com/1471-2105/4/26)

Yao, K., De Luca, V., and Brisson, N. 1995. Creation of a metabolic sink for tryptophan alters the phenylpropanoid pathway and the susceptibility of potato to *Phytophthora infestans*. Plant Cell 7: 1787-1799.

Yu, H. and Kumar, P. P. 2003. Post-transcriptional gene silencing in plants by RNA. Plant Cell Rep. 22: 167-174.

Zufall, R. A. and Rausher, M. D. 2003. The genetic basis of a flower color polymorphism in the common morning glory (*Ipomoea purpurea*). J. Hered. 94: 442-448.

We claim:

1. A method of determining the susceptibility of a potato to after-cooking darkening (ACD) comprising assaying a potato sample for a nucleic acid molecule encoding a cinnamic acid 4-hydroxylase (C4H) protein from potato shown in SEQ ID NO:2 wherein the nucleic acid is detected using RT-PCR or real time quantitative PCR using a forward primer of SEQ ID NO: 27 and a reverse primer of SEQ ID NO: 28 and wherein increased levels of the C4H nucleic acid indicates that the potato is more susceptible to ACD.

2. The method of claim 1 wherein the nucleic acid molecule has the sequence shown in SEQ ID NO: 1.

3. The method of claim 1 wherein the potato is the potato cultivar Russet Burbank or Shepody.

* * * * *